United States Patent
Zubarev et al.

(10) Patent No.: US 11,572,442 B2
(45) Date of Patent: Feb. 7, 2023

(54) COMPOUND, POLYIMIDE RESIN AND METHOD OF PRODUCING THE SAME, PHOTOSENSITIVE RESIN COMPOSITION, PATTERNING METHOD AND METHOD OF FORMING CURED FILM, INTERLAYER INSULATING FILM, SURFACE PROTECTIVE FILM, AND ELECTRONIC COMPONENT

(71) Applicants: International Business Machines Corporation, Armonk, NY (US); Shin-Etsu Chemical Co., Ltd., Tokyo (JP)

(72) Inventors: Dmitry Zubarev, San Jose, CA (US); Hiroyuki Urano, Joetsu (JP); Katsuya Takemura, Joetsu (JP); Masashi Iio, Joetsu (JP); Kazuya Honda, Yokohama (JP); Yoshio Kawai, Kawasaki (JP)

(73) Assignees: International Business Machines Corporation, Armonk, NY (US); Shin-Etsu Chemical Co., Ltd., Tokyo (JP)

( * ) Notice: Subject to any disclaimer, the term of this patent is extended or adjusted under 35 U.S.C. 154(b) by 31 days.

(21) Appl. No.: 16/848,439

(22) Filed: Apr. 14, 2020

(65) Prior Publication Data
US 2021/0317270 A1 Oct. 14, 2021

(51) Int. Cl.
| | | |
|---|---|---|
| C08G 73/14 | (2006.01) | |
| G03F 7/023 | (2006.01) | |
| G03F 7/038 | (2006.01) | |
| G03F 7/38 | (2006.01) | |
| G03F 7/40 | (2006.01) | |
| C07C 63/49 | (2006.01) | |
| C07C 211/49 | (2006.01) | |
| C07C 233/65 | (2006.01) | |
| G03F 7/022 | (2006.01) | |
| G03F 7/039 | (2006.01) | |
| G03F 7/16 | (2006.01) | |

(Continued)

(52) U.S. Cl.
CPC ............. *C08G 73/14* (2013.01); *C07C 63/49* (2013.01); *C07C 211/49* (2013.01); *C07C 233/65* (2013.01); *G03F 7/022* (2013.01); *G03F 7/0226* (2013.01); *G03F 7/0233* (2013.01); *G03F 7/039* (2013.01); *G03F 7/0387* (2013.01); *G03F 7/38* (2013.01); *C07C 2601/08* (2017.05); *C07C 2601/14* (2017.05); *C07C 2601/16* (2017.05); *G03F 7/162* (2013.01); *G03F 7/20* (2013.01); *G03F 7/322* (2013.01); *G03F 7/40* (2013.01)

(58) Field of Classification Search
CPC .... G03F 7/0233; G03F 7/0226; G03F 7/0387; G03F 7/38; G03F 7/40; C08G 69/26; C08G 73/14

See application file for complete search history.

(56) References Cited

U.S. PATENT DOCUMENTS

| | | | |
|---|---|---|---|
| 3,947,451 A | 3/1976 | Jonsson et al. | |
| 7,371,501 B2 * | 5/2008 | Yamanaka | G03F 7/0233 430/326 |
| 8,709,552 B2 * | 4/2014 | Miyoshi | H01L 51/5284 522/143 |
| 10,457,779 B2 * | 10/2019 | Takemura | G03F 7/0226 |
| 2005/0259203 A1 * | 11/2005 | Kimura | G02F 1/133788 349/124 |
| 2009/0181224 A1 | 7/2009 | Minegishi | |

(Continued)

FOREIGN PATENT DOCUMENTS

| | | |
|---|---|---|
| EP | 3604390 A1 | 2/2020 |
| JP | 49115541 U | 10/1974 |

(Continued)

OTHER PUBLICATIONS

List of IBM Patents or Patent Applications Treated as Related.
Extended European Search Report dated Jul. 20, 2021, for counterpart EP Application No. 21156605.4.
Extended European Search Report dated Aug. 17, 2021, for related EP Application No. 21156645.0.
Strijckmans et al., Synthesis of a potential MI muscarinic agent [76Br] bromocaramiphen, Journal of Labelled Compounds and Radiopharmaceuticals 38(5):471-481 (1996).

*Primary Examiner* — John S Chu
(74) *Attorney, Agent, or Firm* — Karen Canaan; CanaanLaw, P.C.

(57) ABSTRACT

Provided is a compound that can be used as a base resin for a photosensitive resin composition. The photosensitive resin can form a fine pattern and can achieve high resolution without impairing mechanical strength and solubility. The compound is represented by the general formula (1):

$$H-X^3\!+\!\!L^2\!-\!X^2\!\!\left._{\!\!\!\!}\right)_{\!\!x}\!\!\underset{Z}{\overset{C}{\bigcirc}}\!\!Ar\!+\!X^1\!-\!L^1\!\!\left._{\!\!\!\!}\right)_{\!\!y}\!X^3\!-\!H \quad (1)$$

wherein Z represents a linear, branched or cyclic divalent hydrocarbon group having 2 to 30 carbon atoms; $X^1$ to $X^3$ represent any of $-CO_2-$, $-CONR^{X1}-$, $-O-$, $-NR^{X1}-$, $-S-$, $-SO_2-$, $-SO_3-$ and $-SO_2NR^{X1}-$ and may be the same as or different from each other, provided that $R^{X1}$ is a hydrogen atom or a monovalent hydrocarbon group having 1 to 30 carbon atoms; Ar represents a divalent aromatic group having 2 to 30 carbon atoms; $L^1$ and $L^2$ independently represent a divalent hydrocarbon group having 1 to 30 carbon atoms; and x and y are each independently 0 or 1.

19 Claims, No Drawings

(51) Int. Cl.
    *G03F 7/20*          (2006.01)
    *G03F 7/32*          (2006.01)

(56)           References Cited

U.S. PATENT DOCUMENTS

| | | | |
|---|---|---|---|
| 2019/0169211 A1 | 6/2019 | Urano et al. | |
| 2019/0256655 A1 | 8/2019 | Masuda et al. | |
| 2020/0041903 A1* | 2/2020 | Takemura | G03F 7/0392 |

FOREIGN PATENT DOCUMENTS

| | | | |
|---|---|---|---|
| JP | 5545746 A | 3/1980 | |
| JP | 5233344 A | 9/1993 | |
| JP | 3232022 B2 | 10/1998 | |
| JP | 2006313237 A | 11/2006 | |
| JP | 2007199653 A | 8/2007 | |
| JP | 2018158966 A | 10/2018 | |
| JP | 2019014828 A | 1/2019 | |
| TW | 201331263 A | 8/2013 | |
| TW | 201719278 A | 6/2017 | |
| TW | 201829372 A | 8/2018 | |
| WO | 2011059089 A1 | 5/2011 | |
| WO | 2020066976 A1 | 4/2020 | |

\* cited by examiner

COMPOUND, POLYIMIDE RESIN AND METHOD OF PRODUCING THE SAME, PHOTOSENSITIVE RESIN COMPOSITION, PATTERNING METHOD AND METHOD OF FORMING CURED FILM, INTERLAYER INSULATING FILM, SURFACE PROTECTIVE FILM, AND ELECTRONIC COMPONENT

JOINT RESEARCH AGREEMENT

The subject matter of this disclosure describes activities undertaken within the scope of a joint research agreement that was in place before the effective date of the instant application. The parties to the joint research agreement are International Business Machines Corporation (Armonk, N.Y., USA) and Shin-Etsu Chemical Co., Ltd. (Chiyoda-ku, Tokyo, Japan).

BACKGROUND OF THE INVENTION

Field of the Invention

The present invention relates to a compound useful as a structural unit of a polyimide resin, a polyimide resin prepared by using such a compound and a method of producing the same, a positive photosensitive resin composition or negative photosensitive resin composition using aforementioned polyimide resin as a base resin, a patterning method using these compositions that can be developed with an aqueous alkaline solution, and a method of forming a cured film. In addition, the present invention also relates to an interlayer insulating film, surface protective film and electronic component using this cured film.

Description of the Related Art

As various electronic devices such as personal computers, digital cameras and mobile phones progress toward miniaturization and high performance, demands for further miniaturization, thinning and densification are being rapidly increased also in semiconductor elements. Therefore, it has been desired to develop a photosensitive insulating material that can cope with increase in the area of substrate for improvement in productivity, and can also form a fine pattern with a high aspect ratio on a substrate in the high density packaging technology such as chip size package or chip scale package (CSP), or three-dimensional lamination.

In the high density packaging technology such as three-dimensional lamination, for a photosensitive insulating material that can form a pattern on a substrate, a polyimide-based material or a polybenzoxazole-based material has been utilized as a protective film or an insulating layer, and its insulating property, heat resistance, excellent mechanical properties such as high extensibility and high strength, adhesiveness to a substrate and the like have attracted attention continuously, and even now, development thereof has been carried on highly actively.

Conventionally, as a photosensitive polyimide-based material, materials utilizing a polyamic acid, which is a precursor of polyimide, for example, materials in which photosensitive groups are introduced into carboxyl groups of a polyamic acid by ester bonds have been proposed (Japanese Patent Laid-Open No. 49-115541 and Japanese Patent Laid-Open No. 55-45746). In these proposals, after the formation of a patterned film, imidization at a high temperature exceeding 300° C. is indispensable in order to obtain the target polyimide film.

However, in recent years, due to demands for reduction in thermal load to the device, reduction in stress to the substrate and the like, a polyimide-based material or polybenzoxazole-based material has been required that can be cured at a low temperature of 250° C. or lower, and further preferably 200° C. or lower.

As a resin composition that can be cured at low temperature, a photosensitive polyimide resin composition using a solvent-soluble imidized resin has been proposed (Japanese Patent No. 3232022). In Japanese Patent No. 3232022, development of a negative photosensitive resin composition containing the polyimide with N-methyl-2-pyrrolidone (NMP) is performed in patterning, but the resolution performance in the patterning is not described specifically.

As a polyimide material excellent in heat resistance and mechanical properties such as tensile strength, a variety of materials have been known that comprise an aromatic substituent having a rigid planar structure in the structure of resin (Japanese Patent No. 5233344). These materials not only have very high glass transition points, but also hardly exhibit weight loss under high temperature conditions, and have excellent tensile strengths as well, and therefore, they have been widely used for a variety of heat resisting, abrasion resisting, and insulating material applications. On the other hand, such polyimide resins have poor solubilities in organic solvents, and thus require amide-based solvents such as NMP, which have excellent dissolving power, as a solvent upon the application. However, such solvents have been the object of environmental regulations in recent years due to their high toxicities, and it has been thus required to replace them with solvents with much lower toxicities.

Furthermore, when it is attempted to apply such a substituent to lithography materials, the solubility of the polyimide resin in an aqueous alkaline solution is remarkably decreased, and therefore, lithography performance may be significantly impaired, particularly in positive tone lithography. In addition, it is also inevitable that lithography performance is impaired in negative tone lithography due to the above-mentioned low organic solvent solubility.

Considering the above circumstances, when a rigid aromatic substituent is introduced into a litho-patternable polyimide material to improve mechanical properties, a design to ensure solubilities in an organic solvent and aqueous alkaline solution is essential.

As a polyimide material with improved organic solvent solubility, those into which the 9,9-diphenylfluorene skeleton is introduced have been known (International Publication No. WO 2019/151336). The 9,9-diphenylfluorene skeleton is said to, while having the fluorene structure with high planarity, exhibit good solubility in organic solvents in spite of high aromatic ring density owing to properties that the substituents are oriented in directions perpendicular to the conjugate plane (cardo structure), and in this literature, performance evaluation is performed using a single solvent of γ-butyrolactone as a solvent upon the application. On the other hand, γ-butyrolactone is, while having high dissolving power, known to be likely to cause poor application due to its high surface tension, and in the above-described literature, there is no sufficient description with regard to the solubility of the polyimide resin in propylene glycol monomethyl ether acetate (PGMEA), which has less solvency compared to γ-butyrolactone but is said to be more desirable from the viewpoint of coating property.

Furthermore, a polyimide resin having the 1,1-diphenyl-cyclohexane structure as a structural unit comprising a cardo structure has also been known (Japanese Patent Laid-Open No. 2019-14828). This structural unit has lower aromatic density compared to the above-mentioned fluorene structure and has an alicyclic structure excellent in solubility, and therefore, that polyimide resin is expected to exhibit higher solvent solubility. On the other hand, it is known to have heat resistance and mechanical strength inferior to those of a polyimide resin having high aromatic density.

As stated above, in association with densification and integration of chips, fining of patterns in the rewiring technology for insulating protective films is expected to progress more and more in the future, and therefore, a photosensitive resin composition using a polyimide resin has been strongly desired, wherein the composition can realize high resolution without impairing excellent characteristics such as patterns of the polyimide obtained through heating, and mechanical properties, in particular strength, and adhesiveness of the protective film.

In addition, it has also been strongly desired that insulating protective films that have been subjected to patterning and curing possess heat resistance in a variety of processes and resistance to a variety of chemicals to be used.

That is, rapid development of photosensitive resin compositions possessing all of these characteristics with no lack has been desired.

The present invention has been made in view of the above-described circumstances, and an object thereof is to provide a compound to produce a polyimide that can be used as a base resin for a photosensitive resin composition, wherein the photosensitive resin composition can form a fine pattern and can achieve high resolution without impairing excellent characteristics such as mechanical strength and extensibility; a polyimide resin obtained by using such a compound; and a method of producing the same. In addition, another object of the present invention is to provide a positive photosensitive resin composition and a negative photosensitive resin composition using the above-described polyimide resin, wherein, upon patterning, the positive photosensitive resin composition and the negative photosensitive resin composition are soluble in an aqueous alkaline solution, are excellent in resolution, and can form a fine pattern.

SUMMARY OF THE INVENTION

In order to solve the problems described above, the present invention provides a compound represented by the following general formula (1):

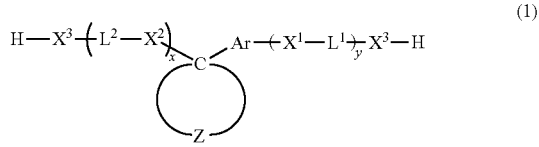

(1)

wherein Z represents a linear, branched or cyclic divalent hydrocarbon group having 2 to 30 carbon atoms that is optionally substituted with a heteroatom and optionally has an intervening heteroatom; $X^1$ to $X^3$ represent any of —$CO_2$—, —$CONR^{X1}$—, —O—, —$NR^{X1}$—, —S—, —$SO_2$—, —$SO_3$— and —$SO_2NR^{X1}$— and may be the same as or different from each other, provided that $R^{X1}$ is a hydrogen atom or a monovalent hydrocarbon group having 1 to 30 carbon atoms that is optionally substituted with a heteroatom and optionally has an intervening heteroatom; Ar represents a divalent aromatic group having 2 to 30 carbon atoms that is optionally substituted with a heteroatom and optionally has an intervening heteroatom; $L^1$ and $L^2$ independently represent a divalent hydrocarbon group having 1 to 30 carbon atoms that is optionally substituted with a heteroatom and optionally has an intervening heteroatom; and x and y are each independently 0 or 1.

Such a compound can produce a polyimide that can be used as a base resin for a photosensitive resin composition, wherein the photosensitive resin composition can form a pattern without impairing excellent characteristics such as mechanical strength and extensibility.

In this case, $X^3$ in general formula (1) can be any of —$CO_2$—, —$NR^{X1}$— and —O—.

Such $X^3$ is a condensation linking group frequently used for general polycondensation polymers and is desirable.

In addition, in the above-described compound, it is desirable that x and y in general formula (1) be 0 from the viewpoint of ease of synthesis and availability of raw materials.

Further, the present invention provides a resin comprising structural units represented by the following general formulas (2) and (3):

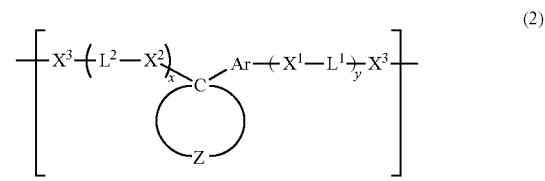

(2)

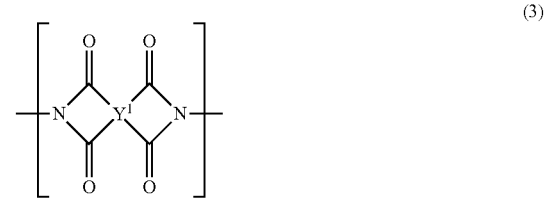

(3)

wherein Z represents a linear, branched or cyclic divalent hydrocarbon group having 2 to 30 carbon atoms that is optionally substituted with a heteroatom and optionally has an intervening heteroatom; $X^1$ to $X^3$ represent any of —$CO_2$—, —$CONR^{X1}$—, —O—, —$NR^{X1}$—, —S—, —$SO_2$—, —$SO_3$— and —$SO_2NR^{X1}$— and may be the same as or different from each other, provided that $R^{X1}$ is a hydrogen atom or a monovalent hydrocarbon group having 1 to 30 carbon atoms that is optionally substituted with a heteroatom and optionally has an intervening heteroatom; Ar represents a divalent aromatic group having 2 to 30 carbon atoms that is optionally substituted with a heteroatom and optionally has an intervening heteroatom; $L^1$ and $L^2$ independently represent a divalent hydrocarbon group having 1 to 30 carbon atoms that is optionally substituted with a heteroatom and optionally has an intervening heteroatom; x and y are each independently 0 or 1; and $Y^1$ represents a tetravalent hydrocarbon group having 1 to 100 carbon atoms that is optionally substituted with a heteroatom and optionally has an intervening heteroatom.

Such a resin can be used as a base resin for a photosensitive resin composition, wherein the photosensitive resin composition can form a pattern without impairing excellent characteristics such as mechanical strength and extensibility.

In this case, it is preferable that the resin further comprise, in addition to the structural units (2) and (3), a structural unit represented by the following general formula (4):

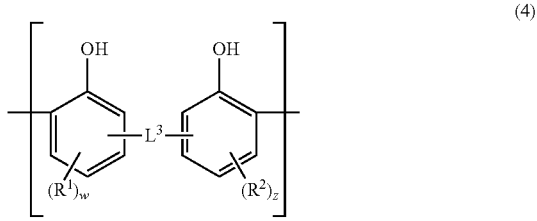

(4)

wherein $L^3$ is a single bond or a divalent linking group; $R^1$ to $R^2$ each independently represent any monovalent substituent; and w and z are 0 to 3, and when they are 2 or more, substituents represented by a plurality of $R^1$ and $R^2$ may be the same as or different from each other.

A resin comprising such a structural unit is soluble in a basic aqueous solution and a basic organic solvent due to the effect of acidic hydroxy groups of the phenol units, and therefore, by adding a photosensitive or radiation sensitive additive and a dissolution controlling agent, the water solubility and the organic solvent solubility can be controlled, and as a result, patterning by lithography can be suitably performed.

In this case, it is preferable that $L^3$ in general formula (4) be —$CR^{f1}R^{f2}$— or —$SO_2$—, provided that $R^{f1}$ to $R^{f2}$ are each independently a fluorine atom or a fluoroalkyl group having 1 to 10 carbon atoms.

In such a resin, the acidity of the phenolic hydroxy groups become higher and the solubility in a basic aqueous solution and a basic organic solvent is further improved, which is suitable for application to lithography.

The present invention also provides a method of producing the above-described resin, wherein the above-described compound, or an acid halide or acid anhydride derived therefrom is reacted with the following formula (5) and at least one of compounds represented by the following general formulas (6) to (7):

 (5)

 (6)

 (7)

wherein $Y^1$ is defined as above; $Y^2$ represents a divalent hydrocarbon group having 1 to 100 carbon atoms that is optionally substituted with a heteroatom and optionally has an intervening heteroatom; and $X^4$ represents any of a hydroxy group, a fluorine atom, a chlorine atom, a bromine atom, an iodine atom, —$OCO_2R^{X4}$, —$OSO_2R^{X4}$ and —$OSO_3R^{X4}$, provided that $R^{X4}$ is a monovalent hydrocarbon group having 1 to 10 carbon atoms that is optionally substituted with a heteroatom and optionally has an intervening heteroatom.

Such a method of producing the resin can suitably produce a base resin for a photosensitive resin composition, wherein the photosensitive resin composition can form a pattern without impairing excellent characteristics such as mechanical strength and extensibility.

Furthermore, the present invention provides a positive photosensitive resin composition comprising: (A) the above-described resin; (B) a photosensitizer that generates an acid by light to increase the dissolution rate in an aqueous alkaline solution, and that is a compound having a quinonediazide structure; and (D) a solvent.

Moreover, the present invention provides a positive photosensitive resin composition further comprising, in addition to the above, (C) at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'):

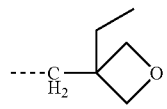 (C-1)

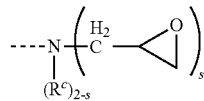 (C-2)

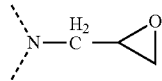 (C-2')

wherein the dotted line represents a bond; $R^c$ represents a linear, branched or cyclic alkyl group having 1 to 6 carbon atoms; and s is 1 or 2.

In such a positive photosensitive resin composition, by using the photosensitizer of component (B), upon patterning, the exposed part becomes soluble because its dissolution rate in a developing solution of an aqueous alkaline solution is accelerated, and the unexposed part is not dissolved due to the alkaline dissolution prevention by the above-described photosensitizer, and therefore, a suitable positive image can be obtained.

The present invention also provides a negative photosensitive resin composition comprising: (A') the above-described resin; (B') a photoacid generator; (C') at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'); and (D) a solvent:

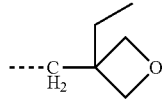
(C-1)

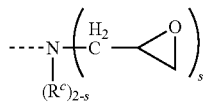
(C-2)

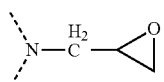
(C-2')

wherein the dotted line represents a bond; $R^c$ represents a linear, branched or cyclic alkyl group having 1 to 6 carbon atoms; and s is 1 or 2.

Such a negative photosensitive resin composition can, by using the photoacid generator of component (B'), provide a suitable negative image upon patterning.

In addition, the present invention provides a patterning method comprising:

(1) applying the above-described positive photosensitive resin composition mentioned above onto a substrate to form a photosensitive material film;

(2) heating the photosensitive material film;

(3) exposing the photosensitive material film with a high energy beam having a wavelength of 190 to 500 nm or an electron beam through a photomask; and (4) developing the film with a developing solution of an aqueous alkaline solution.

As stated above, in the positive photosensitive resin composition according to the present invention, alkaline development with an aqueous alkaline solution is applicable.

In addition, the present invention provides a patterning method comprising:

(I) applying the above-described negative photosensitive resin composition onto a substrate to form a photosensitive material film;

(II) heating the photosensitive material film;

(III) exposing the photosensitive material film with a high energy beam having a wavelength of 190 to 500 nm or an electron beam through a photomask; and (IV) developing the film with a developing solution of an aqueous alkaline solution.

As stated above, in the negative photosensitive resin composition according to the present invention, alkaline development with an aqueous alkaline solution is also possible.

In this case, it is preferable that the patterning method comprise a post-exposure heating between the exposure (III) and the development (IV).

As stated above, when the heating after the exposure (post-exposure bake (PEB)) is included, crosslinking reaction between the crosslinking agent and the polymer can be accelerated.

Furthermore, the present invention provides a method of forming a cured film, comprising heating and post-curing a patterned film obtained by the patterning methods mentioned above at a temperature of 100 to 300° C.

By the method of forming a cured film according to the present invention, the crosslinking density of the film of the photosensitive resin composition can be increased and the remaining volatile components can be removed, improving adhesiveness to the substrate or the like, heat resistance and strength, as well as electrical properties, preferably.

In addition, the present invention provides an interlayer insulating film comprising a cured film formed by curing the positive photosensitive resin composition mentioned above or the negative photosensitive resin composition mentioned above.

Such an interlayer insulating film according to the present invention exhibits excellent adhesiveness while maintaining excellent insulating property, and can also significantly improve resolution performance for realizing further fine patterning while maintaining mechanical strength suitable as a protective film.

In addition, the present invention provides a surface protective film comprising a cured film formed by curing the above-described positive photosensitive resin composition or the above-described negative photosensitive resin composition.

Such a surface protective film according to the present invention is excellent in adhesiveness to the substrate or the like, heat resistance, electrical properties, mechanical strength, and the like.

In addition, the present invention provides an electronic component having the above-described interlayer insulating film or the above-described surface protective film.

Such an electronic component according to the present invention has the above-described interlayer insulating film or the above-described surface protective film, and is thus excellent in reliability.

Advantageous Effects of Invention

As described above, the compound according to the present invention can be produce a polyimide that can be used as a base resin for a photosensitive resin composition, wherein the photosensitive resin composition can form a fine pattern and can achieve high resolution without impairing excellent characteristics such as mechanical strength and extensibility. In addition, a polyimide resin obtained by using such a compound can provide a positive photosensitive resin composition and a negative photosensitive resin composition, wherein, upon patterning, the positive photosensitive resin composition and the negative photosensitive resin composition are soluble in an aqueous alkaline solution, are excellent in resolution, and can form a fine pattern.

In particular, the compound according to the present invention has a main skeleton having a cyclic structure, as well as a condensation linking group and an aromatic substituent having a condensation linking group, both of which extend from the main skeleton in a cardo-like manner, and when the compound is used as a raw material for a variety of polycondensation polymers, the tensile strength and extensibility can be improved through improvements in Tg and in tensile strength due to the tertiary condensation linking group with a low degree of freedom for structural deformation and through stacking interaction of the aromatic linking group. Furthermore, due to an improved solubility in organic solvents by the cardo structure, the compound has high solubility in a variety of organic solvents.

Furthermore, a cured film obtained from the positive photosensitive resin composition or negative photosensitive resin composition according to the present invention acts as a protective film excellent in mechanical strength, adhesiveness to the substrate, electrical properties, reliability and solvent solubility due to the structure originating from the compound.

DETAILED DESCRIPTION OF THE PREFERRED EMBODIMENTS

As mentioned above, development of a polyimide resin has been required that can be used as a base resin for a photosensitive resin composition, wherein the photosensitive resin composition can form a pattern without impairing excellent characteristics such as mechanical strength and extensibility.

As a result of inventors' intensive studies to achieve the object described above, the present invention provides that, when a polyimide resin obtained by using a compound represented by the following general formula (1) is used as a base resin for a photosensitive resin composition, such a polyimide resin can be utilized for either a positive photosensitive resin composition that allows development with an aqueous alkaline solution or a negative photosensitive resin composition that allows development with an aqueous alkaline solution because the polyimide resin is soluble in a developing solution of an aqueous alkaline solution, and that a pattern obtained by using these photosensitive resin compositions is excellent in mechanical strength, extensibility and the like.

Furthermore, the present invention provides that a protective film is excellent in electrical properties, mechanical properties and adhesiveness, wherein the protective film is obtained by using a photosensitive resin composition comprising the above-described polyimide resin as a base resin, and by subjecting the composition to patterning and heating. That is, the obtained cured film having a pattern formed by using the photosensitive resin composition comprising the above-described polyimide resin as a base resin is excellent as a protective film for electrical and electronic components and as an insulating protective film. Note that, in the specification, electrical and electronic components are altogether referred to as "electronic components".

The present invention relates to a compound represented by general formula (1), which will be mentioned later, and a resin comprising the same as a structural unit thereof.

Hereinafter, the present invention will be described in detail, but the present invention is not limited to the description below.

The present invention provides a compound represented by the following general formula (1):

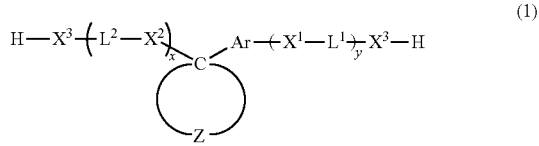

(1)

wherein Z represents a linear, branched or cyclic divalent hydrocarbon group having 2 to 30 carbon atoms that is optionally substituted with a heteroatom and optionally has an intervening heteroatom; $X^1$ to $X^3$ represent any of $-CO_2-$, $-CONR^{X1}-$, $-O-$, $-NR^{X1}-$, $-S-$, $-SO_2-$, $-SO_3-$ and $-SO_2NR^{X1}-$ and may be the same as or different from each other, provided that $R^{X1}$ is a hydrogen atom or a monovalent hydrocarbon group having 1 to 30 carbon atoms that is optionally substituted with a heteroatom and optionally has an intervening heteroatom; Ar represents a divalent aromatic group having 2 to 30 carbon atoms that is optionally substituted with a heteroatom and optionally has an intervening heteroatom; $L^1$ and $L^2$ independently represent a divalent hydrocarbon group having 1 to 30 carbon atoms that is optionally substituted with a heteroatom and optionally has an intervening heteroatom; and x and y are each independently 0 or 1.

In formula (1), Z represents a linear, branched or cyclic divalent hydrocarbon group having 2 to 30 carbon atoms that is optionally substituted with a heteroatom and optionally has an intervening heteroatom.

The divalent hydrocarbon group represented by Z may be any of linear, branched and cyclic, and specific examples thereof include linear or branched, saturated or unsaturated hydrocarbon groups such as an ethylene group, a propane-1,2-diyl group, a propane-1,3-diyl group, a butane-1,2-diyl group, a butane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, a vinylene group, a propene-1,2-diyl group and a propene-1,3-diyl group; saturated or unsaturated cyclic hydrocarbon groups such as a cyclopropane-1,2-diyl group, a cyclobutane-1,2-diyl group, a cyclopentane-1,2-diyl group, a cyclopentane-1,3-diyl group, a cyclohexane-1,2-diyl group, a cyclohexane-1,3-diyl group, a cyclohexane-1,4-diyl group, a cycloheptane-1,2-diyl group, a cycloheptane-1,3-diyl group, a cycloheptane-1,4-diyl group, a cyclooctane-1,2-diyl group, a cyclooctane-1,3-diyl group, a cyclooctane-1,4-diyl group, a cyclooctane-1,5-diyl group, a cyclononane-1,2-diyl group, a cyclononane-1,3-diyl group, a cyclononane-1,4-diyl group, a cyclononane-1,5-diyl group, a cyclodecane-1,2-diyl group, a cyclodecane-1,3-diyl group, a cyclodecane-1,4-diyl group, a cyclodecane-1,5-diyl group, a cyclodecane-1,6-diyl group, a norbornane-1,2-diyl group, a norbornane-1,3-diyl group, a norbornane-1,4-diyl group, a norbornane-2,3-diyl group, a norbornane-2,5-diyl group, a norbornane-2,6-diyl group, a norbornane-2,7-diyl group, a benzene-1,2-diyl group, a naphthalene-1,2-diyl group, a biphenyl-2,2'-diyl group, a cyclopentene-1,2-diyl group, a cyclohexene-1,2-diyl group, a cycloheptene-1,2-diyl group and a cyclooctene-1,2-diyl group; the above-described linear, branched or cyclic hydrocarbon group and a methylene group; and divalent substituents formed by combining any two or more groups among divalent gem-hydrocarbon groups such as an ethane-1,1-diyl group, a propane-1,1-diyl group, a butane-1,1-diyl group, a pentane-1,1-diyl group, a hexane-1,1-diyl group, a heptane-1,1-diyl group, an octane-1,1-diyl group, a nonane-1,1-diyl group, a decane-1,1-diyl group, a cyclopropane-1,1-diyl group, a cyclobutane-1,1-diyl group, a cyclopentane-1,1-diyl group, a cyclohexane-1,1-diyl group, a cycloheptane-1,1-diyl group, a cyclooctane-1,1-diyl group, a vinylidene group and a propene-1,1-diyl group.

Furthermore, in the divalent hydrocarbon group, part or all of hydrogen atoms therein may be replaced with a substituent comprising a heteroatom such as an oxygen atom, a sulfur atom, a nitrogen atom and a halogen atom, and as a result, the divalent hydrocarbon group may comprise a hydroxy group, an amino group, a cyano group, a nitro group, a haloalkyl group or the like.

And, in the divalent hydrocarbon group, one or more of the carbon atoms therein may be replaced with a substituent comprising a heteroatom such as an oxygen atom, a sulfur atom and a nitrogen atom, and as a result, the divalent hydrocarbon group may comprise an ether bond, a sulfide bond, a carbonyl group, an ester bond, —N(R)— (wherein R is a hydrogen atom or a monovalent hydrocarbon group having 1 to 30 carbon atoms that is optionally substituted with a heteroatom and optionally has an intervening heteroatom), an amide bond, an imino bond, a sulfonyl group, a sulfinyl group, a sulfonate ester group, a sulfonamide bond, a carbonate bond, a carbamate bond, a carboxylic anhydride (—C(=O)—O—C(=O)—) or the like.

The monovalent hydrocarbon group represented by R may be any of linear, branched and cyclic. Specific examples thereof include alkyl groups such as a methyl group, an ethyl group, a n-propyl group, an isopropyl group, a n-butyl group, a sec-butyl group, an isobutyl group, a tert-butyl group, a cyclopropyl group, a cyclopentyl group, a cyclohexyl group, a cyclopropylmethyl group, a 4-methylcyclohexyl group, a cyclohexylmethyl group, a norbornyl group and an adamantyl group; alkenyl groups such as a vinyl group, an allyl group, a propenyl group, a butenyl group, a hexenyl group and a cyclohexenyl group; alkynyl groups such as an ethynyl group, a butynyl group, a 2-cyclohexylethynyl group, a 2-phenylethynyl group; aryl groups such as a phenyl group, a naphthyl group and a thienyl group; aralkyl groups such as a benzyl group, a 1-phenylethyl group and a 2-phenylethyl group; and aracyl groups such as a benzoylmethyl group and a 1-benzoylethyl group.

Further, in the monovalent hydrocarbon group, part or all of hydrogen atoms therein may be replaced with a substituent comprising a heteroatom such as an oxygen atom, a sulfur atom, a nitrogen atom and a halogen atom, and as a result, the monovalent hydrocarbon group may comprise a hydroxy group, an amino group, a cyano group, a nitro group, a haloalkyl group or the like.

And, in the monovalent hydrocarbon group, one or more of the carbon atoms therein may be replaced with a substituent comprising a heteroatom such as an oxygen atom, a sulfur atom and a nitrogen atom, and as a result, the monovalent hydrocarbon group may comprise an ether bond, a sulfide bond, a carbonyl group, an ester bond, —N(R)— (wherein R is a hydrogen atom or a monovalent hydrocarbon group having 1 to 30 carbon atoms that is optionally substituted with a heteroatom and optionally has an intervening heteroatom), an amide bond, an imino bond, a sulfonyl group, a sulfinyl group, a sulfonate ester group, a sulfonamide bond, a carbonate bond, a carbamate bond, a carboxylic anhydride (—C(=O)—O—C(=O)—) or the like.

In formula (1), as the substituent represented by Z, particularly suitable are those shown below, provided that -* represents an attachment point. Note that the present invention is not limited to them.

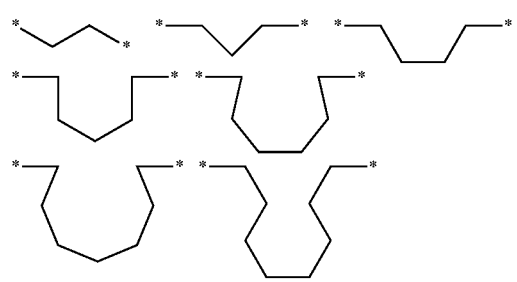

-continued

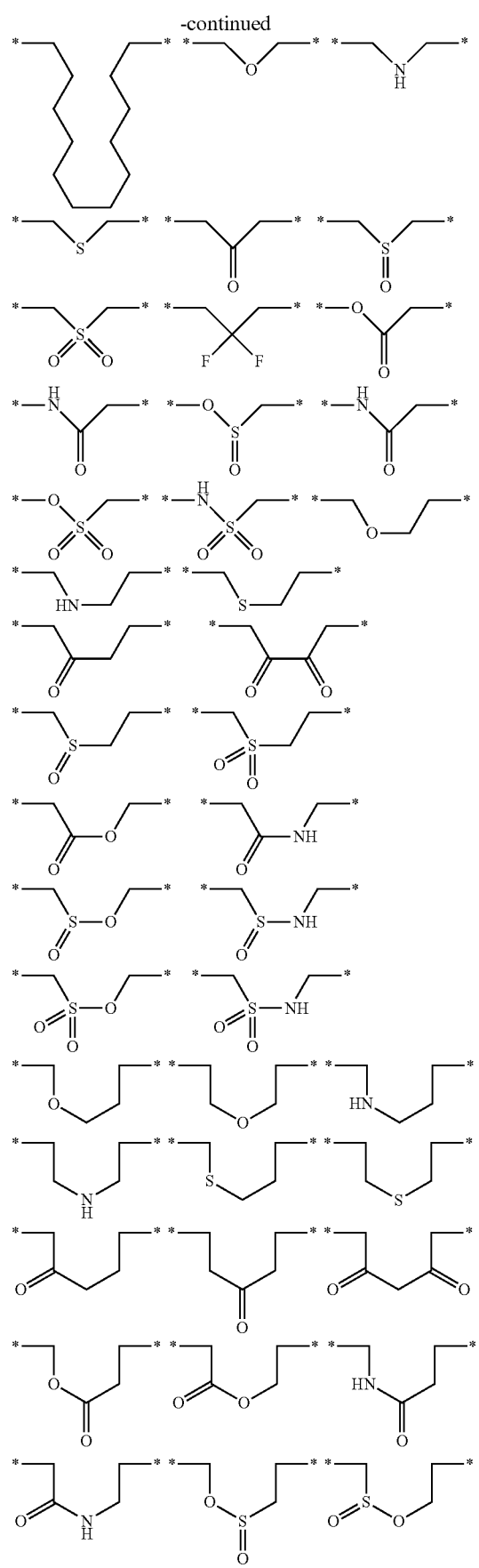

-continued

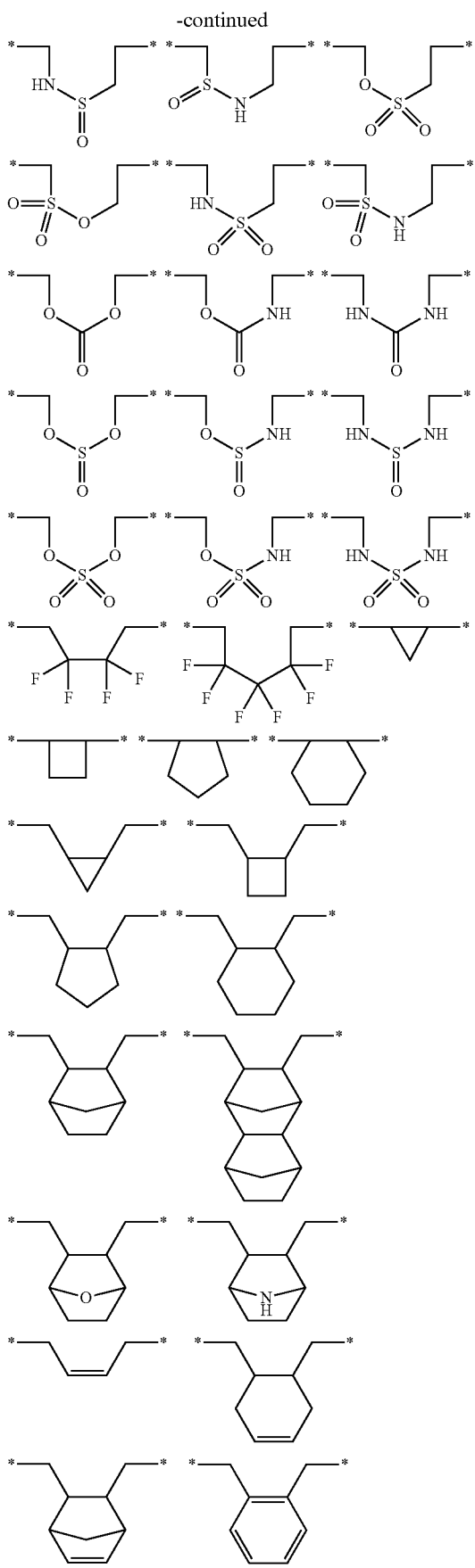

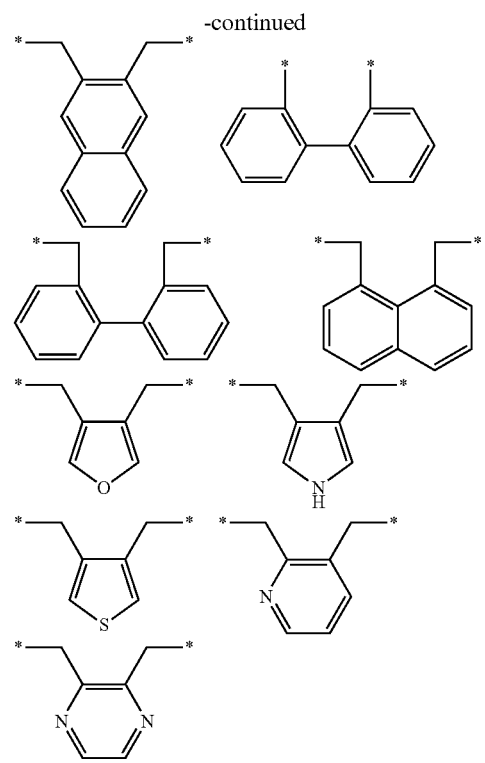

In formula (1), $X^1$ to $X^3$ represent any of —$CO_2$—, —$CONR^{X1}$—, —O—, —$NR^{X1}$—, —S—, —$SO_2$—, —$SO_3$— and —$SO_2NR^{X1}$— and may be the same or different. In the formula, $R^{X1}$ represents a hydrogen atom or a monovalent hydrocarbon group optionally substituted with a heteroatom and optionally having an intervening heteroatom that is the same as recited above, which has 1 to 30 carbon atoms.

In formula (1), Ar represents a divalent aromatic group having 2 to 30 carbon atoms that is optionally substituted with a heteroatom and optionally has an intervening heteroatom. Specific examples thereof include an o-phenylene group, a m-phenylene group, a p-phenylene group, an o-naphthylene group, a m-naphthylene group, a p-naphthylene group, an ana-naphthylene group, an epi-naphthylene group, a kata-naphthylene group, a peri-naphthylene group, a pros-naphthylene group, an amphi-naphthylene group, and a naphthalene-2,7-diyl group.

Further, in the divalent aromatic group, part or all of hydrogen atoms therein may be replaced with a monovalent hydrocarbon group that is defined as above.

And, in the divalent aromatic group, part or all of hydrogen atoms therein may be replaced with a substituent comprising a heteroatom such as an oxygen atom, a sulfur atom, a nitrogen atom and a halogen atom, and as a result, the divalent aromatic group may comprise a hydroxy group, an amino group, a cyano group, a nitro group, a haloalkyl group or the like.

Furthermore, in the divalent aromatic group, one or more of the carbon atoms therein may be replaced with a substituent comprising a heteroatom such as an oxygen atom, a sulfur atom and a nitrogen atom, and as a result, the divalent aromatic group may comprise an ether bond, a sulfide bond, a carbonyl group, an ester bond, —N(R)— (wherein R is a hydrogen atom or a monovalent hydrocarbon group having 1 to 30 carbon atoms that is optionally substituted with a heteroatom and optionally has an intervening heteroatom), an amide bond, an imino bond, a sulfonyl group, a sulfinyl group, a sulfonate ester group, a sulfonamide bond, a carbonate bond, a carbamate bond, a carboxylic anhydride (—C(=O)—O—C(=O)—) or the like.

In formula (1), as the substituent represented by Ar, particularly suitable are those shown below, provided that -* represents an attachment point. Note that the present invention is not limited to them.

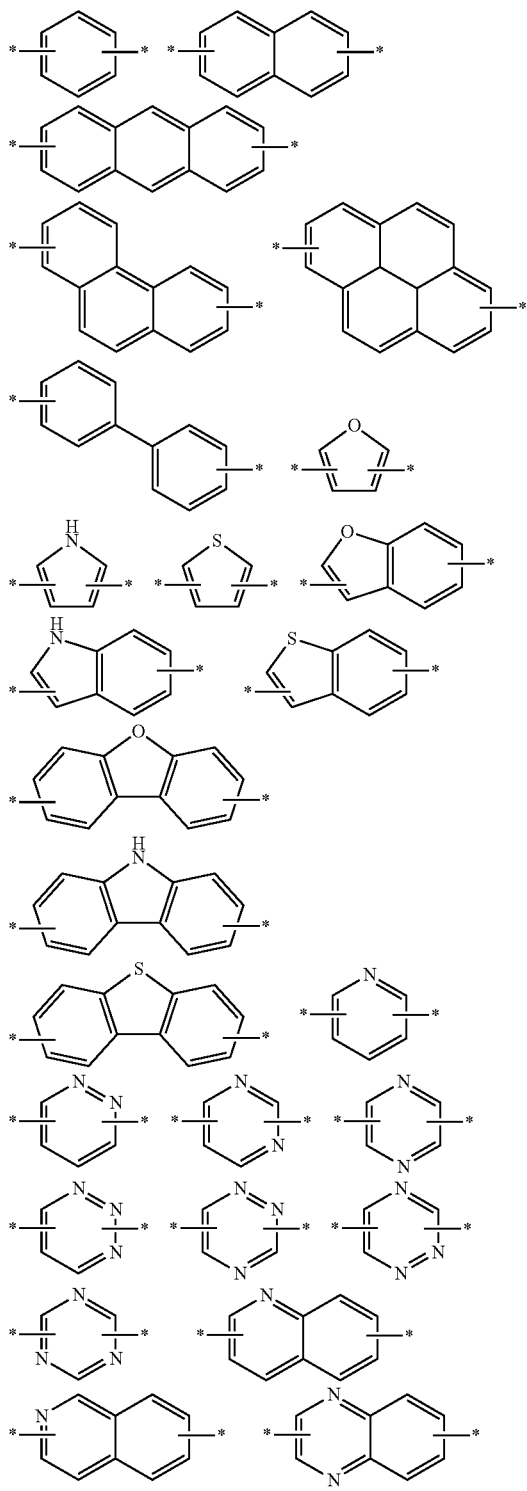

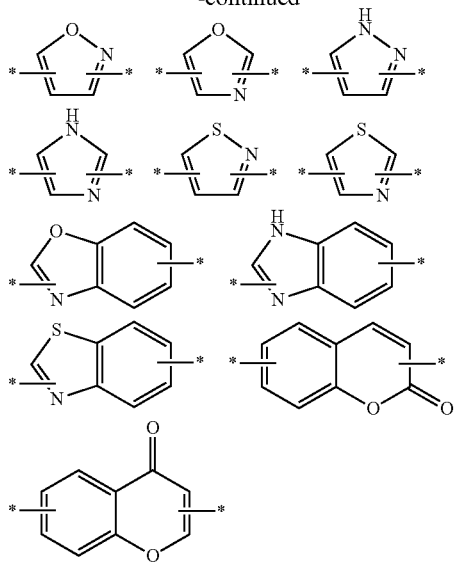

In formula (1), $L^1$ and $L^2$ independently represent a divalent hydrocarbon group having 1 to 30 carbon atoms that is optionally substituted with a heteroatom and optionally has an intervening heteroatom; x and y are each independently 0 or 1. Specific examples thereof include linear or branched, saturated or unsaturated hydrocarbon groups such as an ethylene group, a propane-1,2-diyl group, a propane-1,3-diyl group, a butane-1,2-diyl group, a butane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, a vinylene group, a propene-1,2-diyl group and a propene-1,3-diyl group; saturated or unsaturated cyclic hydrocarbon groups such as a cyclopropane-1,2-diyl group, a cyclobutane-1,2-diyl group, a cyclopentane-1,2-diyl group, a cyclopentane-1,3-diyl group, a cyclohexane-1,2-diyl group, a cyclohexane-1,3-diyl group, a cyclohexane-1,4-diyl group, a cycloheptane-1,2-diyl group, a cycloheptane-1,3-diyl group, a cycloheptane-1,4-diyl group, a cyclooctane-1,2-diyl group, a cyclooctane-1,3-diyl group, a cyclooctane-1,4-diyl group, a cyclooctane-1,5-diyl group, a cyclononane-1,2-diyl group, a cyclononane-1,3-diyl group, a cyclononane-1,4-diyl group, a cyclononane-1,5-diyl group, a cyclodecane-1,2-diyl group, a cyclodecane-1,3-diyl group, a cyclodecane-1,4-diyl group, a cyclodecane-1,5-diyl group, a cyclodecane-1,6-diyl group, a norbornane-1,2-diyl group, a norbornane-1,3-diyl group, a norbornane-1,4-diyl group, a norbornane-2,3-diyl group, a norbornane-2,5-diyl group, a norbornane-2,6-diyl group, a norbornane-2,7-diyl group, a benzene-1,2-diyl group, a naphthalene-1,2-diyl group, a biphenyl-2,2'-diyl group, a cyclopentene-1,2-diyl group, a cyclohexene-1,2-diyl group, a cycloheptene-1,2-diyl group and a cyclooctene-1,2-diyl group; and divalent gem-hydrocarbon groups such as an ethane-1,1-diyl group, a propane-1,1-diyl group, a propane-2,2-diyl group, a butane-1,1-diyl group, a pentane-1,1-diyl group, a hexane-1,1-diyl group, a heptane-1,1-diyl group, an octane-1,1-diyl group, a nonane-1,1-diyl group, a decane-1,1-diyl group, a cyclopropane-1,1-diyl group, a cyclobutane-1,1-diyl group, a cyclopentane-1,1- diyl group, a cyclohexane-1,1-diyl group, a cycloheptane-1,1-diyl group, a cyclooctane-1,1-diyl group, a vinylidene group and a propene-1,1-diyl group.

When such a compound is applied as a structural unit of a resin, improvement in Tg, tensile strength and extensibility, as well as high solubility in a variety of organic solvents, are achieved.

Moreover, upon this, it is desirable that $X^3$ in general formula (1) be a condensation linking group frequently used for general polycondensation polymers, and in particular, any of —$CO_2$—, —$NR^{X1}$— and —O—, provided that $R^{X1}$ is defined as above.

In formula (1), as the substituents represented by $L^1$ and $L^2$, particularly suitable are those shown below, provided that -* represents an attachment point. Note that the present invention is not limited to them.

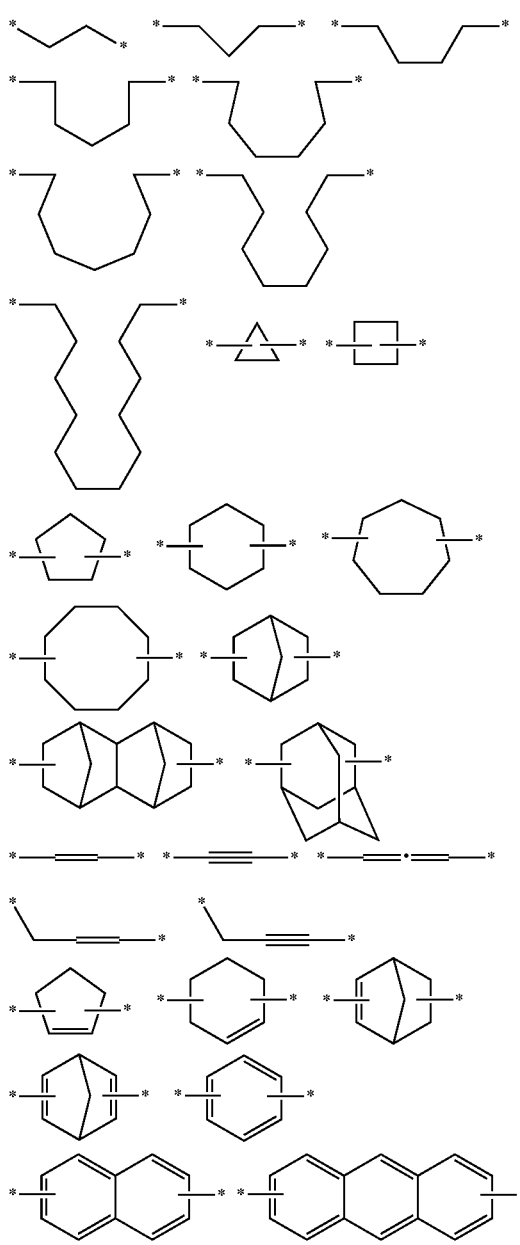

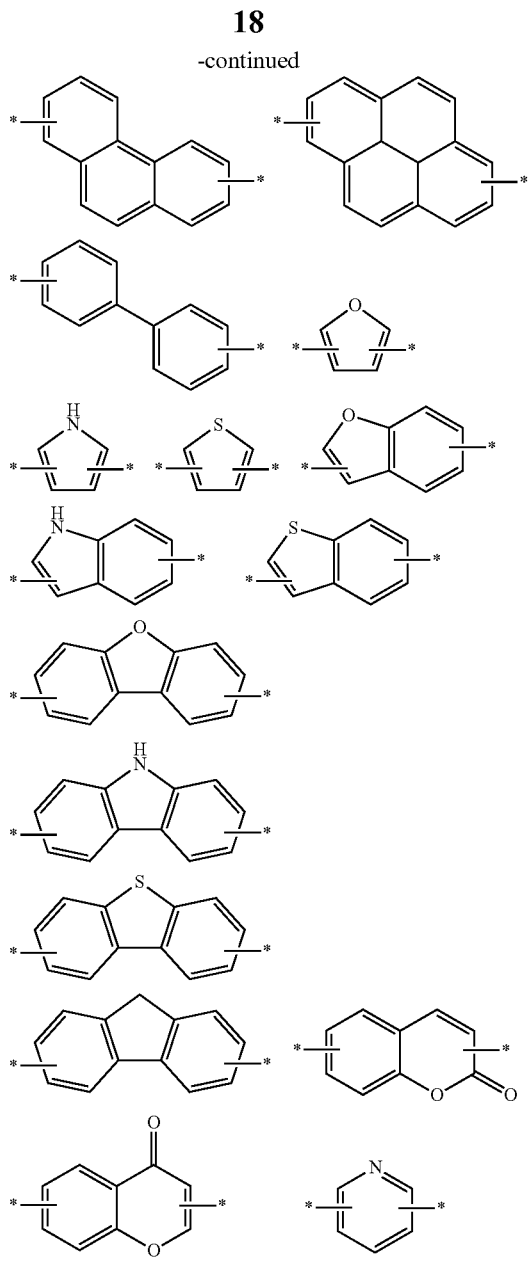

Furthermore, it is desirable that x and y in general formula (1) be 0 from the viewpoint of ease of synthesis and availability of raw materials.

In addition, the present invention provides a resin comprising the above-described compound as a structural unit, and as the one providing particularly excellent physical properties, the present invention provides a resin that comprises structural units represented by the following general formulas (2) and (3):

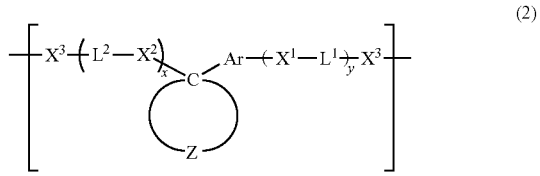

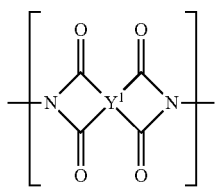

(3)

wherein Z, $X^1$ to $X^3$, Ar, $L^1$ and $L^2$, x and y are defined as above; and $Y^1$ represents a tetravalent hydrocarbon group having 1 to 100 carbon atoms that is optionally substituted with a heteroatom and optionally has an intervening heteroatom.

In formula (3), $Y^1$ represents a tetravalent hydrocarbon group having 1 to 100 carbon atoms that is optionally substituted with a heteroatom and optionally has an intervening heteroatom. Specific examples thereof include tetravalent linear saturated hydrocarbon groups such as an ethane-1,1,1,2-tetrayl group, an ethane-1,1,2,2-tetrayl group, a propane-1,1,1,2-tetrayl group, a propane-1,1,2,2-tetrayl group, a propane-1,1,1,3-tetrayl group, a propane-1,1,2,3-tetrayl group, a propane-1,1,3,3-tetrayl group, a propane-1,2,2,3-tetrayl group, a butane-1,2,3,4-tetrayl group, a pentane-1,2,4,5-tetrayl group, a hexane-1,2,5,6-tetrayl group, a heptane-1,2,6,7-tetrayl group and an octane-1,2,7,8-tetrayl group; tetravalent branched saturated hydrocarbon groups such as a 2-methylpropane-1,1,1,2-tetrayl group, a 2-methylpropane-1,1,2,3-tetrayl group, a 2-methylpropane-1,1,3,3-tetrayl group, a 2,3-dimethylbutane-1,2,3,4-tetrayl group, a 3-methylpentane-1,2,4,5-tetrayl group and a 3-methylhexane-1,2,5,6-tetrayl group; tetravalent cyclic saturated hydrocarbon groups such as a cyclopropane-1,1,2,2-tetrayl group, a cyclobutane-1,1,2,2-tetrayl group, a cyclobutane-1,1,2,3-tetrayl group, a cyclobutane-1,1,2,4-tetrayl group, a cyclobutane-1,1,3,3-tetrayl group, a cyclobutane-1,2,3,4-tetrayl group, a cyclopentane-1,1,2,2-tetrayl group, a cyclopentane-1,1,3,3-tetrayl group, a cyclopentane-1,1,2,3-tetrayl group, a cyclopentane-1,1,2,4-tetrayl group, a cyclopentane-1,1,2,5-tetrayl group, a cyclopentane-1,1,3,4-tetrayl group, a cyclopentane-1,2,3,4-tetrayl group, a cyclohexane-1,2,3,4-tetrayl group, a cyclohexane-1,2,4,5-tetrayl group, a cyclohexane-1,2,3,5-tetrayl group, a cycloheptane-1,2,3,4-tetrayl group, a cycloheptane-1,2,4,5-tetrayl group, a cyclooctane-1,2,3,4-tetrayl group, a cyclooctane-1,2,4,5-tetrayl group and a cyclooctane-1,2,5,6-tetrayl group; tetravalent chain unsaturated hydrocarbon groups such as an ethene-1,1,2,2-tetrayl group, a propylene-1,1,2,3-tetrayl group, a propylene-1,1,3,3-tetrayl group, a propylene-1,3,3,3-tetrayl group, a propylene-1,2,3,3-tetrayl group and a propylene-2,3,3,3-tetrayl group; and tetravalent unsaturated cyclic hydrocarbon groups such as a cyclopentene-1,2,3,4-tetrayl group, a cyclopentene-1,3,4,5-tetrayl group, a benzene-1,2,3,4-tetrayl group, a benzene-1,2,4,5-tetrayl group, a naphthalene-1,2,3,4-tetrayl group, a naphthalene-1,2,5,6-tetrayl group, a naphthalene-1,2,6,7-tetrayl group, a naphthalene-1,2,7,8-tetrayl group, a naphthalene-2,3,5,6-tetrayl group and a naphthalene-2,3,6,7-tetrayl group.

Further, in the tetravalent hydrocarbon group, part or all of hydrogen atoms therein may be replaced with a monovalent hydrocarbon group having 1 to 30 carbon atoms that is defined as above, optionally substituted with a heteroatom and optionally having an intervening heteroatom.

And further, in the tetravalent hydrocarbon group, part or all of hydrogen atoms therein may be replaced with a substituent comprising a heteroatom such as an oxygen atom, a sulfur atom, a nitrogen atom and a halogen atom, and as a result, the tetravalent hydrocarbon group may comprise a hydroxy group, an amino group, a cyano group, a nitro group, a haloalkyl group or the like.

Furthermore, in the tetravalent hydrocarbon group, one or more of the carbon atoms therein may be replaced with a substituent comprising a heteroatom such as an oxygen atom, a sulfur atom and a nitrogen atom, and as a result, the tetravalent hydrocarbon group may comprise an ether bond, a sulfide bond, a carbonyl group, an ester bond, —N(R)— (wherein R is a hydrogen atom or a monovalent hydrocarbon group having 1 to 30 carbon atoms that is optionally substituted with a heteroatom and optionally has an intervening heteroatom), an amide bond, an imino bond, a sulfonyl group, a sulfinyl group, a sulfonate ester group, a sulfonamide bond, a carbonate bond, a carbamate bond, a carboxylic anhydride (—C(=O)—O—C(=O)—) or the like.

In formula (3), as the substituent represented by $Y^1$, particularly suitable are those shown below, provided that -* represents an attachment point. Note that the present invention is not limited to them.

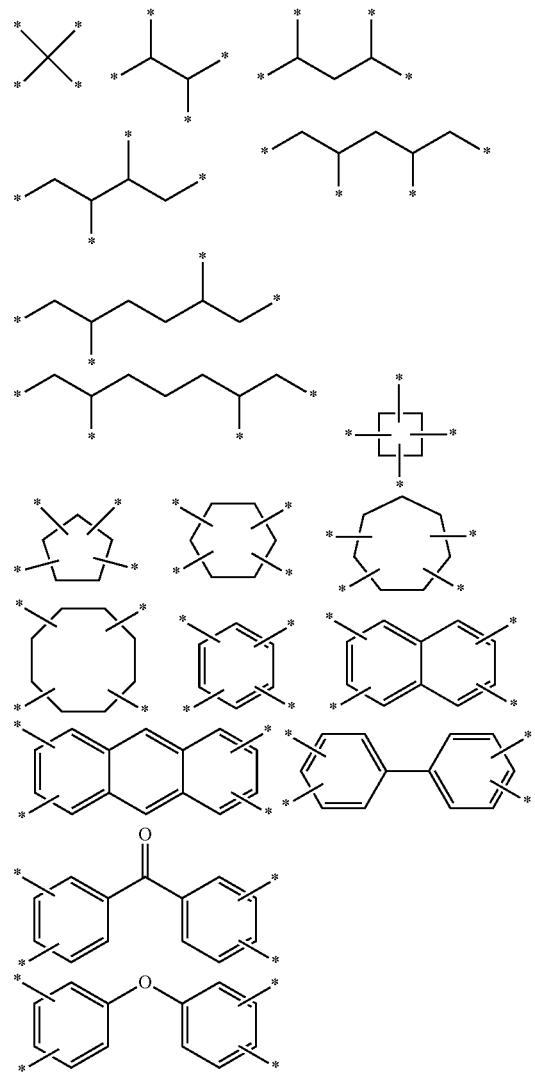

-continued
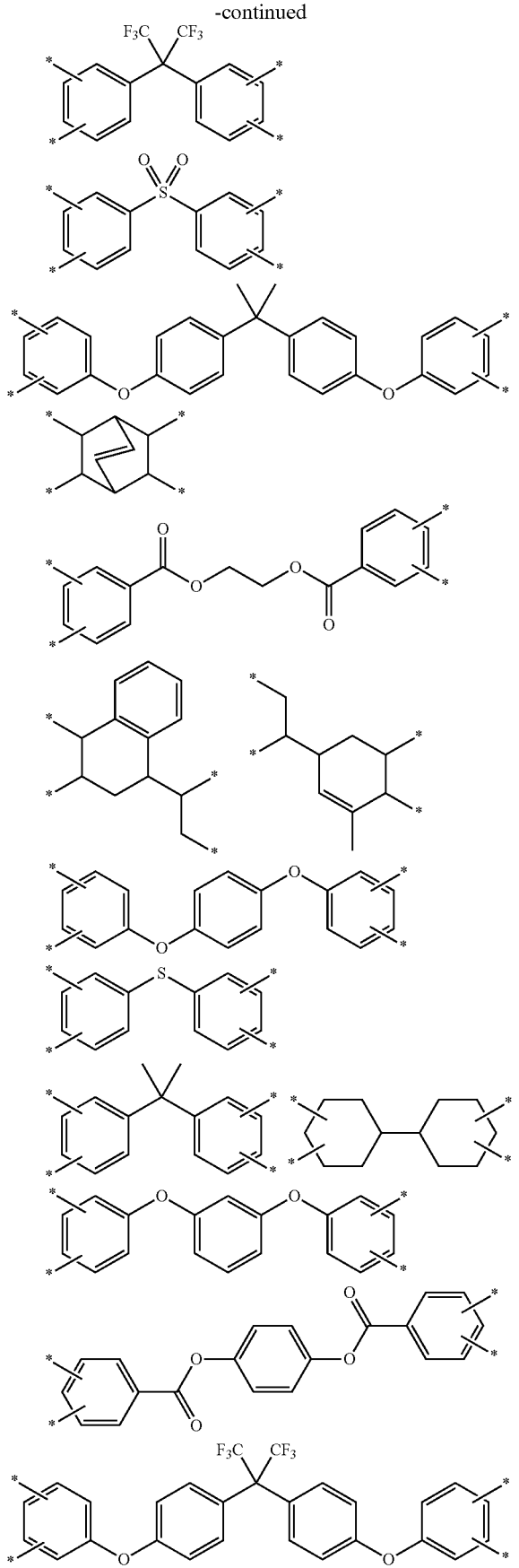
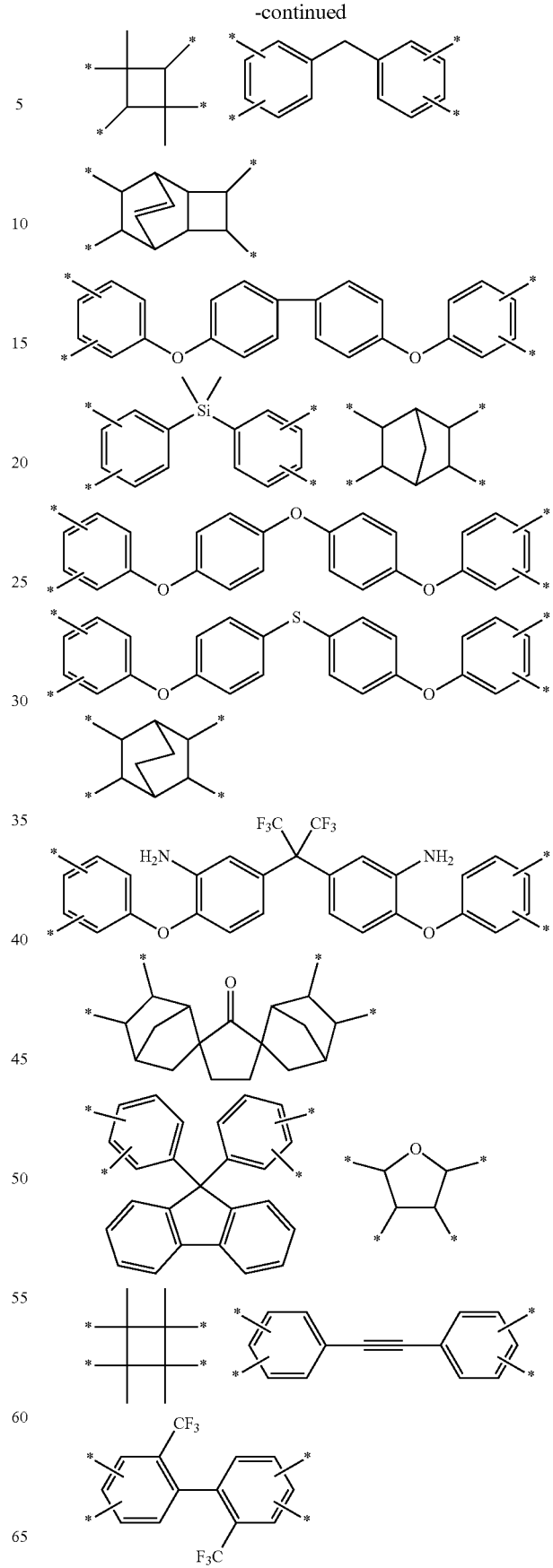

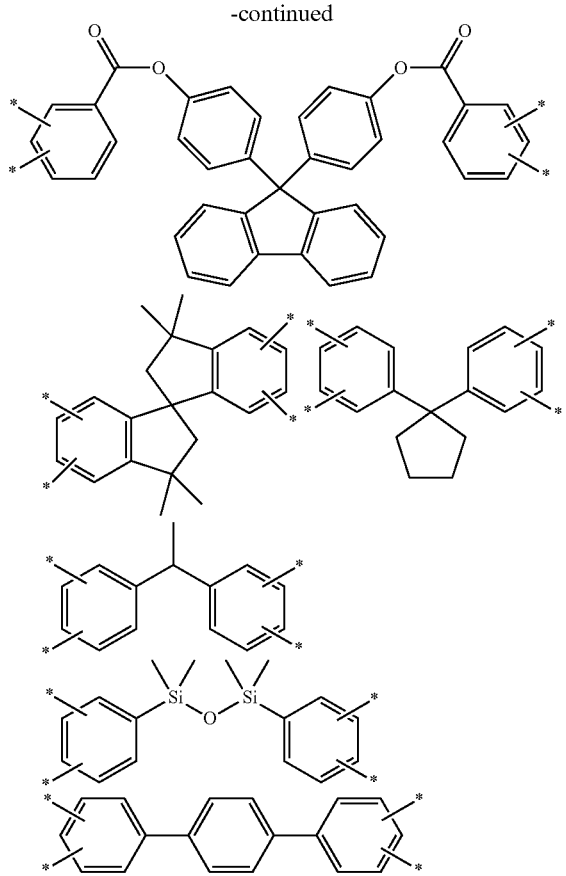

Such a resin comprises the compound that the present invention provides as a resin structural unit and also contains a polyimide unit excellent in strength and durability, and therefore, can accomplish high tensile strength, high extensibility and high durability while having excellent organic solvent solubility.

Moreover, the present invention provides a resin further comprising, in addition to the structural units (2) and (3), a structural unit represented by the following general formula (4):

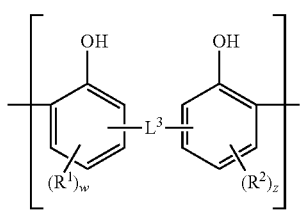

(4)

wherein $L^3$ is a single bond or a divalent linking group; $R^1$ to $R^2$ each independently represent any monovalent substituent; and w and z are 0 to 3, and when they are 2 or more, substituents represented by a plurality of $R^1$ and $R^2$ may be the same as or different from each other.

In formula (4), $L^3$ represents a single bond or a divalent linking group.

Examples of the divalent linking group that can be used as $L^3$ include a divalent hydrocarbon group having 1 to 30 carbon atoms that is defined as above, optionally substituted with a heteroatom and optionally having an intervening heteroatom; and divalent heteroatom-containing groups such as an ether bond, a sulfide bond, a carbonyl group, an ester bond, —N(R)— (wherein R is a hydrogen atom or a monovalent hydrocarbon group having 1 to 29 carbon atoms that is optionally substituted with a heteroatom and optionally has an intervening heteroatom), an amide bond, an imino bond, a sulfonyl group, a sulfinyl group, a sulfonate ester group, a sulfonamide bond, a carbonate bond, a carbamate bond and a carboxylic anhydride (—C(=O)—O—C(=O)—).

In formula (4), as the divalent hydrocarbon group that can be used as $L^3$, particularly suitable are those shown below, provided that -* represents an attachment point. Note that the present invention is not limited to them.

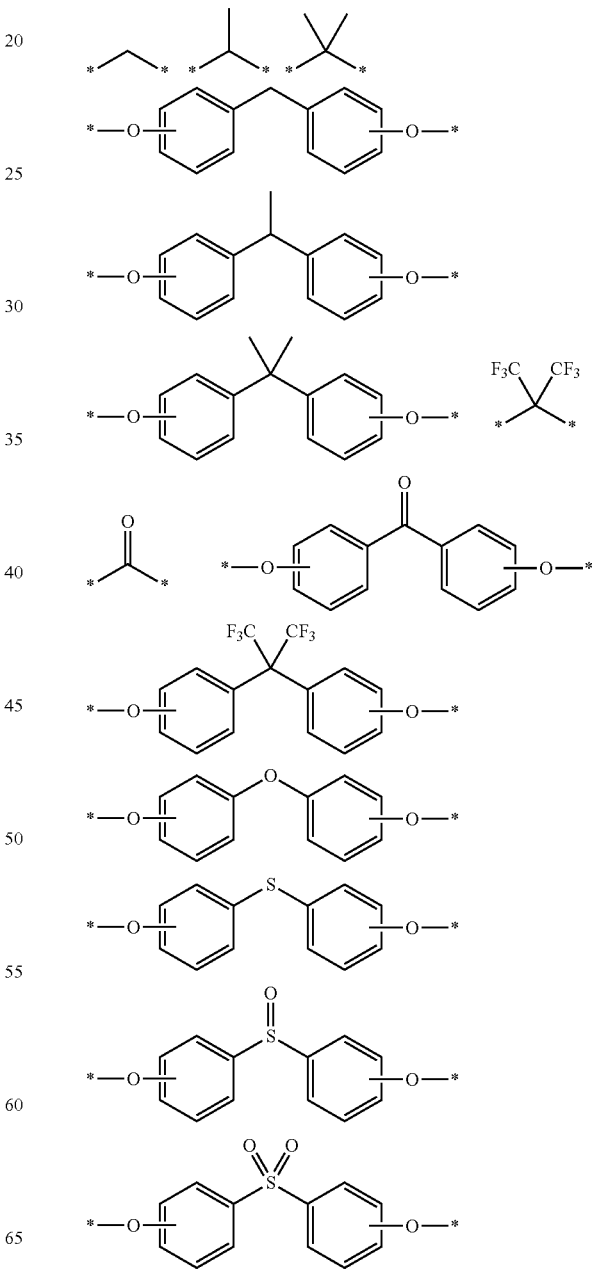

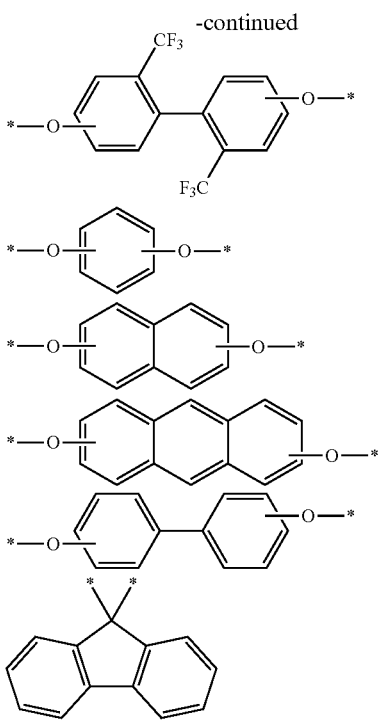

$R^1$ to $R^2$ each independently represent any monovalent substituent.

Examples of the monovalent substituent that can be used as $R^1$ to $R^2$ include a monovalent hydrocarbon group having 1 to 30 carbon atoms that is defined as above, optionally substituted with a heteroatom and optionally having an intervening heteroatom; and monovalent heteroatom-containing groups such as a halogen atom, a hydroxy group, an amino group, a cyano group, a nitro group, a nitroso group and a mercapto group.

A resin comprising such a unit is soluble in a basic aqueous solution and a basic organic solvent due to the effect of acidic hydroxy groups of the phenol units. In a resin having such properties, by adding a photosensitive or radiation sensitive additive and a dissolution controlling agent, the water solubility and the organic solvent solubility can be controlled, and as a result, patterning by lithography can be performed.

As $L^3$ in general formula (4), $-CR^{f1}R^{f2}-$ or $-SO_2-$ is particularly desirable, provided that $R^{f1}$ to $R^{f2}$ are each independently a fluorine atom or a fluoroalkyl group having 1 to 10 carbon atoms.

Examples of the fluoroalkyl group that can be used as $R^{f1}$ to $R^{f2}$ include partially fluorinated hydrocarbon groups such as a monofluoromethyl group, a difluoromethyl group, a 2-monofluoroethyl group, a 2,2-difluoroethyl group, a 2,2,2-trifluoroethyl group and a 1,1,1,3,3,3-hexafluoroisopropyl group; and perfluoroalkyl groups such as a trifluoromethyl group, a pentafluoroethyl group, a heptafluoropropyl group and a nonafluorobutyl group.

Such a resin comprising structural unit (4) having such a substituent is suitable for application to lithography, due to the higher acidity of the phenolic hydroxy groups and further improved solubility in a basic aqueous solution and a basic organic solvent.

The polyimide resin according to the present invention can be utilized for either a positive photosensitive resin composition that allows development with an aqueous alkaline solution or a negative photosensitive resin composition that allows development with an aqueous alkaline solution because the polyimide resin is soluble in a developing solution of an aqueous alkaline solution, and a pattern obtained by using these photosensitive resin compositions is fine and the pattern shape is good.

Method of Producing Resin

The present invention further provides a method of producing the above-described resin, wherein the above-described compound, or an acid halide or acid anhydride derived therefrom is reacted with the following formula (5) and at least one of compounds represented by the following general formulas (6) to (7):

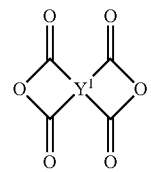 (5)

 (6)

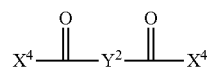 (7)

wherein $Y^1$ is defined as above; $Y^2$ represents a divalent hydrocarbon group having 1 to 100 carbon atoms that is optionally substituted with a heteroatom and optionally has an intervening heteroatom; and $X^4$ represents any of a hydroxy group, a fluorine atom, a chlorine atom, a bromine atom, an iodine atom, $-OCO_2R^{X4}$, $-OSO_2R^{X4}$ and $-OSO_3R^{X4}$, provided that $R^{X4}$ is a monovalent hydrocarbon group having 1 to 10 carbon atoms that is optionally substituted with a heteroatom and optionally has an intervening heteroatom.

In formula (7), $Y^2$ represents a divalent hydrocarbon group having 1 to 100 carbon atoms that is defined as above, optionally substituted with a heteroatom and optionally having an intervening heteroatom. In addition, in that formula, $R^{X4}$ represents a monovalent hydrocarbon group having 1 to 10 carbon atoms that is defined as above, optionally substituted with a heteroatom and optionally having an intervening heteroatom.

In formula (7), as the substituent represented by $Y^2$, particularly suitable are those shown below, provided that -* represents an attachment point. Note that the present invention is not limited to them.

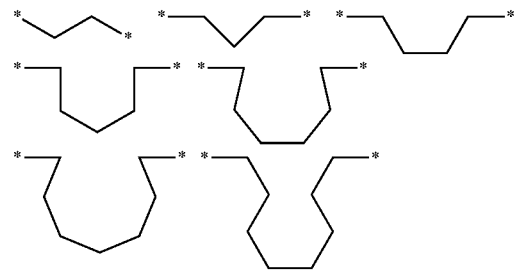

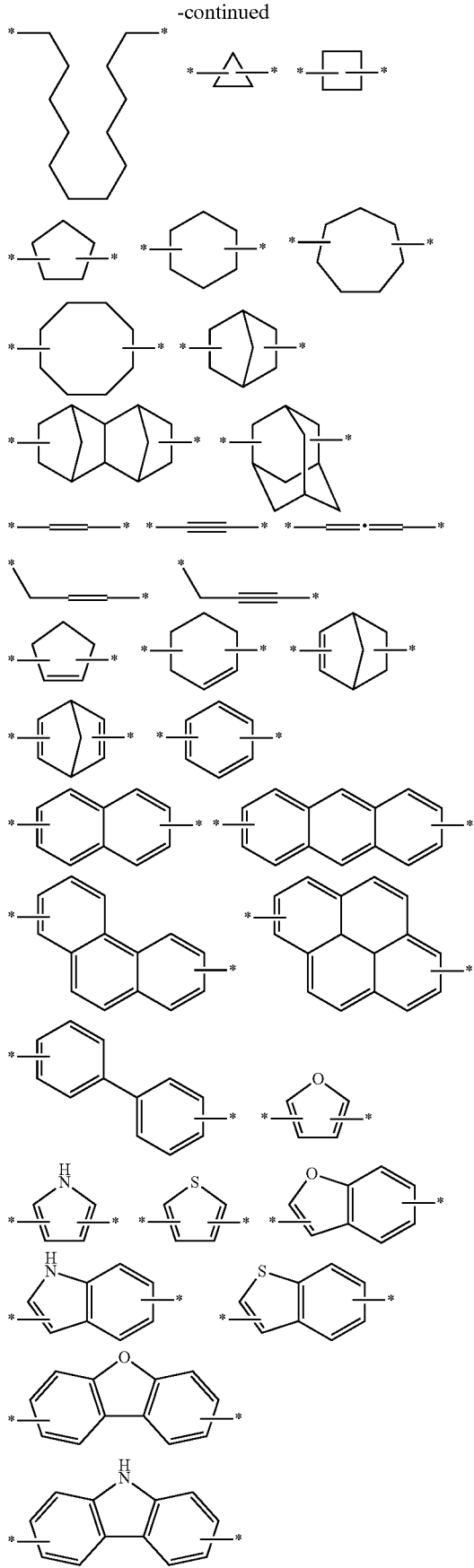
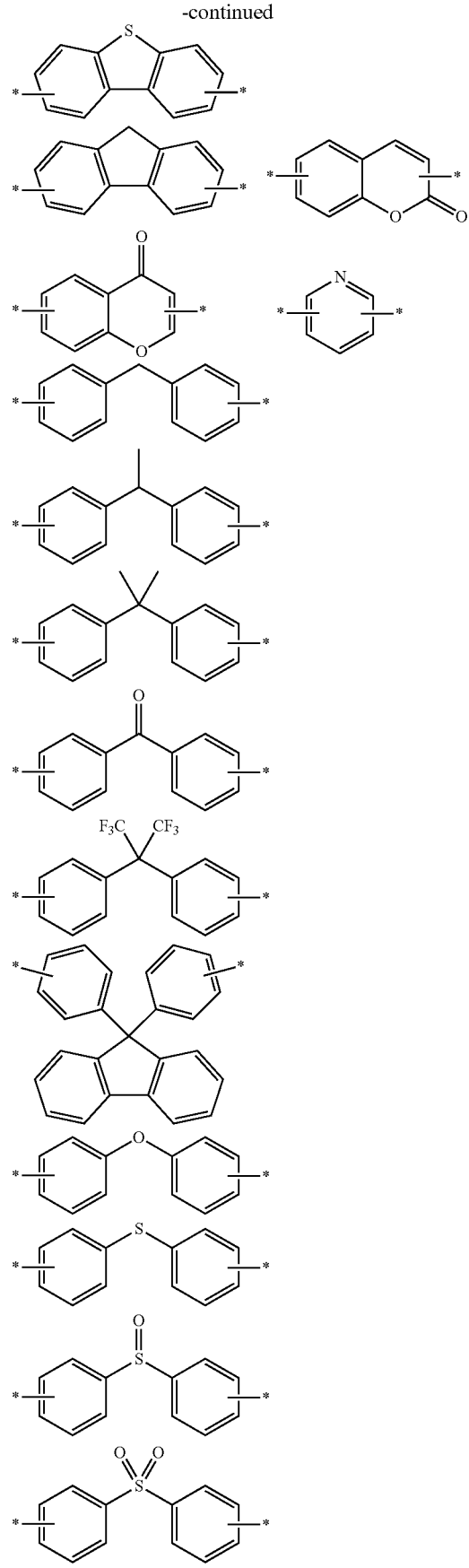

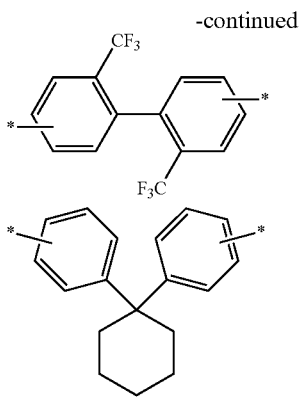

A method of producing a polyimide resin comprising structural units represented by the above-described general formula (2) and (3) varies depending on the type of $X^3$ in the compound represented by general formula (1).

Production Method 1

When $X^3$ in general formula (1) is $-CO_2-$, $-SO_2-$ or $-SO_3-$, such a compound works as an electrophilic monomer unit in the polycondensation reaction. In order to express its polymerization activity, it is required to convert $-CO_2H$, $-SO_2H$ or $-SO_3H$ group present at the end of the compound into an acid halide or acid anhydride. Examples of the approach of converting such compound groups into an acid halide include reaction with a simple substance of halogen and reaction with an equivalent of halogen such as thionyl chloride, oxalyl chloride, sulfuryl chloride, thionyl bromide, oxalyl bromide, sulfuryl bromide, bromine monochloride and iodine monochloride. In addition, examples of the approach of converting such compounds into an acid anhydride include reaction with a halogenated carbonate ester, a carbonate ester anhydride, an acid halide, a carbodiimide and the like.

By reacting a compound represented by general formula (1) that has been activated by the above-described approaches with any tetracarboxylic dianhydride and any diamine, a polyamic acid having structural units represented by the above-described general formula (2) and (3) in a backbone thereof is obtained.

Suitable examples of the above-described tetracarboxylic dianhydride include aromatic acid dianhydrides, alicyclic acid dianhydrides, aliphatic acid dianhydrides and the like. Examples of the aromatic acid dianhydride include, but are not limited to, pyromellitic dianhydride, 3,3',4,4'-biphenyltetracarboxylic dianhydride, 2,3,3',4'-biphenyltetracarboxylic dianhydride, 2,3,2',3'-biphenyltetracarboxylic dianhydride, 3,3',4,4'-terphenyltetracarboxylic dianhydride, 3,3',4,4'-oxyphthalic dianhydride, 2,3,3',4'-oxyphthalic dianhydride, 2,3,2',3'-oxyphthalic dianhydride, diphenylsulfone-3,3',4,4'-tetracarboxylic dianhydride, benzophenone-3,3',4,4'-tetracarboxylic dianhydride, 2,2-bis(3,4-dicarboxyphenyl)propane dianhydride, 2,2-bis(2,3-dicarboxyphenyl)propane dianhydride, 1,1-bis(3,4-dicarboxyphenyl)ethane dianhydride, 1,1-bis(2,3-dicarboxyphenyl)ethane dianhydride, bis(3,4-dicarboxyphenyl)methane dianhydride, bis(2,3-dicarboxyphenyl)methane dianhydride, 1,4-(3,4-dicarboxyphenoxy)benzene dianhydride, p-phenylenebis(trimellitic acid monoester acid anhydride), bis(1,3-dioxo-1,3-dihydroisobenzfuran-5-carboxylic acid)1,4-phenylene, 1,2,5,6-naphthalenetetracarboxylic dianhydride, 2,3,6,7-naphthalenetetracarboxylic dianhydride, 9,9-bis(3,4-dicarboxyphenyl)fluorene dianhydride, 2,3,5,6-pyridinetetracarboxylic dianhydride, 3,4,9,10-perylenetetracarboxylic dianhydride, 2,2-bis(3,4-dicarboxyphenyl)hexafluoropropane dianhydride, 2,2-bis(4-(3,4-dicarboxybenzoyloxy)phenyl)hexafluoropropane dianhydride, 1,6-difluoropyromellitic dianhydride, 1-trifluoromethylpyromellitic dianhydride, 1,6-ditrifluoromethylpyromellitic dianhydride, 2,2'-bis(trifluoromethyl)-4,4'-bis(3,4-dicarboxyphenoxy)biphenyl dianhydride, 2,2'-bis[(dicarboxyphenoxy)phenyl]propane dianhydride, 2,2'-bis[(dicarboxyphenoxy)phenyl]hexafluoropropane dianhydride, and acid dianhydride compounds formed by substituting aromatic rings of the above compounds with an alkyl group, an alkoxy group, a halogen atom or the like.

Examples of the alicyclic acid dianhydride include, but are not limited to, 1,2,3,4-cyclobutanetetracarboxylic dianhydride, 1,2,3,4-cyclopentanetetracarboxylic dianhydride, 1,2,4,5-cyclohexanetetracarboxylic dianhydride, 1,2,4,5-cyclopentanetetracarboxylic dianhydride, 1,2,3,4-tetramethyl-1,2,3,4-cyclobutanetetracarboxylic dianhydride, 1,2-dimethyl-1,2,3,4-cyclobutanetetracarboxylic dianhydride, 1,3-dimethyl-1,2,3,4-cyclobutanetetracarboxylic dianhydride, 1,2,3,4-cycloheptanetetracarboxylic dianhydride, 2,3,4,5-tetrahydrofurantetracarboxylic dianhydride, 3,4-dicarboxy-1-cyclohexylsuccinic dianhydride, 2,3,5-tricarboxycyclopentylacetic dianhydride, 3,4-dicarboxy-1,2,3,4-tetrahydro-1-naphthalenesuccinic dianhydride, bicyclo[3.3.0]octane-2,4,6,8-tetracarboxylic dianhydride, bicyclo[4.3.0]nonane-2,4,7,9-tetracarboxylic dianhydride, bicyclo[4.4.0]decane-2,4,7,9-tetracarboxylic dianhydride, bicyclo[4.4.0]decane-2,4,8,10-tetracarboxylic dianhydride, tricycle[6.3.0.0$^{2,6}$]undecane-3,5,9,11-tetracarboxylic dianhydride, bicyclo[2.2.2]octane-2,3,5,6-tetracarboxylic dianhydride, bicyclo[2.2.2]oct-7-ene-2,3,5,6-tetracarboxylic dianhydride, bicyclo[2.2.1]heptanetetracarboxylic dianhydride, bicyclo[2.2.1]heptane-5-carboxymethyl-2,3,6-tricarboxylic dianhydride, 7-oxabicyclo[2.2.1]heptane-2,4,6,8-tetracarboxylic dianhydride, octahydronaphthalene-1,2,6,7-tetracarboxylic dianhydride, tetradecahydroanthracene-1,2,8,9-tetracarboxylic dianhydride, 3,3',4,4'-dicyclohexanetetracarboxylic dianhydride, 3,3',4,4'-oxydicyclohexanetetracarboxylic dianhydride, 5-(2,5-dioxotetrahydro-3-furanyl)-3-methyl-3-cyclohexene-1,2-dicarboxylic anhydride, and "RIKACID" (Registered Trademark) BT-100 (trade name, manufactured by New Japan Chemical Co., Ltd.) and their derivatives, or acid dianhydride compounds formed by substituting aliphatic rings of the above compounds with an alkyl group, an alkoxy group, a halogen atom or the like.

Examples of the aliphatic acid dianhydride include, but are not limited to, 1,2,3,4-butanetetracarboxylic dianhydride, 1,2,3,4-pentanetetracarboxylic dianhydride and their derivatives.

One of these aromatic acid dianhydrides, alicyclic acid dianhydrides or aliphatic acid dianhydrides may be used singly, or two or more of them may be used in combination.

Examples of the above-described diamine include hydroxy-group containing diamines, aromatic diamines, alicyclic diamines and aliphatic diamines. Preferable examples of the hydroxy group-containing diamine include, but are not limited to, 3,3'-diamino-4,4'-dihydroxybiphenyl, 4,4'-diamino-3,3'-dihydroxybiphenyl, bis(3-amino-4-hydroxyphenyl)sulfone, bis(4-amino-3-hydroxyphenyl)sulfone, 2,2-bis(3-amino-4-hydroxyphenyl)hexafluoropropane, 2,2-bis(4-amino-3-hydroxyphenyl)hexafluoropropane, 2,2-bis(3-amino-4-hydroxyphenyl)propane and 2,2-bis(4-amino-3-hydroxyphenyl)propane.

Examples of the aromatic diamine include, but are not limited to, 3,4'-diaminodiphenyl ether, 4,4'-diaminodiphenyl ether, 3,4'-diaminodiphenylmethane, 4,4'-diaminodiphenylmethane, 3,3'-diaminodiphenylsulfone, 3,4'-diaminodiphenylsulfone, 4,4'-diaminodiphenylsulfone, 3,4'-diaminodiphenylsulfide, 4,4'-diaminodiphenylsulfide, 1,4-bis(4-aminophenoxy)benzene, benzidine, 2,2'-bis(trifluoromethyl)benzidine, 3,3'-bis(trifluoromethyl)benzidine, 2,2'-dimethylbenzidine, 3,3'-dimethylbenzidine, 2,2'3,3'-tetramethylbenzidine, 2,2'-dichlorobenzidine, 3,3'-dichlorobenzidine, 2,2'3,3'-tetrachlorobenzidine, m-phenylene diamine, p-phenylene diamine, 1,5-naphthalenediamine, 2,6-naphthalenediamine, bis(4-aminophenoxyphenyl)sulfone, bis(3-aminophenoxyphenyl)sulfone, bis[4-(3-aminophenoxy)phenyl]sulfone, bis(4-aminophenoxy)biphenyl, bis{4-(4-aminophenoxy)phenyl} ether, 1,4-bis(4-aminophenoxy)benzene, 9,9-bis(4-aminophenyl)fluorene, 2,2'-bis[3-(3-aminobenzamide)-4-hydroxyphenyl]hexafluoropropane, 4-aminophenyl-4'-aminobenzoate, 4,4'-diaminobenzanilide, or diamine compounds formed by substituting aromatic rings of the above compounds with an alkyl group, an alkoxy group, a halogen atom or the like.

Examples of the alicyclic diamine include, but are not limited to, cyclobutanediamine, isophoronediamine, bicyclo[2.2.1]heptanebismethylamine, tricyclo[3.3.1.13.7]decane-1,3-diamine, 1,2-cyclohexyldiamine, 1,3-cyclohexyldiamine, 1,4-diaminocyclohexane, trans-1,4-diaminocyclohexane, cis-1,4-diaminocyclohexane, 4,4'-diaminodicyclohexylmethane, 3,3'-dimethyl-4,4'-diaminodicyclohexylmethane, 3,3'-diethyl-4,4'-diaminodicyclohexylmethane, 3,3',5,5'-tetramethyl-4,4'-diaminodicyclohexylmethane, 3,3',5,5'-tetraethyl-4,4'-diaminodicyclohexylmethane, 3,5-diethyl-3',5'-dimethyl-4,4'-diaminodicyclohexylmethane, 4,4'-diaminodicyclohexyl ether, 3,3'-dimethyl-4,4'-diaminodicyclohexyl ether, 3,3'-diethyl-4,4'-diaminodicyclohexyl ether, 3,3',5,5'-tetramethyl-4,4'-diaminodicyclohexyl ether, 3,3',5,5'-tetraethyl-4,4'-diaminodicyclohexyl ether, 3,5-diethyl-3',5'-dimethyl-4,4'-diaminodicyclohexyl ether, 2,2-bis(4-aminocyclohexyl)propane, 2,2-bis(3-methyl-4-aminocyclohexyl)propane, 2,2-bis(3-ethyl-4-aminocyclohexyl)propane, 2,2-bis(3,5-dimethyl-4-aminocyclohexyl)propane, 2,2-bis(3,5-diethyl-4-aminocyclohexyl)propane, 2,2-(3,5-diethyl-3',5'-dimethyl-4,4'-diaminodicyclohexyl)propane, or diamine compounds formed by substituting aliphatic rings of the above compounds with an alkyl group, an alkoxy group, a halogen atom or the like.

Examples of the aliphatic diamine include, but are not limited to, alkylene diamines such as ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane and 1,10-diaminodecane; ethylene glycol diamines such as bis(aminomethyl) ether, bis(2-aminoethyl) ether and bis(3-aminopropyl) ether; and siloxane diamines such as 1,3-bis(3-aminopropyl)tetramethyldisiloxane, 1,3-bis(4-aminobutyl)tetramethyldisiloxane and α,ω-bis(3-aminopropyl)polydimethylsiloxane.

One of these diamines having hydroxy-group, aromatic diamines, alicyclic diamines or aliphatic diamines may be used singly, or two or more of them may be used in combination.

And, siloxane diamines can also be suitably used.

And, in addition to the above-described monomer units, a diamine compound that can configure the unit represented by general formula (4) in the polymer can be used.

Production Method 2

When $X^3$ in general formula (1) is —CONR$^{X1}$—, —O—, —NR$^{X1}$—, —S— or —SO$_2$NR$^{X1}$—, such a compound functions as a nucleophilic monomer unit in the polycondensation reaction. Upon this, by reacting such a compound with any tetracarboxylic dianhydride and any diamine, a polyamic acid having structural units represented by the above-described general formulas (2) and (3) in a backbone thereof is obtained.

In the above-described approach, a tetracarboxylic dianhydride and diamine that are the same as mentioned above can be used.

And, in addition to the above-described monomer units, any carboxylic acid represented by general formula (7), or an acid halide or acid anhydride derived therefrom can be used.

Examples of the carboxylic acid represented by general formula (7), or an acid halide or acid anhydride derived therefrom include, but are not limited to, dicarboxylic acids such as 3,4'-diphenyl ether-3,4'-dicarboxylic acid, diphenyl ether-4,4'-dicarboxylic acid, diphenylmethane-3,4'-dicarboxylic acid, diphenylmethane-4,4'-dicarboxylic acid, diphenylsulfone-3,3'-dicarboxylic acid, diphenylsulfone-3,4'-dicarboxylic acid, diphenylsulfone-4,4'-dicarboxylic acid, diphenylsulfide-3,4'-dicarboxylic acid, diphenylsulfide-4,4'-dicarboxylic acid, 1,4-bis(4-carboxyphenoxy)benzene, phthalic acid, terephthalic acid, isophthalic acid, biphenyldicarboxylic acid, 2,2'-bis(trifluoromethyl)biphenyldicarboxylic acid, 3,3'-bis(trifluoromethyl)biphenyldicarboxylic acid, 2,2'-dimethylbiphenyldicarboxylic acid, 3,3'-dimethylbiphenyldicarboxylic acid, 2,2'3,3'-tetramethylbiphenyldicarboxylic acid, 2,2'-dichlorobiphenyldicarboxylic acid, 3,3'-dichlorobiphenyldicarboxylic acid, 2,2'3,3'-tetrachlorobiphenyldicarboxylic acid, 1,5-naphthalenedicarboxylic acid, 2,6-naphthalenedicarboxylic acid, bis(4-carboxyphenoxyphenyl)sulfone, bis(3-carboxyphenoxyphenyl)sulfone, bis[4-(3-carboxyphenoxy)phenyl]sulfone, bis(4-carboxyphenoxy)biphenyl, bis{4-(4-carboxyphenoxy)phenyl} ether, 1,4-bis(4-carboxyphenoxy)benzene, 9,9-bis(4-carboxyphenyl)fluorene, 2,2'-bis[3-(3-carboxybenzamide)-4-carboxyphenyl]hexafluoropropane, 4-carboxyphenyl-4'-carboxybenzoate, 4,4'-dicarboxybenzanilide, and those obtained by substituting aromatic rings of the above compounds with an alkyl group, alkoxy group, halogen atom or the like; diol compounds such as cyclobutanedicarboxylic acid, isophoronedicarboxylic acid, bicyclo[2,2,1]heptanediacetic acid, tricyclo[3,3,1,13,7]decane-1,3-dicarboxylic acid, 1,2-cyclohexyldicarboxylic acid, 1,3-cyclohexyldicarboxylic acid, 1,4-cyclohexanedicarboxylic acid, trans-1,4-cyclohexanedicarboxylic acid, cis-1,4-cyclohexanedicarboxylic acid, 4,4-cyclohexylmethanedicarboxylic acid, 3,3'-dimethyl-4,4'-cyclohexylmethanedicarboxylic acid, 3,3'-diethyl-4,4'-cyclohexylmethanedicarboxylic acid, 3,3',5,5'-tetramethyl-4,4'-dicyclohexylmethanedicarboxylic acid, 3,3',5,5'-tetraethyl-4,4'-dicyclohexylmethanedicarboxylic acid, 3,5-diethyl-3',5'-dimethyl-4,4'-dicyclohexylmethanedicarboxylic acid, 4,4'-dicyclohexyl ether dicarboxylic acid, 3,3'-dimethyl-4,4'-dicyclohexyl ether dicarboxylic acid, 3,3'-diethyl-4,4'-dicyclohexyl ether dicarboxylic acid, 3,3',5,5'-tetramethyl-4,4'-dicyclohexyl ether dicarboxylic acid, 3,3',5,5'-tetraethyl-4,4'-dicyclohexyl ether dicarboxylic acid, 3,5-diethyl-3',5'-dimethyl-4,4'-dicyclohexyl ether dicarboxylic acid, 2,2-bis(4-carboxycyclohexyl)propane, 2,2-bis(3-methyl-4-carboxycyclohexyl)propane, 2,2-bis(3-ethyl-4-carboxycyclohexyl)propane, 2,2-bis(3,5-dimethyl-4-carboxycyclohexyl)propane, 2,2-bis(3,5-diethyl-4-carboxycyclohexyl)propane, 2,2-(3,5-diethyl-3',5'-dimethyl-4,4'-dicarboxydicyclohexyl)propane, or those obtained by substituting aliphatic rings of the above compounds with an alkyl group, alkoxy group, halogen atom or the like; alkylenedicarboxylic acids such as ethanedicarboxylic acid, 1,3-propanedicarboxylic acid, 1,4-butanedicarboxylic acid, 1,5-pentanedicarboxylic acid, 1,6-hexanedicarboxylic acid, 1,7-heptanedicarboxylic acid, 1,8-octanedicarboxylic acid, 1,9-nonanedicarboxylic acid and 1,10-decanedicarboxylic acid; polyether dicarboxylic acids such as bis(carboxymethyl) ether, bis(2-carboxyethyl) ether and bis(3-carboxypropyl) ether; and siloxane dicarboxylic acids such as 1,3-bis(3-carboxypropyl)tetramethyldisiloxane, 1,3-bis(4-carboxybutyl)tetramethyldisiloxane and α,ω-bis(3-carboxypropyl)polydimethylsiloxane, or acid halides and acid anhydrides derived therefrom. One of these dicarboxylic acids and acid halides or acid anhydrides derived therefrom may be used singly, or two or more of them may be used in combination.

In the synthesis of polyamic acid, the proportion among a compound represented by the above-described general formula (1), a diamine, a tetracarboxylic dianhydride and other dicarboxylic acid derivative is appropriately determined depending on adjustment of the molecular weight of the polyimide and the like, and when $X^3$ in general formula (1) is —$CO_2$—, —$SO_2$— or —$SO_3$—, the ratio of the compound represented by the above-described general formula (1), the tetracarboxylic dianhydride and the dicarboxylic acid derivative to the diamine is normally in the range of, in the molar ratio, 0.90 to 1.10, preferably 0.95 to 1.05, and more preferably 0.98 to 1.02. And, when $X^3$ in general formula (1) is —$CONR^{X1}$—, —O—, —$NR^{X1}$—, —S— or —$SO_2NR^{X1}$—, the ratio of the compound represented by the above-described general formula (1) and the diamine to the tetracarboxylic dianhydride and the dicarboxylic acid derivative is normally in the range of, in the molar ratio, 0.90 to 1.10, preferably 0.95 to 1.05, and more preferably 0.98 to 1.02.

The reaction among the compound represented by the above-described general formula (1), diamine, tetracarboxylic dianhydride and other dicarboxylic acid derivative is normally performed by mixing monomer components in a solvent at 0 to 80° C., preferably at 10 to 50° C.

Specific examples of the solvent include ethers such as tetrahydrofuran and anisole; ketones such as cyclohexanone, 2-butanone, methyl isobutyl ketone, 2-heptanone, 2-octanone and acetophenone; esters such as butyl acetate, methyl benzoate and γ-butyrolactone; cellosolves such as butyl cellosolve acetate and propylene glycol monomethyl ether acetate; amides such as N,N-dimethylformamide, N,N-dimethylacetamide and N-methyl-2-pyrrolidone; and aromatic hydrocarbons such as toluene and xylene, and the solvent is preferably a ketone, an ester or an amide, and particularly preferably γ-butyrolactone, N,N-dimethylacetamide or N-methyl-2-pyrrolidone. One of these solvents may be used singly, or two or more of them may be used in combination. Normally, considering the solution viscosity, the concentration of the polyimide is within the range of 10 to 40% by mass.

Next, by adding a non-polar solvent that may cause azeotropic with water, such as xylene, to the reaction solution of polyamic acid obtained as described above, heating the resultant mixture to 100 to 200° C., preferably 130 to 180° C., and conducting dehydration ring closure reaction with removing generated water from the reaction system, a polyimide resin comprising structural units represented by the above-described general formulas (2) and (3) can be obtained.

Molecular Weight of Polymer and Introduction of End-Capping Agent

A suitable weight average molecular weight of a polyimide resin comprising structural unit (2) and structural unit (3) or a polyimide resin comprising structural unit (2), structural unit (3) and structural unit (4) is preferably 5,000 to 100,000, and more preferably 7,000 to 50,000. When the molecular weight is 5,000 or more, it becomes easy to make a film of a photosensitive resin composition using the above-described polyimide resin as a base resin with a desired film thickness on a substrate, and when the molecular weight is 100,000 or less, the viscosity of the photosensitive resin composition is not remarkably high, and thus, there is no fear of not being able to form a film. Note that the weight average molecular weight herein is a value measured by gel permeation chromatography (GPC) in terms of polystyrene.

Polyimide resin comprising structural unit (2) and structural unit (3), or polyimide resin comprising structural unit (2), structural unit (3) and structural unit (4) may be capped at both ends with an end-capping agent for the purposes of controlling the molecular weight in the polycondensation reaction and preventing time-dependent change in the molecular weight of the obtained polymer, that is, gelation. Examples of an end-capping agent that reacts with an acid dianhydride include monoamines and monohydric alcohols. And, examples of an end-capping agent that reacts with a diamine compound include acid anhydrides, monocarboxylic acids, monoacid chloride compounds, monoactive ester compounds, dicarbonate esters and vinyl ethers. In addition, by reacting with an end-capping agent, a variety of organic groups can be introduced as an end group.

Examples of the monoamine to be used as the capping agent for the acid anhydride group terminal include, but are not limited to, aniline, 5-amino-8-hydroxyquinoline, 4-amino-8-hydroxyquinoline, 1-hydroxy-8-aminonaphthalene, 1-hydroxy-7-aminonaphthalene, 1-hydroxy-6-aminonaphthalene, 1-hydroxy-5-aminonaphthalene, 1-hydroxy-4-aminonaphthalene, 1-hydroxy-3-aminonaphthalene, 1-hydroxy-2-aminonaphthalene, 1-amino-7-hydroxynaphthalene, 2-hydroxy-7-aminonaphthalene, 2-hydroxy-6-aminonaphthalene, 2-hydroxy-5-aminonaphthalene, 2-hydroxy-4-aminonaphthalene, 2-hydroxy-3-aminonaphthalene, 1-amino-2-hydroxynaphthalene, 1-carboxy-8-aminonaphthalene, 1-carboxy-7-aminonaphthalene, 1-carboxy-6-aminonaphthalene, 1-carboxy-5-aminonaphthalene, 1-carboxy-4-aminonaphthalene, 1-carboxy-3-aminonaphthalene, 1-carboxy-2-aminonaphthalene, 1-amino-7-carboxynaphthalene, 2-carboxy-7-aminonaphthalene, 2-carboxy-6-aminonaphthalene, 2-carboxy-5-aminonaphthalene, 2-carboxy-4-aminonaphthalene, 2-carboxy-3-aminonaphthalene, 1-amino-2-carboxynaphthalene, 2-aminonicotinic acid, 4-aminonicotinic acid, 5-aminonicotinic acid, 6-aminonicotinic acid, 4-aminosalicylic acid, 5-aminosalicylic acid, 6-aminosalicylic acid, ammelide, 2-aminobenzoic acid, 3-aminobenzoic acid, 4-aminobenzoic acid, 2-aminobenzenesulfonic acid, 3-aminobenzenesulfonic acid, 4-aminobenzenesulfonic acid, 3-amino-4,6-dihydroxypyrimidine, 2-aminophenol, 3-aminophenol, 4-aminophenol, 5-amino-8-mercaptoquinoline, 4-amino-8-mercaptoquinoline, 1-mercapto-8-aminonaphthalene, 1-mercapto-7-aminonaphthalene, 1-mercapto-6-aminonaphthalene, 1-mercapto-5-aminonaphthalene, 1-mercapto-4-aminonaphthalene, 1-mercapto-3-aminonaphthalene, 1-mercapto-2-aminonaphthalene, 1-amino-7-mercaptonaphthalene, 2-mercapto-7-aminonaphthalene, 2-mercapto-6-aminonaphthalene, 2-mercapto-5-aminonaphthalene, 2-mercapto-4-aminonaphthalene, 2-mercapto-3-aminonaphthalene, 1-amino-2-mercaptonaphthalene, 3-amino-4,6-dimercaptopyrimidine, 2-aminothiophenol, 3-aminothiophenol, 4-aminothiophenol, 2-ethynylaniline, 3-ethynylaniline, 4-ethynylaniline, 2,4-diethynylaniline, 2,5-diethynylaniline, 2,6-diethynylaniline, 3,4-diethynylaniline, 3,5-diethynylaniline, 1-ethynyl-2-aminonaphthalene, 1-ethynyl-3-aminonaphthalene, 1-ethynyl-4-aminonaphthalene, 1-ethynyl-5-aminonaphthalene, 1-ethynyl-6-aminonaphthalene, 1-ethynyl-7-aminonaphthalene, 1-ethynyl-8-aminonaphthalene, 2-ethynyl-1-aminonaphthalene, 2-ethynyl-3-aminonaphthalene, 2-ethynyl-4-aminonaphthalene, 2-ethynyl-5-aminonaphthalene, 2-ethynyl-6-aminonaphthalene, 2-ethynyl-7-aminonaphthalene, 2-ethynyl-8-aminonaphthalene, 3,5-diethynyl-1-aminonaphthalene, 3,5-diethynyl-2-aminonaphthalene, 3,6-diethynyl-1-aminonaphthalene, 3,6-diethynyl-2-aminonaphthalene, 3,7-diethynyl-1-aminonaphthalene, 3,7-diethynyl-2-aminonaphthalene, 4,8-diethynyl-1-aminonaphthalene, and 4,8-diethynyl-2-aminonaphthalene. One of these monoamines may be used singly, or two or more of them may be used in combination.

On the other hand, examples of the monohydric alcohol to be used as the capping agent for the acid anhydride group terminal include, but are not limited to, methanol, ethanol, 1-propanol, 2-propanol, 1-butanol, 2-butanol, 1-pentanol, 2-pentanol, 3-pentanol, 1-hexanol, 2-hexanol, 3-hexanol, 1-heptanol, 2-heptanol, 3-heptanol, 1-octanol, 2-octanol, 3-octanol, 1-nonanol, 2-nonanol, 1-decanol, 2-decanol, 1-undecanol, 2-undecanol, 1-dodecanol, 2-dodecanol, 1-tridecanol, 2-tridecanol, 1-tetradecanol, 2-tetradecanol, 1-pentadecanol, 2-pentadecanol, 1-hexadecanol, 2-hexadecanol, 1-heptadecanol, 2-heptadecanol, 1-octadecanol, 2-octadecanol, 1-nonadecanol, 2-nonadecanol, 1-icosanol, 2-methyl-1-propanol, 2-methyl-2-propanol, 2-methyl-1-butanol, 3-methyl-1-butanol, 2-methyl-2-butanol, 3-methyl-2-butanol, 2-propyl-1-pentanol, 2-ethyl-1-hexanol, 4-methyl-3-heptanol, 6-methyl-2-heptanol, 2,4,4-trimethyl-1-hexanol, 2,6-dimethyl-4-heptanol, isononyl alcohol, 3,7-dimethyl-3-octanol, 2,4-dimethyl-1-heptanol, 2-heptylundecanol, ethylene glycol monoethyl ether, ethylene glycol monomethyl ether, ethylene glycol monobutyl ether, propylene glycol 1-methyl ether, diethylene glycol monoethyl ether, diethylene glycol monomethyl ether, diethylene glycol monobutyl ether, cyclopentanol, cyclohexanol, cyclopentanemonomethylol, dicyclopentanemonomethylol, tricyclodecanemonomethylol, norborneol, and terpineol. In addition, one of these monohydric alcohols may be used singly, or two or more of them may be used in combination.

Examples of the acid anhydride, monocarboxylic acid, monoacid chloride compound and monoactive ester compound to be used as the capping agent for the amino group terminal include acid anhydrides such as phthalic anhydride, maleic anhydride, nadic anhydride, cyclohexanedicarboxylic anhydride and 3-hydroxyphthalic anhydride; monocarboxylic acids such as 2-carboxyphenol, 3-carboxyphenol, 4-carboxyphenol, 2-carboxythiophenol, 3-carboxythiophenol, 4-carboxythiophenol, 1-hydroxy-8-carboxynaphthalene, 1-hydroxy-7-carboxynaphthalene, 1-hydroxy-6-carboxynaphthalene, 1-hydroxy-5-carboxynaphthalene, 1-hydroxy-4-carboxynaphthalene, 1-hydroxy-3-carboxynaphthalene, 1-hydroxy-2-carboxynaphthalene, 1-mercapto-8-carboxynaphthalene, 1-mercapto-7-carboxynaphthalene, 1-mercapto-6-carboxynaphthalene, 1-mercapto-5-carboxynaphthalene, 1-mercapto-4-carboxynaphthalene, 1-mercapto-3-carboxynaphthalene, 1-mercapto-2-carboxynaphthalene, 2-carboxybenzenesulfonic acid, 3-carboxybenzenesulfonic acid, 4-carboxybenzenesulfonic acid, 2-ethynylbenzoic acid, 3-ethynylbenzoic acid, 4-ethynylbenzoic acid, 2,4-diethynylbenzoic acid, 2,5-diethynylbenzoic acid, 2,6-diethynylbenzoic acid, 3,4-diethynylbenzoic acid, 3,5-diethynylbenzoic acid, 2-ethynyl-1-naphthoic acid, 3-ethynyl-1-naphthoic acid, 4-ethynyl-1-naphthoic acid, 5-ethynyl-1-naphthoic acid, 6-ethynyl-1-naphthoic acid, 7-ethynyl-1-naphthoic acid, 8-ethynyl-1-naphthoic acid, 2-ethynyl-2-naphthoic acid, 3-ethynyl-2-naphthoic acid, 4-ethynyl-2-naphthoic acid, 5-ethynyl-2-naphthoic acid, 6-ethynyl-2-naphthoic acid, 7-ethynyl-2-naphthoic acid and 8-ethynyl-2-naphthoic acid, and monoacid chloride compounds in which the carboxyl group of the above monocarboxylic acids is acid-chlorinated; monoacid chloride compounds of dicarboxylic acids such as terephthalic acid, phthalic acid, maleic acid, cyclohexanedicarboxylic acid, 3-hydroxyphthalic acid, 5-norbornene-2,3-dicarboxylic acid, 1,2-dicarboxynaphthalene, 1,3-dicarboxynaphthalene, 1,4-dicarboxynaphthalene, 1,5-dicarboxynaphthalene, 1,6-dicarboxynaphthalene, 1,7-dicarboxynaphthalene, 1,8-dicarboxynaphthalene, 2,3-dicarboxynaphthalene, 2,6-dicarboxynaphthalene and 2,7-dicarboxynaphthalene, in which only a monocarboxyl group is acid-chlorinated; and active ester compounds obtained through reaction between monoacid chloride compounds and N-hydroxybenzotriazole or N-hydroxy-5-norbornene-2,3-dicarboxyimide.

Examples of the dicarbonate ester compound to be used as the capping agent for the amino group terminal include di-tert-butyl dicarbonate, dibenzyl dicarbonate, dimethyl dicarbonate and diethyl dicarbonate.

Examples of the vinyl ether compound to be used as the capping agent for the amino group terminal include butyl vinyl ether, cyclohexyl vinyl ether, ethyl vinyl ether, 2-ethylhexyl vinyl ether, isobutyl vinyl ether, isopropyl vinyl ether, n-propyl vinyl ether, tert-butyl vinyl ether and benzyl vinyl ether.

Examples of other compounds to be used as the capping agent for the amino group terminal include chloroformate esters such as benzyl chloroformate, fluorenylmethyl chloroformate, 2,2,2-trichloroethyl chloroformate, allyl chloroformate, tert-butyl chloroformate, n-butyl chloroformate, isobutyl chloroformate, benzyl chloroformate, allyl chloroformate, ethyl chloroformate and isopropyl chloroformate; isocyanate compounds such as butyl isocyanate, 1-naphthyl isocyanate, octadecyl isocyanate and phenyl isocyanate; benzoyl chloride; methanesulfonic acid chloride; and p-toluenesulfonic acid chloride.

The proportion of the capping agent to be introduced for the acid anhydride group terminal is preferably in the range of 0.1 to 60 mol %, particularly preferably 5 to 50 mol %, and further preferably 5 to 20 mol % relative to the tetracarboxylic dianhydride components represented by the above-described general formulas (1) and (5) which are raw materials of the polyimide resin according to the present invention. In addition, the proportion of the capping agent to be introduced for the amino group terminal is preferably in the range of 0.1 to 100 mol % and particularly preferably 5 to 90 mol % relative to the diamine component. Moreover, by allowing a plurality of end-capping agents to react, a plurality of different end groups may be introduced.

The polyimide resin according to the present invention may contain a polyimide structural unit other than the above-mentioned structural unit represented by general formula (2) and structural unit represented by general formula (3), a structural unit of a polyimide precursor, a polybenzoxazole structural unit and/or a structural unit of a polybenzoxazole precursor.

Photosensitive Resin Composition

Next, a photosensitive resin composition using the polyimide resin according to the present invention as a base resin will be described. In the present invention, by using the above-mentioned polyimide resin according to the present invention as a base resin, a positive photosensitive resin composition and a negative photosensitive resin composition can be obtained.

Positive Photosensitive Resin Composition

At first, among photosensitive resin compositions using the polyimide resin according to the present invention as a base resin, a positive photosensitive resin composition capable of alkaline development will be described. The positive photosensitive resin composition according to the present invention can be, for example, two embodiments, which will be described below, but is not limited to them.

The present invention provides a positive photosensitive resin composition comprising:

(A) a resin comprising structural units represented by the above-described general formulas (2) and (3);

(B) a photosensitizer that generates an acid by light, to increase the dissolution rate in an aqueous alkaline solution, and that is a compound having a quinonediazide structure; and (D) a solvent.

Moreover, the above-described positive photosensitive resin composition can further comprise (C) at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'):

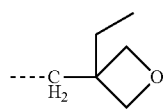

(C-1)

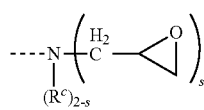

(C-2)

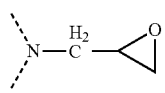

(C-2')

wherein the dotted line represents a bond; $R^c$ represents a linear, branched or cyclic alkyl group having 1 to 6 carbon atoms; and s is 1 or 2.

As stated above, by using the photosensitizer of component (B), upon patterning, the exposed part becomes soluble because its dissolution rate in a developing solution of an aqueous alkaline solution is increased, and the unexposed part is not dissolved due to the alkaline dissolution inhibitory property of the above-described photosensitizer, and therefore, a positive image can be obtained. For the resin comprising structural units represented by the above-described general formulas (2) and (4), the resin itself exhibits alkaline solubility, and therefore, residue such as scum and pattern degradation such as tailing are unlikely to occur at the bottom of the opening pattern, which benefits fine patterning.

First Embodiment

The first embodiment of the positive photosensitive resin composition according to the present invention comprises:

(A) a polyimide resin comprising structural units represented by the above-described general formulas (2) and (3);

(B) a photosensitizer that generates an acid by light, to increase the dissolution rate in an aqueous alkaline solution, and that is a compound having a quinonediazide structure; and (D) a solvent.

From the viewpoint of obtaining alkaline solubility for the positive photosensitive resin composition according to the present invention, when the resin comprising the above-described structural units (2) and (3) has a structural unit represented by the above-described general formula (4), the number of moles of phenolic hydroxy groups in 100 g of component (A) can be mentioned. That is, the number of moles of phenolic hydroxy groups is 0.10 mol to 0.40 mol, further preferably 0.20 mol to 0.35 mol, and most preferably 0.25 mol to 0.35 mol in 100 g of component (A). When the number of moles of phenolic hydroxy groups is 0.10 mol or more, a desired alkaline dissolution rate in a developing solution of an aqueous alkaline solution, can be obtained, and there is no fear of occurrence of failure in the pattern opening upon patterning, scum being observed at the bottom of the pattern, and reduced resolution. On the other hand, the amount of phenolic hydroxy groups in 100 g of component (A) that can be introduced into 100 g of component (A) can be approximately 0.40 mol in the design of the polyimide resin according to the present invention. Upon this, the highest solubility in a developing solution of an aqueous alkaline solution can be expected. Although the photosensitive resin composition according to the present invention can be used to form a cured film by patterning, followed by the post-curing, there is a fear that phenolic hydroxy groups, which are alkaline soluble, remain in this cured film in a large amount, and there is a concern that the obtained cured film has impaired resistance to alkaline chemicals. Therefore, the amount of phenolic hydroxy groups to be introduced is preferably a small amount that can exhibit alkaline solubility.

Component (B) in the positive photosensitive resin composition according to the present invention is a photosensitizer that generates an acid by light to increase the dissolution rate in an aqueous alkaline solution, and that is a compound having a quinonediazide structure. Examples of component (B) may include compounds having a 1,2-naphthoquinonediazidosulfonyl group in the molecule.

Examples of the compound having a 1,2-naphthoquinonediazidosulfonyl group in the molecule include a compound having a 1,2-naphthoquinonediazidosulfonyl group in the molecule represented by the following general formula (8) or (9), provided that -* represents an attachment point.

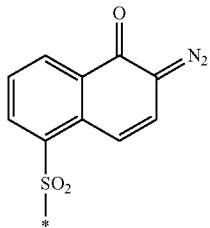
(8)

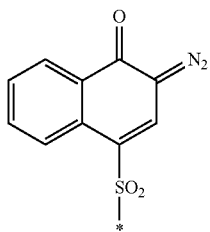
(9)

As a compound to which the above-described 1,2-naphthoquinonediazidosulfonyl group is introduced, specifically, trihydroxybenzophenone or tetrahydroxybenzophenone, a ballast molecule having phenolic hydroxy groups represented by the following general formula (10), or a novolak resin having a repeating unit represented by the formula (15) described later with a weight average molecular weight in the range of 2,000 to 20,000, preferably 3,000 to 10,000 is suitably used. That is, those formed by replacing the hydrogen atom of phenolic hydroxy group of the resin or compound having phenolic hydroxy groups, which will be mentioned below, with the above-described 1,2-naphthoquinonediazidosulfonyl groups are suitably used as component (B).

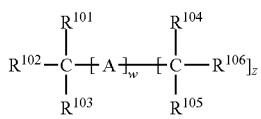
(10)

Here, $R^{101}$ to $R^{106}$ are each independently a hydrogen atom, a methyl group, a group represented by the following formula (11), or a group represented by the following formula (12). w is an integer of 0 to 2, z is an integer of 0 to 2, and when z is 0, w is 1 or 2. (All integer ranges herein are inclusive, e.g., "0 to 2" includes 0, 1, and 2.) When z is 0 and w is 1, A is a hydrogen atom, a methyl group or a group represented by the following formula (11); when z is 0 and w is 2, one A is a methylene group or a group represented by the following formula (13) and the other A is a hydrogen atom, a methyl group or a group represented by the following formula (11); and when z is 1, A is a methylene group or a group represented by the following formula (13). In the case of z being 2, when w is 1, A is a methine group or a group represented by the following formula (14), and when w is 2, one of the As is a methylene group or a group represented by the following formula (13) and the other A is a methine group or a group represented by the following formula (14);

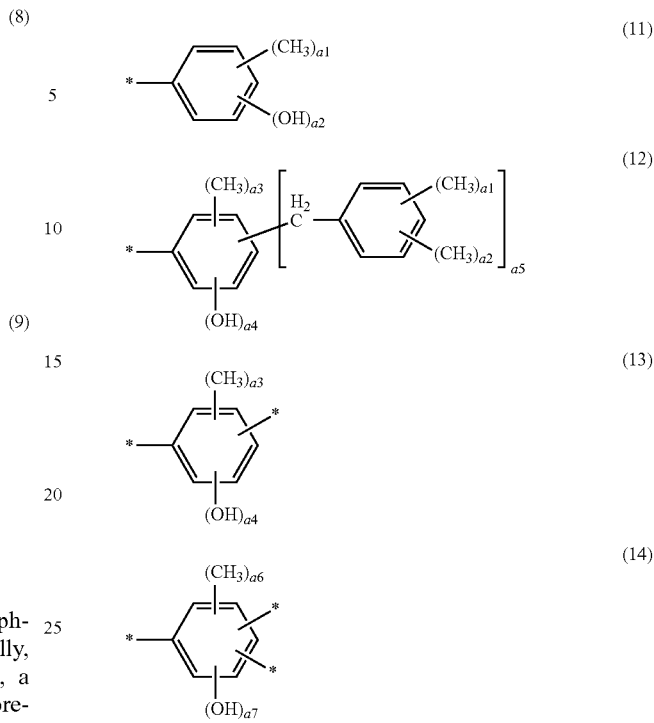

wherein a1, a2, a3, a4, a5, a6 and a7 are each an integer of 0 to 3 provided that a1+a2≤5, a3+a4≤4, and a6+a7≤3.

In this case, in a core structure (ballast molecule) of the above-described formula (10), it is suitable that the number of benzene rings be 2 to 20, more preferably 2 to 10, and further preferably 3 to 6, and that the ratio between the number of phenolic hydroxy groups and the number of benzene rings be 0.5 to 2.5, more preferably 0.7 to 2.0, and further more preferably 0.8 to 1.5.

Specific examples of such a core structure (ballast molecule) include the following (B-1) to (B-44).

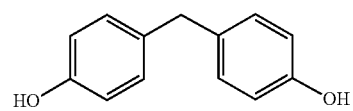
(B-1)

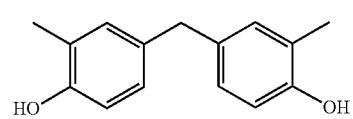
(B-2)

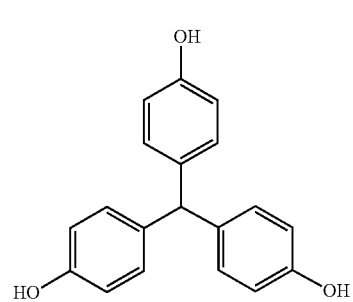
(B-3)

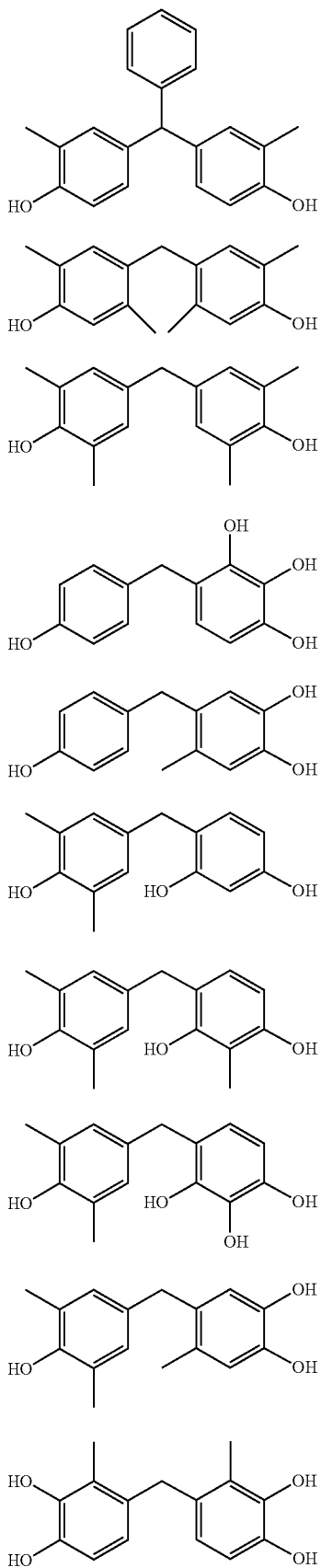
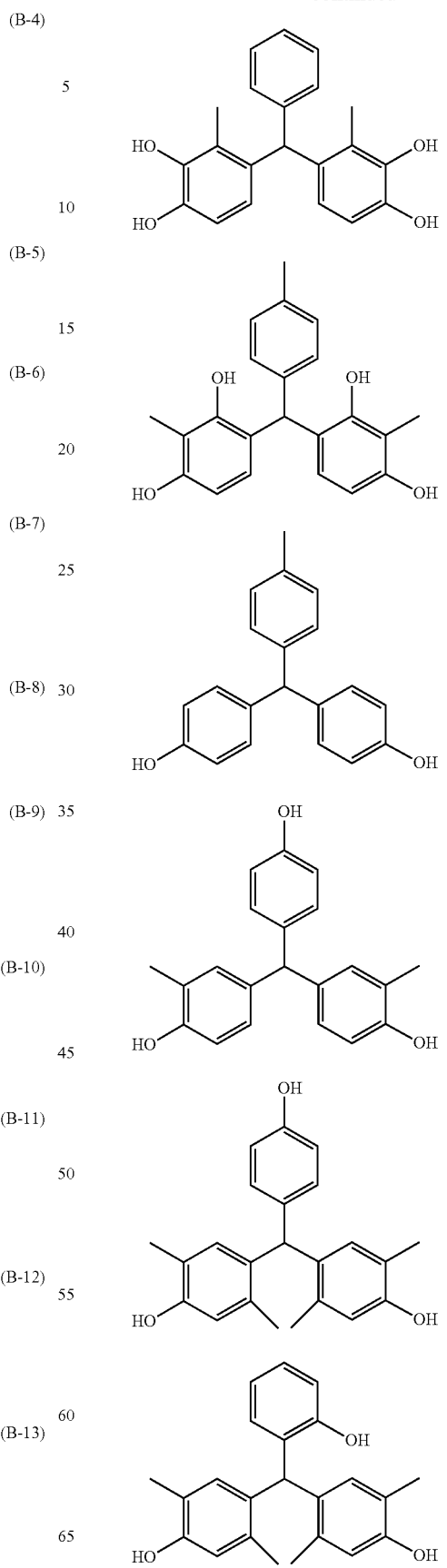

(B-20)
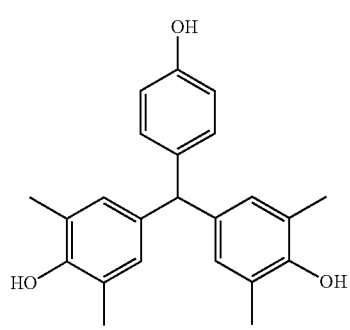
(B-21)
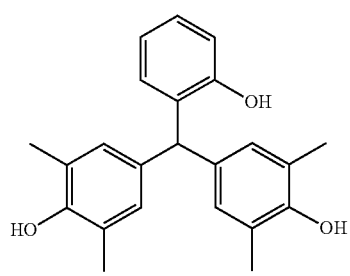
(B-22)
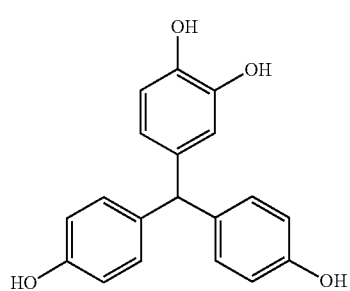
(B-23)
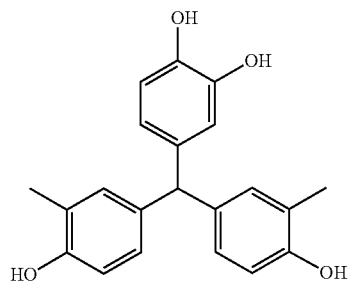
(B-24)
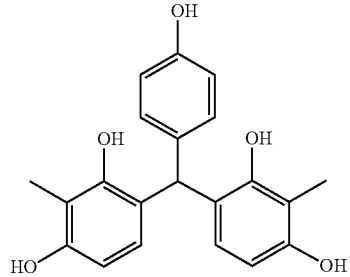
(B-25)
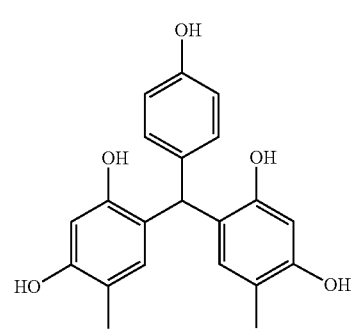
(B-26)
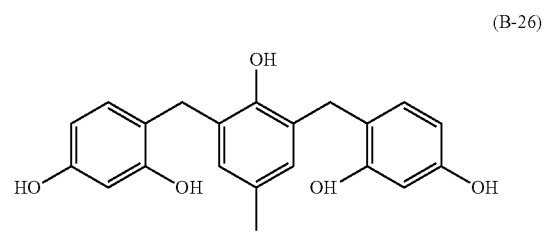
(B-27)
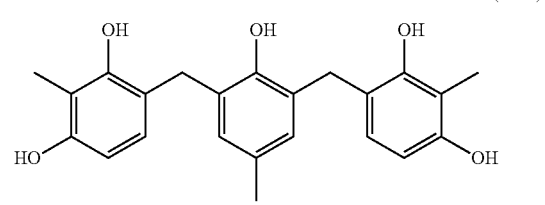
(B-28)
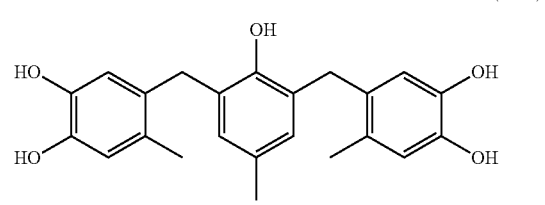
(B-29)
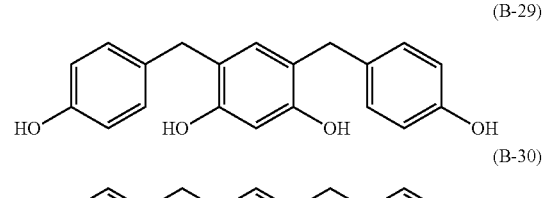
(B-30)
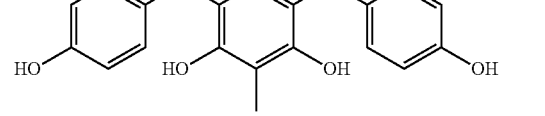
(B-31)
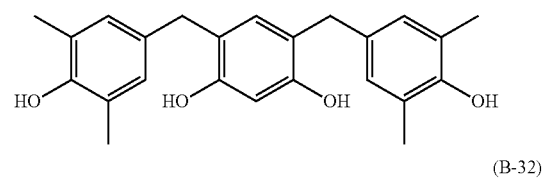
(B-32)
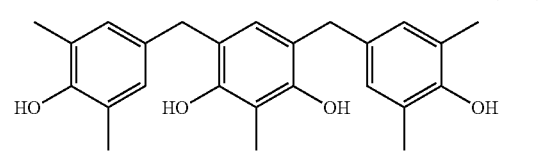

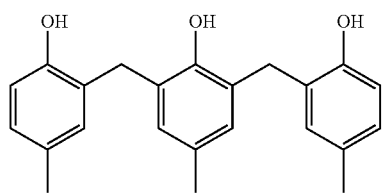
(B-33)
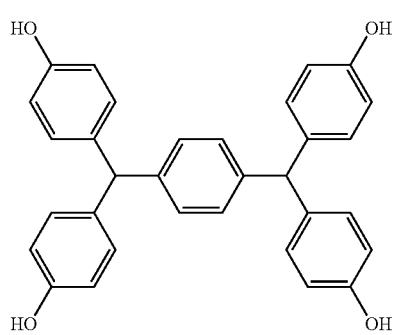
(B-34)
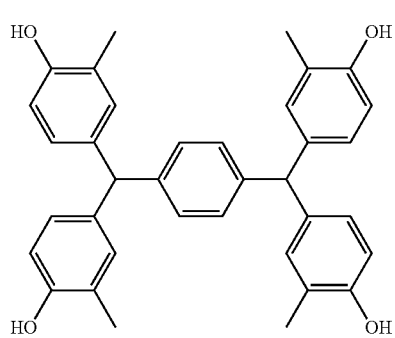
(B-35)
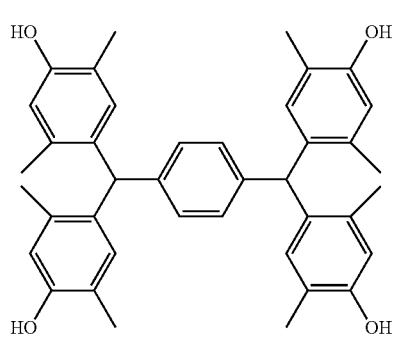
(B-36)
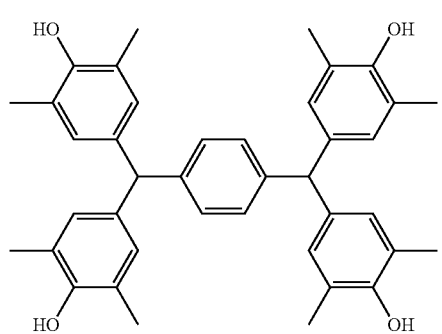
(B-37)
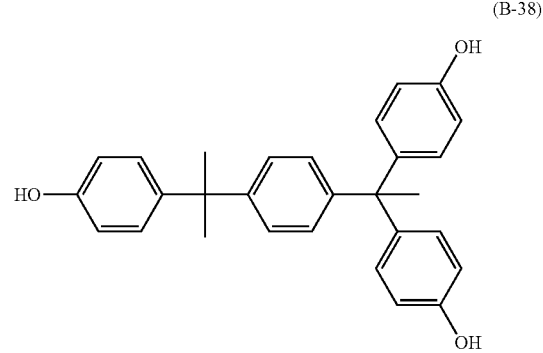
(B-38)
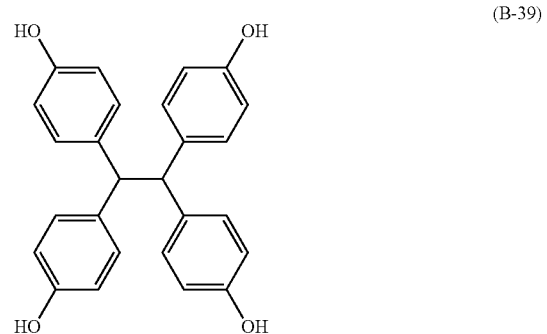
(B-39)
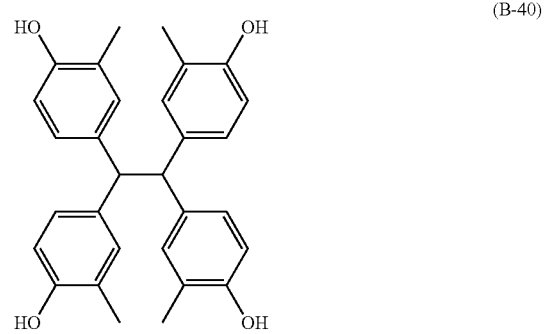
(B-40)
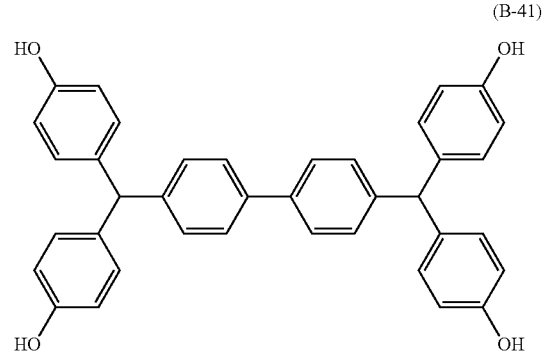
(B-41)

-continued

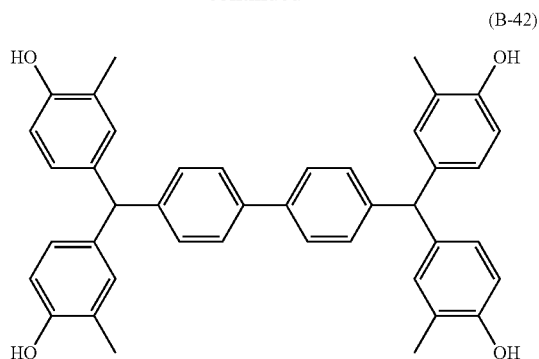
(B-42)

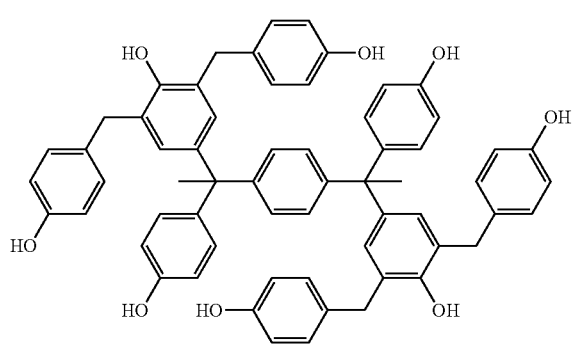
(B-43)

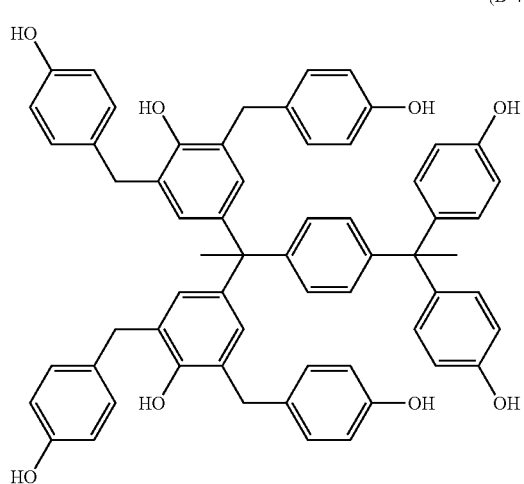
(B-44)

Among the exemplified core structures (ballast molecules) described above, (B-3), (B-29), (B-33), (B-38) and the like are suitably used, and compounds formed by replacing the hydrogen atom of phenolic hydroxy group of these ballast molecules with a 1,2-naphthoquinonediazidosulfonyl group are suitably used as component (B) of the positive photosensitive resin composition according to the present invention.

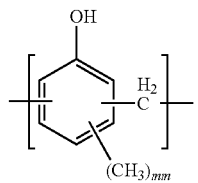
(15)

wherein mm is an integer of 0 to 3.

A novolak resin having a repeating unit represented by the above-described formula (15) can be synthesized by condensing phenols represented by the following formula (16), specifically, at least one phenol such as o-cresol, m-cresol, p-cresol and 3,5-xylenol with aldehydes in a normal manner:

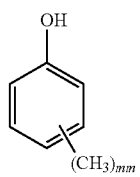
(16)

wherein mm is an integer of 0 to 3.

In this case, examples of the aldehyde include formaldehyde, paraformaldehyde, acetaldehyde and benzaldehyde, but formaldehyde is preferable.

Note that the proportion between phenols represented by the above-described formula (16) and aldehydes is preferably a proportion of 0.2 to 2, particularly 0.3 to 2 in the molar ratio.

As a method of introducing a 1,2-naphthoquinonediazidosulfonyl group to the above-described compound to which the 1,2-naphthoquinonediazidosulfonyl group is introduced, it is preferable to use dehydrochlorination condensation reaction between 1,2-naphthoquinonediazidosulfonyl chloride and the phenolic hydroxy group by a basic catalyst. In the case of the ballast molecule represented by the above-described formula (10), trihydroxybenzophenone or tetrahydroxybenzophenone, the proportion of replacing the hydrogen atom of phenolic hydroxy group with a 1,2-naphthoquinonediazidosulfonyl group is 10 to 100 mol % and preferably 50 to 100 mol %, and in the case of the novolak resin having a repeating unit represented by the above-described formula (15), it is preferable that the proportion of replacing the hydrogen atom of phenolic hydroxy group with a 1,2-naphthoquinonediazidosulfonyl group be 2 to 50 mol % and preferably 3 to 27 mol %.

It is preferable that the amount of component (B) to be added be 1 to 50 parts by mass, and more preferably 10 to 40 parts by mass relative to 100 parts by mass of component (A). In addition, one kind of component (B) or a combination of two or more kinds thereof may be used.

By containing such component (B), before exposure, the solubility in an aqueous alkaline solution is inhibited due to the dissolution inhibitory property of component (B) and the system is thus alkaline insoluble, and upon exposure, the photosensitizer of component (B) generates an acid by light to increase the dissolution rate in an aqueous alkaline solution, thereby making the system alkaline soluble. That is, when an aqueous alkaline solution is used as the developing solution, the unexposed part is not dissolved in the developing solution and the exposed part is soluble in the developing solution, and therefore, a positive pattern can be formed.

Next, component (D) in the positive photosensitive resin composition according to the first embodiment is a solvent. The solvent of component (D) is not specified as long as it can dissolve component (A) and component (B). Examples of the solvent include ketones such as cyclohexanone, cyclopentanone and methyl 2-n-amyl ketone; alcohols such as 3-methoxybutanol, 3-methyl-3-methoxybutanol, 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate and γ-butyrolactone, and one or more of these solvents can be used. In particular, preferable is ethyl lactate, cyclohexanone, cyclopentanone, propylene glycol monomethyl ether acetate, γ-butyrolactone, or a mixed solvent thereof.

The amount of component (D) to be contained is preferably 50 to 2,000 parts by mass and particularly preferably 100 to 1,000 parts by mass relative to 100 parts by mass of the total amount of component (A) and component (B) to be contained.

Second Embodiment

Next, the second embodiment of the positive photosensitive resin composition according to the present invention will be described.

The second embodiment of the positive photosensitive resin composition according to the present invention further comprises, in addition to the above-described positive photosensitive resin composition comprising (A), (B) and (D), (C) at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'):

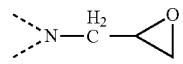

(C-1)

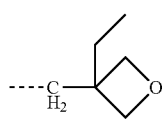

(C-2)

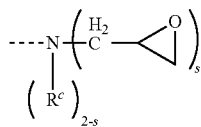

(C-2')

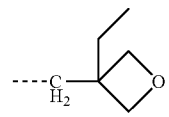

wherein the dotted line represents a bond; $R^c$ represents a linear, branched or cyclic alkyl group having 1 to 6 carbon atoms; and s is 1 or 2.

For component (A) and component (B) of the second embodiment of the positive photosensitive resin composition according to the present invention, those that are the same as the above-mentioned first embodiment of the positive photosensitive resin composition can be suitably used.

Component (C) in the second embodiment of the positive photosensitive resin composition according to the present invention is at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'):

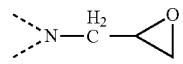

(C-1)

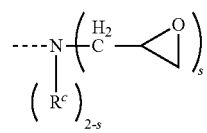

(C-2)

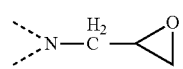

(C-2')

wherein the dotted line represents a bond; $R^c$ represents a linear, branched or cyclic alkyl group having 1 to 6 carbon atoms; and s is 1 or 2.

Examples of the amino condensate modified with formaldehyde or formaldehyde-alcohol include a melamine condensate modified with formaldehyde or formaldehyde-alcohol, or a urea condensate modified with formaldehyde or formaldehyde-alcohol.

In preparation of the above-described melamine condensate modified with formaldehyde or formaldehyde-alcohol, for example, at first, a melamine monomer is modified with formalin for methylolation by a known method, which may be further modified with an alcohol for alkoxylation, thereby obtaining a modified melamine represented by the following general formula (17). Note that the above-described alcohol is preferably a lower alcohol, for example, an alcohol having 1 to 4 carbon atoms.

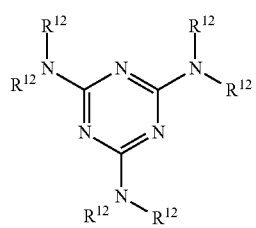

(17)

wherein $R^{12}$ may be the same or different, and each is a methylol group, an alkoxymethyl group including an alkoxy group having 1 to 4 carbon atoms, or a hydrogen atom, but at least one of them is a methylol group or the above-described alkoxymethyl group.

Examples of the above-described $R^{12}$ include, for example, a methylol group, an alkoxymethyl group such as a methoxymethyl group and an ethoxymethyl group, and a hydrogen atom.

Specific examples of the modified melamine represented by the above-described general formula (17) include trimethoxymethylmonomethylolmelamine, dimethoxymethylmonomethylolmelamine, trimethylolmelamine, hexamethylolmelamine and hexamethoxymethylolmelamine. Then, the modified melamine represented by the above-described general formula (17) or a multimer thereof (for example, oligomer such as dimer and trimer) is subjected to addition condensation polymerization with formaldehyde by a conventional method until reaching a desired molecular weight, thereby obtaining a melamine condensate modified with formaldehyde or formaldehyde-alcohol.

In preparation of the above-described urea condensate modified with formaldehyde or formaldehyde-alcohol, for example, a urea condensate with a desired molecular weight is modified with formaldehyde for methylolation by a known method, which may be further modified with an alcohol for alkoxylation. Specific examples of the above-described urea condensate modified with formaldehyde or formaldehyde-alcohol include a methoxymethylated urea condensate, an ethoxymethylated urea condensate and a propoxymethylated urea condensate.

Note that one of these modified melamine condensate and modified urea condensate may be used singly, or two or more of them may be used in combination.

Next, examples of the phenol compound having two or more methylol groups or alkoxymethylol groups on average in one molecule include (2-hydroxy-5-methyl)-1,3-benzenedimethanol, 2,2',6,6'-tetramethoxymethyl bisphenol A, and compounds represented by the following formulas (C-3) to (C-7):

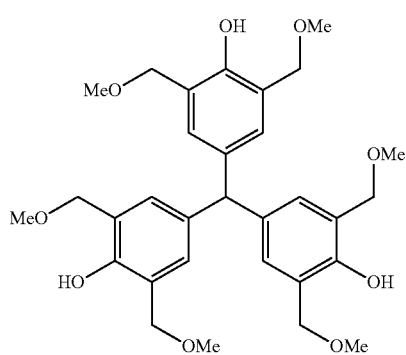

(C-3)

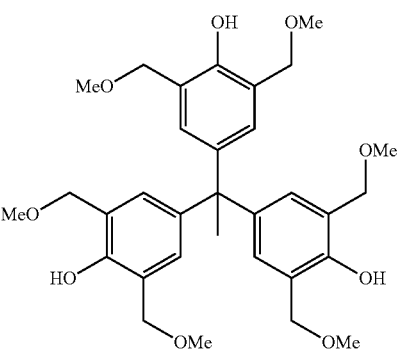

(C-4)

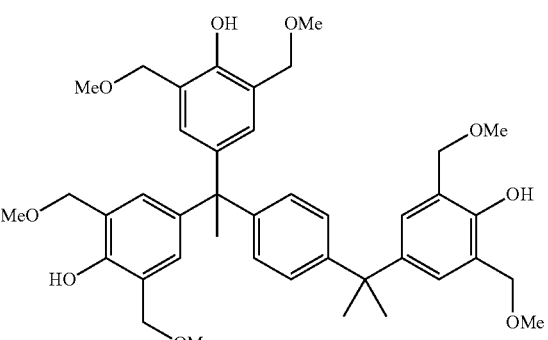

(C-5)

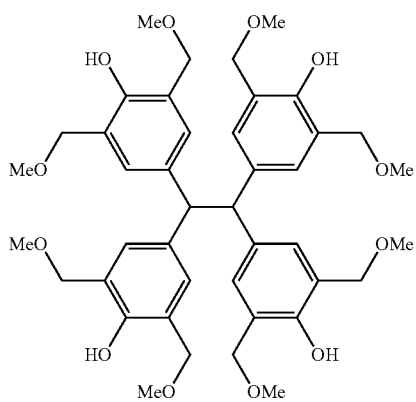

(C-6)

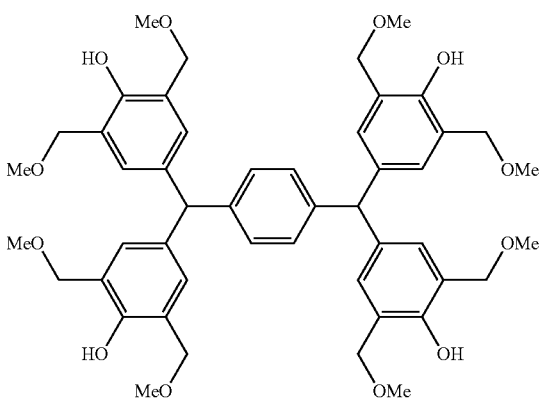

(C-7)

Note that one of the above-described crosslinking agents may be used singly, or two or more of them may be used in combination.

And, examples of the compound in which a hydrogen atom of a hydroxy group of a polyvalent phenol is replaced with a glycidyl group or a group having a glycidyl group may include compounds obtained by allowing hydroxy groups of bisphenol A, tris(4-hydroxyphenyl)methane and 1,1,1-tris(4-hydroxyphenyl)ethane to react with epichlorohydrin in the presence of a base. Suitable examples of the compound in which a hydrogen atom of a hydroxy group of a polyvalent phenol is replaced with a glycidyl group or a group having a glycidyl group may include compounds represented by the following formulas (C-8) to (C-14).

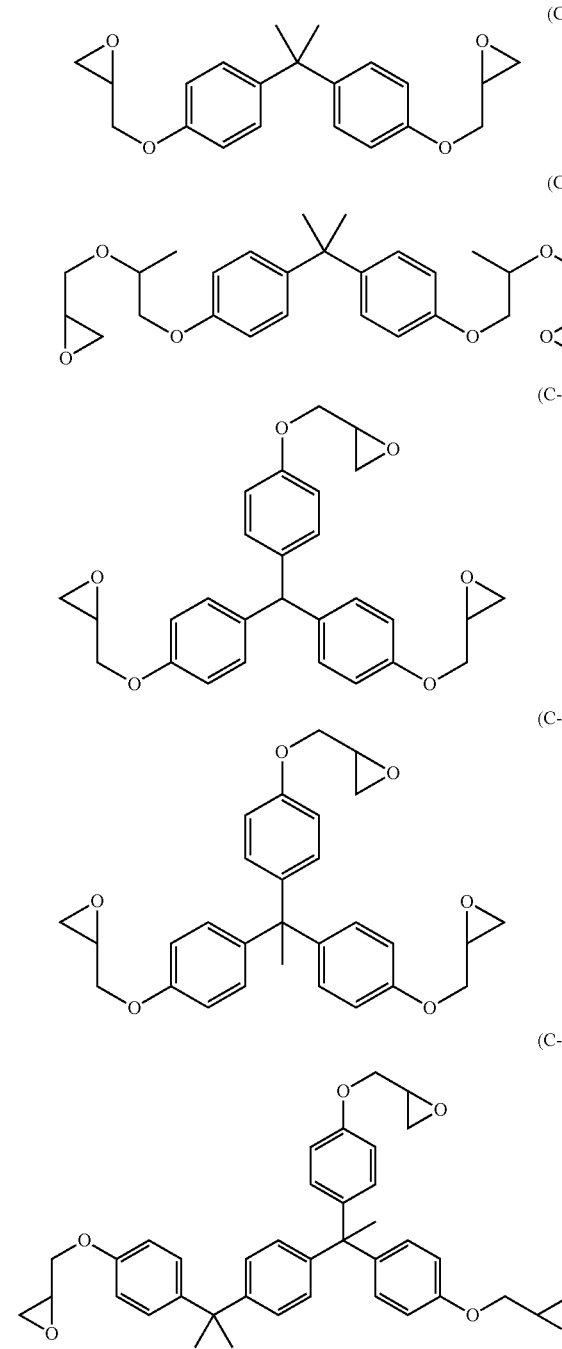

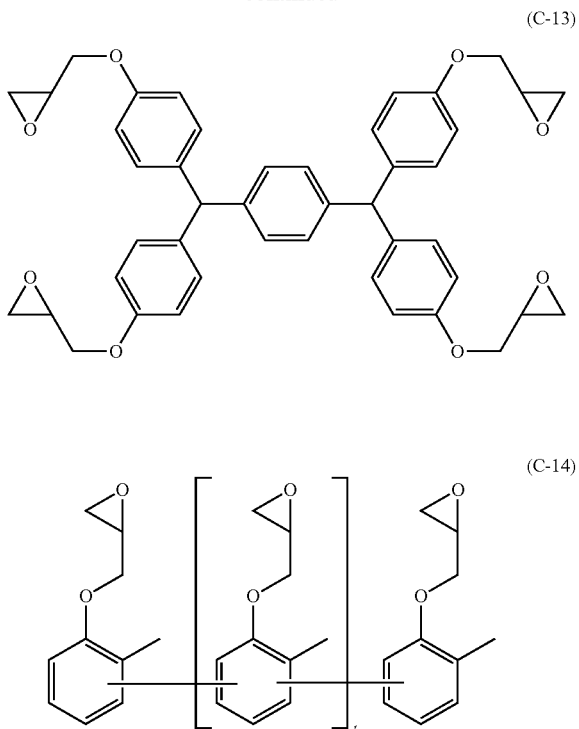

wherein t is $2 \leq t \leq 3$ (where t is not necessarily an integer).

One or two of these compounds in which hydroxy groups of a polyvalent phenol are substituted with, for example, glycidoxy groups may be used as the crosslinking agent.

Examples of the compound in which a hydrogen atom of a hydroxy group of a polyvalent phenol is replaced with a substituent represented by the following formula (C-1) may include a compound containing two or more of the above-described substituents and represented by the following formula (C-15):

wherein the dotted line represents a bond; and

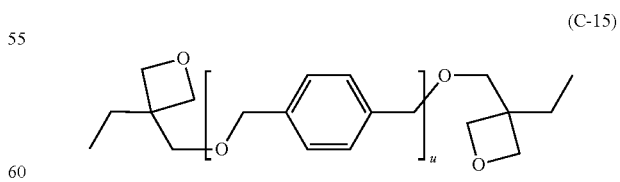

wherein $1 \leq u \leq 3$.

And more, examples of the compound containing two or more groups (nitrogen atoms each having a glycidyl group) represented by the following formula (C-2) may include a compound represented by the following formula (C-16):

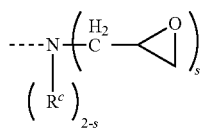 (C-2)

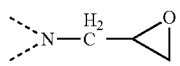 (C-2')

wherein the dotted line represents a bond; $R^c$ represents a linear, branched or cyclic alkyl group having 1 to 6 carbon atoms; and s is 1 or 2; and

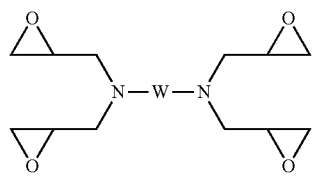 (C-16)

wherein W represents a linear, branched or cyclic alkylene group having 2 to 12 carbon atoms, or a divalent aromatic group.

Examples of the compound represented by the above-described formula (C-16) may include compounds represented by the following formulas (C-17) to (C-20):

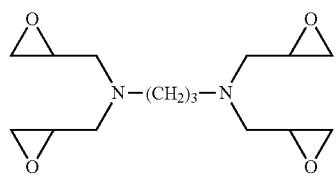 (C-17)

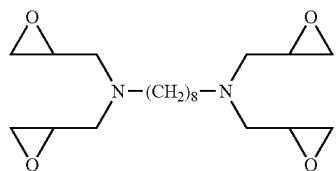 (C-18)

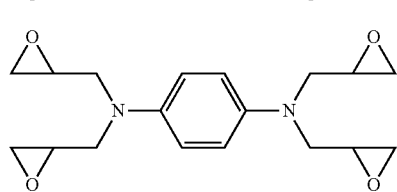 (C-19)

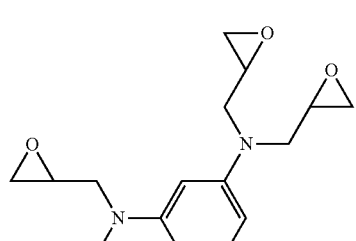 (C-20)

In addition, as the compound containing two or more groups (nitrogen atoms each having a glycidyl group) represented by the above-described formula (C-2'), a compound represented by the following formula (C-21) can be suitably used:

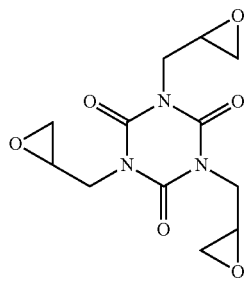 (C-21)

One or two of these compounds containing two or more groups represented by the above-described formula (C-2) or (C-2') may be used as the crosslinking agent.

Component (C) is a component that causes, after the patterning of the positive photosensitive resin composition using a polymer comprising polyimide precursor according to the present invention, crosslinking reaction in the post-curing and further improves the strength of a cured product. The weight average molecular weight of such component (C) is preferably 150 to 10,000 and particularly preferably 200 to 3,000 from the viewpoint of photocurability and heat resistance.

The amount of component (C) to be contained is preferably 0.5 to 50 parts by mass and particularly preferably 1 to 30 parts by mass relative to 100 parts by mass of component (A) in the second embodiment of the positive photosensitive resin composition according to the present invention.

Furthermore, suitable examples of the solvent of component (D) in the second embodiment of the positive photosensitive resin composition according to the present invention may include the same solvents as those described in the first embodiment of the positive photosensitive resin composition.

Other Components

In addition, the positive photosensitive resin composition according to the present invention may further contain components other than component (A), component (B), component (C) and component (D). Examples of the other components may include an adhesion auxiliary and surfactant (E), and as surfactant (E), the compounds recited below and the like can be suitably used.

Surfactant (E) is preferably nonionic, examples thereof include fluorine-based surfactants, specifically, perfluoroalkyl polyoxyethylene ethanols, fluorinated alkyl esters, perfluoroalkylamine oxides and fluorine-containing organosiloxane-based compounds.

For these surfactants, those that are commercially available can be used, and examples thereof include, for example, FLUORAD® "FC-4430" (manufactured by Sumitomo 3M Limited, Tokyo, Japan and 3M Company, St. Paul, Minn., USA), SURFLON™ "S-141" and "S-145" (the above, manufactured by Asahi Glass Co., Ltd., Tokyo, Japan), UNIDYNE® "DS-401", "DS-4031" and "DS-451" (the above, manufactured by Daikin Industries, Ltd., Osaka, Japan), MEGAFAC™ "F-8151" (manufactured by DIC Corporation, Tokyo, Japan) and "X-70-093" (manufactured by Shin-Etsu Chemical Co., Ltd., Tokyo, Japan). Among them, FLUORAD® "FC-4430" (manufactured by Sumitomo 3M Limited, Tokyo, Japan and 3M Company, St. Paul, Minn., USA) and "X-70-093" (manufactured by Shin-Etsu Chemical Co., Ltd., Tokyo, Japan) are preferable.

Negative Photosensitive Resin Composition

Next, among photosensitive resin compositions using the polyimide resin according to the present invention as a base resin, a negative photosensitive resin composition capable of alkaline development will be described. The negative photosensitive resin composition according to the present invention can be, for example, an embodiment to be described below, but is not limited thereto.

The present invention provides a negative photosensitive resin composition comprising:

(A') a resin comprising structural units represented by the above-described general formulas (2) and (3);

(B') a photoacid generator;

(C') at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'):

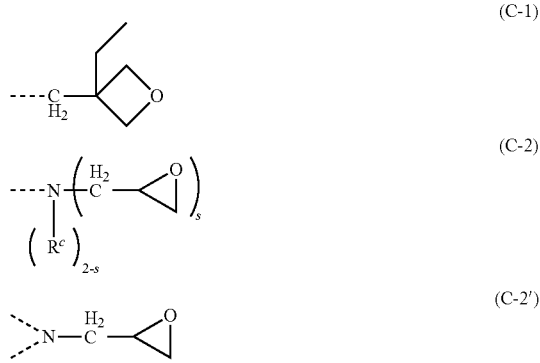

wherein the dotted line represents a bond; $R^c$ represents a linear, branched or cyclic alkyl group having 1 to 6 carbon atoms; and s is 1 or 2; and (D) a solvent.

As stated above, by using the photoacid generator of component (B'), upon patterning, an acid is generated in the exposed part, allowing crosslinking groups of the added crosslinking agent of component (C') and crosslinking reaction points of the polymer to be crosslinked and making the exposed part insoluble in a developing solution, thereby making the composition providing a negative image.

An embodiment of the negative photosensitive resin composition according to the present invention is a negative photosensitive resin composition comprising:

(A') a polyimide resin comprising structural units (2) and (3);

(B') a photoacid generator;

(C') at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydroxy group of a polyvalent phenol is replaced with a substituent represented by the following formula (C-1), and a compound containing two or more groups represented by the following formula (C-2) or (C-2'):

wherein the dotted line represents a bond; $R^c$ represents a linear, branched or cyclic alkyl group having 1 to 6 carbon atoms; and s is 1 or 2; and (D) a solvent.

For component (A') of the negative photosensitive resin composition according to the present invention, a polyimide resin comprising structural unit (5), wherein the resin is the same as the positive photosensitive resin composition mentioned above, can be suitably used.

In the negative photosensitive resin composition according to the present invention, crosslinking groups of component (C') can be crosslinked with the polymer of component (A') using an acid generated from component (B') as a catalyst, thereby forming a negative type photosensitive resin composition.

Component (B') of the negative photosensitive resin composition according to the present invention is a photoacid generator. As the photoacid generator, those that generate an acid by photoirradiation at a wavelength of 190 to 500 nm, which becomes a curing catalyst, can be used. Examples of the photoacid generator include onium salts, diazomethane derivatives, glyoxime derivatives, β-ketosulfone derivatives, disulfone derivatives, nitrobenzylsulfonate derivatives, sulfonate ester derivatives, imid-yl-sulfonate derivatives, oximesulfonate derivatives, iminnosulfonate derivatives and triazine derivatives.

Examples of the above-described onium salt include, for example, a compound represented by the following general formula (18):

 (18)

wherein $R^{13}$ represents a linear, branched or cyclic alkyl group having 1 to 12 carbon atoms, aryl group having 6 to 12 carbon atoms, or aralkyl group having 7 to 12 carbon atoms, optionally having a substituent; $M^+$ represents an iodonium cation or sulfonium cation; $K^-$ represents a non-nucleophilic counter ion; and j is 2 or 3.

In the above-described $R^{13}$, examples of the alkyl group include a methyl group, an ethyl group, a propyl group, a butyl group, a cyclohexyl group, a 2-oxocyclohexyl group, a norbornyl group and an adamantyl group. Examples of the aryl group include, for example, a phenyl group; an alkoxyphenyl group such as o-, m- or p-methoxyphenyl group, ethoxyphenyl group, and m- or p-tert-butoxyphenyl group; and an alkylphenyl group such as 2-, 3- or 4-methylphenyl group, ethylphenyl group, 4-tert-butylphenyl group, 4-butylphenyl group, and dimethylphenyl group. Examples of the aralkyl group include, for example, each group of a benzyl group, a phenethyl group, and the like.

Examples of the non-nucleophilic counter ion of K⁻ include a halide ion such as chloride ion and bromide ion; a fluoroalkylsulfonate such as triflate, 1,1,1-trifluoroethanesulfonate and nonafluorobutanesulfonate; an arylsulfonate such as tosylate, benzenesulfonate, 4-fluorobenzenesulfonate and 1,2,3,4,5-pentafluorobenzenesulfonate; and an alkylsulfonate such as mesylate and butanesulfonate.

Examples of the diazomethane derivative include a compound represented by the following general formula (19):

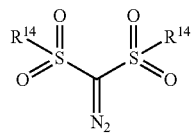

(19)

wherein $R^{14}$ may be the same or different, and each represents a linear, branched or cyclic alkyl group or halogenated alkyl group having 1 to 12 carbon atoms, an aryl group or halogenated aryl group having 6 to 12 carbon atoms, or an aralkyl group having 7 to 12 carbon atoms.

In the above-described $R^{14}$, examples of the alkyl group include a methyl group, an ethyl group, a propyl group, a butyl group, an amyl group, a cyclopentyl group, a cyclohexyl group, a norbornyl group and an adamantyl group. Examples of the halogenated alkyl group include a trifluoromethyl group, a 1,1,1-trifluoroethyl group, a 1,1,1-trichloroethyl group and a nonafluorobutyl group. Examples of the aryl group include a phenyl group; an alkoxyphenyl group such as o-, m- or p-methoxyphenyl group, ethoxyphenyl group, and m- or p-tert-butoxyphenyl group; and an alkylphenyl group such as 2-, 3- or 4-methylphenyl group, ethylphenyl group, 4-tert-butylphenyl group, 4-butylphenyl group, and dimethylphenyl group. Examples of the halogenated aryl group include a fluorophenyl group, a chlorophenyl group and a 1,2,3,4,5-pentafluorophenyl group. Examples of the aralkyl group include, for example, a benzyl group and a phenethyl group.

Specific examples of such a photoacid generator include onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate and diphenyl(4-thiophenoxyphenyl)sulfonium hexafluoroantimonate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane and 1-tert-amylsulfonyl-1-(tert-butylsulfonyl)diazomethane; glyoxime derivatives such as bis-o-(p-toluenesulfonyl)-α-dimethylglyoxime, bis-o-(p-toluenesulfonyl)-α-diphenylglyoxime, bis-o-(p-toluenesulfonyl)-α-dicyclohexylglyoxime, bis-o-(p-toluenesulfonyl)-2,3-pentanedioneglyoxime, bis-(p-toluenesulfonyl)-2-methyl-3,4-pentanedioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexanesulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime and bis-o-(camphorsulfonyl)-α-dimethylglyoxime; oximesulfonate derivatives such as α-(benzenesulfonium oxyimino)-4-methylphenylacetonitrile; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as diphenyldisulfone and dicyclohexyldisulfone; nitrobenzylsulfonate derivatives such as 2,6-dinitrobenzyl p-toluenesulfonate and 2,4-dinitrobenzyl p-toluenesulfonate; sulfonate ester derivatives such as 1,2,3-tris(methanesulfonyloxy)benzene, 1,2,3-tris(trifluoromethanesulfonyloxy)benzene, 1,2,3-tris(p-toluenesulfonyloxy)benzene; imid-yl-sulfonate derivatives such as phthalimid-yl-triflate, phthalimid-yl-tosylate, 5-norbornene 2,3-dicarboxyimid-yl-triflate, 5-norbornene 2,3-dicarboxyimid-yl-tosylate, 5-norbornene 2,3-dicarboxyimid-yl-n-butyl-sulfonate and n-trifluoromethylsulfonyloxynaphthylimide; iminosulfonates such as (5-(4-methylphenyl)sulfonyloxyimino-5H-thiophen-2-ylidene)-(2-methylphenyl)acetonitrile and (5-(4-(4-methylphenylsulfonyloxy)phenylsulfonyloxyimino)-5H-thiophen-2-ylidene)-(2-methylphenyl)-acetonitrile; and 2-methyl-2[(4-methylphenyl)sulfonyl]-1-[(4-methylthio)phenyl]-1-propane. Among them, imid-yl-sulfonates, iminosulfonates, oximesulfonates and the like are suitably used. One of the above-described photoacid generators, or two or more of them can be used.

The amount of the above-described photoacid generator of component (B') to be contained is preferably 0.05 to 20 parts by mass and particularly preferably 0.2 to 5 parts by mass relative to 100 parts by mass of component (A') in the negative photosensitive resin composition according to the present invention from the viewpoint of photoabsorption of the photoacid generator itself and photocurability in a thick film.

As component (C') of the negative photosensitive resin composition according to the present invention, the same crosslinking agents as component (C) described in the second embodiment of the positive photosensitive resin composition can be preferably used.

As mentioned above, component (C') of the negative photosensitive resin composition according to the present invention is a component that not only can form a negative type pattern by using an acid generated from component (B') as a catalyst to crosslink the crosslinking groups of component (C') with the polymer of component (A'), but also causes crosslinking reaction in the post-curing after the patterning, thereby further improving the strength of a cured product. The weight average molecular weight of such component (C') is preferably 150 to 10,000 and more preferably 200 to 3,000 from the viewpoint of photocurability and heat resistance.

The amount of component (C') to be contained is preferably 0.5 to 50 parts by mass and particularly preferably 1 to 30 parts by mass relative to 100 parts by mass of component (A) in the negative photosensitive resin composition according to the present invention.

Component (D) in the negative photosensitive resin composition according to the present invention is a solvent. The solvent of component (D) is not specified as long as it can dissolve component (A'), component (B') and component (C'). Examples of component (D) may include those that are the same as the solvents recited in the above-described first embodiment or second embodiment of the positive photosensitive resin composition.

The negative photosensitive resin composition according to the present invention may also further contain components other than component (A'), component (B'), component (C') and component (D). Examples of the other components may include (F) a sensitizer, an adhesion auxiliary, a polymerization inhibitor to enhance storage stability, and (E) a surfactant commonly used for improving coating property. As the surfactant of (E), the surfactants recited in the positive photosensitive resin compositions can be preferably used.

Examples of the sensitizer (F) include 7-N,N-diethylaminocoumarin, 7-diethylamino-3-thenonylcoumarin, 3,3'-carbonylbis(7-N,N-diethylamino)coumarin, 3,3'-carbonylbis(7-N,N-dimethoxy)coumarin, 3-thienylcarbonyl-7-N,N-diethylaminocoumarin, 3-benzoylcoumarin, 3-benzoyl-7-N,N-methoxycoumarin, 3-(4'-methoxybenzoyl)coumarin, 3,3'-carbonylbis-5,7-(dimethoxy)coumarin, benzalacetophenone, 4'-N,N-dimethylaminobenzalacetophenone, 4'-acetaminobenzal-4-methoxyacetophenone, dimethylaminobenzophenone, diethylaminobenzophenone, and 4,4'-bis(N-ethyl, N-methyl)benzophenone. The content thereof is preferably 0.05 to 20 parts by mass, and more preferably 0.1 to 10 parts by mass relative to 100 parts by mass of the polymer of polyimide precursor according to the present invention.

In addition, in the negative photosensitive resin composition according to the present invention, a basic compound can be added as component (G), as necessary. As this basic compound, suitable is a compound that can inhibit a diffusion rate of the acid generated from the photoacid generator to be diffused in the resist film. Then, by containing the above-described basic compound, resolution can be improved, change in sensitivity after exposure can be prevented, substrate dependency or environment dependency can be reduced, and exposure margin, pattern shape or the like can be improved.

Examples of the above-described basic compound may include ammonia, primary, secondary and tertiary aliphatic amines, hybrid amines, aromatic amines, hetrocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, alcoholic nitrogen-containing compounds, amide derivatives and imide derivatives, as well as compounds represented by the following general formula (20):

$$N(\alpha)_p(\beta)_{3-p} \qquad (20)$$

wherein p=1, 2 or 3. The side chain α may be the same or different, and can be any of the substituents represented by the following general formulas (21) to (23). The side chain β may be the same or different, and represents a hydrogen atom, or a linear, branched or cyclic alkyl group having 1 to 20 carbon atoms, which may contain an ether bond or a hydroxyl group. In addition, the side chain α may be bonded to each other to form a ring.

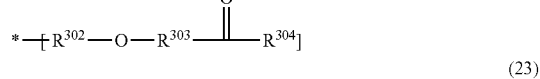
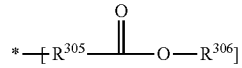

Here, $R^{300}$, $R^{302}$ and $R^{305}$ are each a linear or branched alkylene group having 1 to 4 carbon atoms, and $R^{301}$ and $R^{304}$ are each a hydrogen atom or a linear, branched or cyclic alkyl group having 1 to 20 carbon atoms, each of which may contain one or more hydroxyl groups, ether bonds, ester bonds or lactone rings. $R^{303}$ is a single bond or a linear or branched alkylene group having 1 to 4 carbon atoms, and $R^{306}$ is a linear, branched or cyclic alkyl group having 1 to 20 carbon atoms, each of which may contain one or more hydroxyl groups, ether bonds, ester bonds or lactone rings. Note that *- represents an attachment point.

Examples of the primary aliphatic amine include methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of the secondary aliphatic amine include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Examples of the tertiary aliphatic amine include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of the hybrid amine include, for example, dimethylethylamine, methylethylpropylamine, benzylamine, phenethyl amine, and benzyldimethylamine.

Examples of the aromatic amine and the heterocyclic amine include aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine and the like), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, N-methylpyrrole and the like), oxazole derivatives (for example, oxazole, isoxazole and the like), thiazole derivatives (for example, thiazole, isothiazole and the like), imidazole derivatives (for example, imidazole, 4-methylimidazole, 4-methyl-2-phenylimidazole and the like), pyrazole derivatives, furazan derivatives, pyrroline derivatives (for example, pyrroline, 2-methyl-1-pyrroline and the like), pyrrolidine derivatives (for example, pyrrolidine, N-methylpyrrolidine, pyrrolidinone, N-methylpyrrolidone and the like), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, dimethylaminopyridine and the like), pyridazine derivatives, pyrimidine derivatives, pyrazine derivatives, pyrazoline derivatives, pyrazolidine derivatives, piperidine derivatives, piperadine derivatives, morpholine derivatives, indole derivatives, isoindole derivatives, 1H-indazole derivatives, indoline derivatives, quinoline derivatives (for example, quinoline, 3-quinolinecarbonitrile and the like), isoquinoline derivatives, cinnoline derivatives, quinazoline derivatives, quinoxaline derivatives, phthalazine derivatives, purine derivatives, puteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of the nitrogen-containing compound having a carboxyl group include aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, methoxyalanine and the like).

Examples of the nitrogen-containing compound having a sulfonyl group include 3-pyridinesulfonic acid and pyridinium p-toluenesulfonate.

Examples of the nitrogen-containing compound having a hydroxyl group, the nitrogen-containing compound having a hydroxyphenyl group and the alcoholic nitrogen-containing compound include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperadine, 1-[2-(2-hydroxyethoxy)ethyl]piperadine, piperidineethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidineethanol, 1-aziridineethanol, N-(2-hydroxyethyl)phthalimide, and N-(2-hydroxyethyl)isonicotinamide.

Examples of the amide derivative include formamide, N-methylformamide, N,N-dimethylformamide, acetamide, N-methylacetamide, N,N-dimethylacetamide, propionamide, and benzamide. Examples of the imide derivative include, for example, phthalimide, succinimide, and maleimide.

Examples of the compound represented by the above-described general formula (20) may include, but are not limited to, tris[2-(methoxymethoxy)ethyl]amine, tris[2-(2-methoxyethoxy)ethyl]amine, tris[2-(2-methoxyethoxymethoxy)ethyl]amine, tris[2-(1-methoxyethoxy)ethyl]amine, tris[2-(1-ethoxyethoxy)ethyl]amine, tris[2-(1-ethoxyoxopropoxy)ethyl]amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)2-(methoxycarbonyl)ethylamine, N,N-bis(2-acetoxyethyl)2-(methoxycarbonyl)ethylamine, N,N-bis(2-hydroxyethyl)2-(ethoxycarbonyl)ethylamine, N,N-bis(2-acetoxyethyl)2-(ethoxycarbonyl)ethylamine, N,N-bis(2-hydroxyethyl)2-(2-methoxyethoxycarbonyl)ethylamine, N,N-bis(2-acetoxyethyl)2-(2-methoxyethoxycarbonyl)ethylamine, N,N-bis(2-hydroxyethyl)2-(2-hydroxyethoxycarbonyl)ethylamine, N,N-bis(2-acetoxyethyl)2-(2-acetoxyethoxycarbonyl)ethylamine, N,N-bis(2-hydroxyethyl)2-[(methoxycarbonyl)methoxycarbonyl]ethylamine, N,N-bis(2-acetoxyethyl)2-[(methoxycarbonyl)methoxycarbonyl]ethylamine, N,N-bis(2-hydroxyethyl)2-(2-oxopropoxycarbonyl)ethylamine, N,N-bis(2-acetoxyethyl)2-(2-oxopropoxycarbonyl)ethylamine, N,N-bis(2-hydroxyethyl)2-(tetrahydrofurfuryloxycarbonyl)ethylamine, N,N-bis(2-acetoxyethyl)2-(tetrahydrofurfuryloxycarbonyl)ethylamine, N,N-bis(2-hydroxyethyl)2-[(2-oxotetrahydrofuran-3-yl)oxycarbonyl]ethylamine, N,N-bis(2-acetoxyethyl)2-[(2-oxotetrahydrofuran-3-yl)oxycarbonyl]ethylamine, N,N-bis(2-hydroxyethyl)2-(4-hydroxybutoxycarbonyl)ethylamine, N,N-bis(2-formyloxyethyl)2-(4-formyloxybutoxycarbonyl)ethylamine, N,N-bis(2-formyloxyethyl)2-(2-formyloxyethoxycarbonyl)ethylamine, N,N-bis(2-methoxyethyl)2-(methoxycarbonyl)ethylamine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl]amine, N-(2-methoxyethyl)bis[2-(methoxycarbonyl)ethyl]amine, N-butylbis[2-(methoxycarbonyl)ethyl]amine, N-butylbise[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, and β-(diethylamino)-δ-valerolactone. One of the above-described basic compounds, or two or more of them can be used.

The amount of the above-described basic compound to be contained is preferably 0 to 3 parts by mass and particularly preferably 0.01 to 1 part by mass relative to 100 parts by mass of component (A) in the negative photosensitive resin composition according to the present invention from the viewpoint of sensitivity.

Patterning Method

Furthermore, the present invention provides a patterning method comprising:

(1) applying the positive photosensitive resin composition mentioned above onto a substrate to form a photosensitive material film;

(2) heating the photosensitive material film;

(3) exposing the photosensitive material film with a high energy beam having a wavelength of 190 to 500 nm or an electron beam through a photomask; and (4) developing the film with a developing solution of an aqueous alkaline solution.

As stated above, in the positive photosensitive resin composition according to the present invention, alkaline development with an aqueous alkaline solution is possible.

Further, the present invention provides a patterning method comprising:

(I) applying the negative photosensitive resin composition mentioned above onto a substrate to form a photosensitive material film;

(II) heating the photosensitive material film;

(III) exposing the photosensitive material film with a high energy beam having a wavelength of 190 to 500 nm or an electron beam through a photomask; and (IV) developing the film with a developing solution of an aqueous alkaline solution.

When the base resin for the negative photosensitive resin composition according to the present invention comprises a structural unit represented by the above-described general formula (4), good alkaline development with an aqueous alkaline solution is possible.

Upon this, it is preferable that the patterning method comprise a post-exposure heating step between step (III) and step (IV).

In particular, in the case of a negative photosensitive resin composition comprising a polymer containing a resin that comprises structural units represented by the above-described general formulas (2) and (4), when heating following the exposure (post-exposure bake (PEB)) is included, crosslinking reaction between crosslinking groups of the crosslinking agent and crosslinking reaction points of the polymer can be accelerated by an acid generated from the photoacid generator through the exposure as a catalyst.

Next, a patterning method using the positive photosensitive resin composition and negative photosensitive resin composition according to the present invention will be described.

In the case of either positive photosensitive resin composition or negative photosensitive resin composition according to the present invention, formation of a pattern may be carried out by employing a known lithography technology, and for example, by coating the photosensitive resin composition onto a silicon wafer or a $SiO_2$ substrate, a SiN substrate, or a substrate onto which a pattern of copper wiring or the like has been formed with a spin coating technique (spin coating method) and pre-baking under conditions of 80 to 130° C. for 50 to 600 seconds to form a photosensitive material film with a thickness of 1 to 50 μm, preferably 1 to 30 μm, more preferably 5 to 20 μm.

In the spin coating method, the photosensitive resin composition can be coated onto the silicon substrate by dispensing the photosensitive resin composition onto the substrate in an amount of approximately 5 mL, and then rotating the substrate. Upon this, the film thickness of the photosensitive material film on the substrate can be readily controlled by adjusting the rotation speed.

Then, the remaining solvent can be removed by pre-baking.

Then, a mask for forming the target pattern is put on the photosensitive material film, and a high energy beam such as i-line and g-line having a wavelength of 190 to 500 nm or an electron beam is irradiated thereto with an exposure value of approximately 1 to 5,000 $mJ/cm^2$ and preferably approximately 100 to 2,000 $mJ/cm^2$.

Next, as necessary, heating treatment after the exposure (post-exposure bake (PEB)) may be carried out on a hot plate at 60 to 150° C. for 1 to 10 minutes, preferably at 80 to 120° C. for 1 to 5 minutes.

Thereafter, development is performed. In the above-described first embodiment and second embodiment of the positive photosensitive resin composition, and the negative photosensitive resin composition according to the present invention, either composition allows alkaline development with an aqueous alkaline solution.

On the other hand, a suitable aqueous alkaline solution that can be used for the alkaline development is a 2.38% aqueous solution of tetramethylammonium hydroxide (TMAH). The development can be carried out by normal methods such as spray method and paddle method, or by dipping the film in a developing solution. Thereafter, by carrying out washing, rinsing, drying and the like, as necessary, a resist film having a desired pattern can be obtained.

Furthermore, the present invention provides a method of forming a cured film, comprising heating and post-curing a patterned film obtained by the patterning methods mentioned above at a temperature of 100 to 300° C.

That is, by heating and post-curing the patterned film obtained by the above-described patterning method at a temperature of 100 to 300° C., preferably 150 to 300° C., and further preferably 180 to 250° C., using an oven or a hot plate, a cured film can be formed. When the post-curing temperature is 100 to 300° C., the crosslinking density of the film of the photosensitive resin composition can be increased and the remaining volatile components can be removed, which is preferable from the viewpoint of adhesiveness to the substrate, heat resistance and strength, as well as electrical properties. Also, the post-curing time can be 10 minutes to 10 hours.

In addition, the present invention provides an interlayer insulating film comprising a cured film formed by curing the above-mentioned positive photosensitive resin composition or negative photosensitive resin composition.

The formed pattern described above is used as a protective film (interlayer insulating film) that covers a wiring, circuit, substrate and the like, and such a formed pattern and protective film exhibits excellent adhesiveness to wirings to be covered, to a metal layer of a circuit such as Cu, on a metal electrode existing on the substrate, or on an insulating substrate such as SiN existing in wirings or circuits to be coated, or the like while having an excellent insulating property, and can also significantly improve the resolution performance for realizing further finer patterning while maintaining the appropriate mechanical strength as a protective film.

In addition, the present invention provides a surface protective film comprising a cured film formed by curing the above-mentioned positive photosensitive resin composition or negative photosensitive resin composition.

The cured film obtained as mentioned above is excellent in adhesiveness to a substrate and the like, heat resistance, electrical properties, mechanical strength and chemical resistance to an alkaline stripping solution or the like, and a semiconductor element using the cured film as a protective film is also excellent in reliability. In particular, the cured film can prevent cracking upon a temperature cycle test, and therefore, it is suitably used as a surface protective film for electrical and electronic components, semiconductor elements and the like.

The above-described protective film (interlayer insulating film, surface protective film) is effective for an insulating film for semiconductor elements including a rewiring application, an insulating film for multilayer printed circuit boards, a solder mask, a coverlay film application and the like due to its heat resistance, chemical resistance and insulating property.

That is, the present invention also provides an electronic component having the above-mentioned interlayer insulating film or surface protective film.

The resin according to the present invention comprises structural units represented by the above-described general formulas (2) and (3), and thus has excellent electrical properties, mechanical properties and adhesiveness, and also is soluble in an alkaline developing solution, can form a fine pattern, and can achieve high resolution. Then, the obtained cured film thereof having a pattern can be formed into a protective film for electrical and electronic components and an insulating protective film. In addition, electronic components having that cured film can be provided.

In association with densification and integration of chips, miniaturization of patterns in the rewiring technology for insulating protective films is expected to progress more and more in the future, and photosensitive resin compositions using the polyimide resin according to the present invention can realize high resolution and can meet demands for miniaturization without impairing excellent characteristics such as patterns of the polyimide obtained through heating, as well as mechanical properties, in particular strength, and furthermore adhesiveness of the protective film.

In addition, it has also been strongly desired that insulating protective films that have been subjected to patterning and curing possess heat resistance in a variety of processes and resistance to a variety of chemicals to be used, and the cured film (interlayer insulating film and surface protective film) according to the present invention can meet these demands.

As stated above, the compound and polyimide resin according to the present invention can provide excellent photosensitive resin compositions possessing all of these characteristics without any lack.

EXAMPLES

I. Synthesis Examples

Hereinafter, the present invention will be described specifically with reference to synthesis examples, comparative synthesis examples, examples and comparative examples, but the present invention is not limited by the following examples.

Chemical structural formulas of the compounds used in the following synthesis examples are shown below.

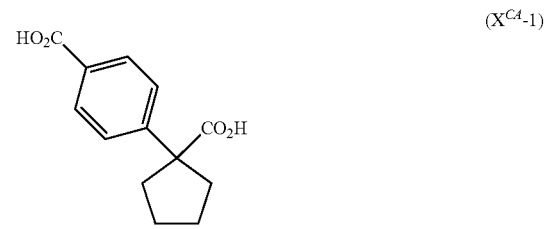

$(X^{CA}\text{-}1)$

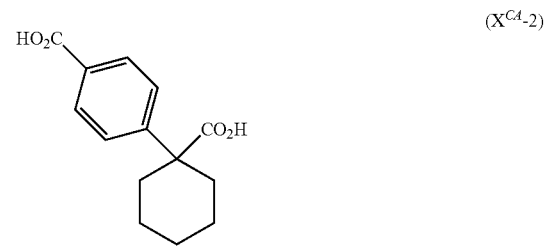

$(X^{CA}\text{-}2)$

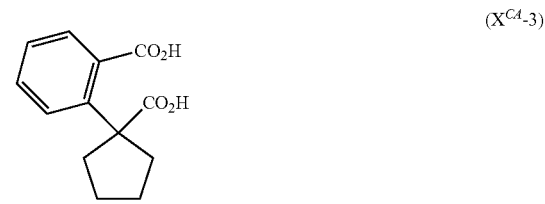

$(X^{CA}\text{-}3)$

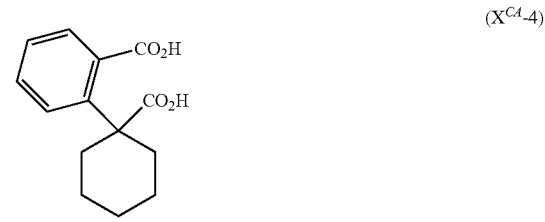

$(X^{CA}\text{-}4)$

Synthesis Example 1

Synthesis of Dicarboxylic Acid ($X^{CA}$-1)

To a mixture of 25 g (143 mmol) of methyl 4-(cyanomethyl)benzoate, 77 g (357 mmol) of 1,4-dibromobutane, and 0.8 g (3.6 mmol) of benzyltriethylammonium chloride, 114 g (1.43 mol) of a 50% aqueous solution of sodium hydroxide was added dropwise under conditions of 70° C., and the reaction was then allowed for 6 hours. The reaction solution was cooled to room temperature, and after removing the liquid portion in the flask, the residual gum-like precipitate was washed with toluene several times. Under ice cooling, 200 mL of a 50% aqueous sulfuric acid solution was added, and the reaction was allowed for 1 week under reflux conditions. The precipitated solid was filtrated, then washed with isopropyl ether, and dried under reduced pressure to obtain 17 g of dicarboxylic acid ($X^{CA}$-1).

Synthesis Example 2

Synthesis of Dicarboxylic Acid ($X^{CA}$-2)

In the same formulation as Synthesis Example 1 except that 1,4-dibromobutane was replaced with 82 g of 1,5-dibromopentane, 10 g of dicarboxylic acid ($X^{CA}$-2) was obtained.

Synthesis Example 3

Synthesis of Dicarboxylic Acid ($X^{CA}$-3)

In the same formulation as Synthesis Example 1 except that methyl 4-(cyanomethyl)benzoate was replaced with 25 g of methyl 2-(cyanomethyl)benzoate, 18 g of dicarboxylic acid ($X^{CA}$-3) was obtained.

Synthesis Example 4

Synthesis of Dicarboxylic Acid ($X^{CA}$-4)

In the same formulation as Synthesis Example 2 except that methyl 4-(cyanomethyl)benzoate was replaced with 25 g of methyl 2-(cyanomethyl)benzoate, 12 g of dicarboxylic acid ($X^{CA}$-4) was obtained.

Synthesis Example 5

Synthesis of Diamine ($X^{AM}$-1)

To a mixture of 5 g of dicarboxylic acid ($X^{CA}$-1), 78 mg of N,N-dimethylformamide and 50 g of chloroform, 12.7 g of thionyl chloride was added dropwise, and the mixture was reacted for 24 hours under reflux conditions. To the dicarboxylic acid chloride obtained after distilling off the solvent under reduced pressure, 15 g of methylene chloride was added, and after adding dropwise 43 g of a 2M ammonia-methanol solution thereto, the resultant mixture was stirred at room temperature for 24 hours. By distilling off the solvent under reduced pressure and purifying the obtained crude product by column chromatography, 3.7 g of diamide compound (IM-1) was obtained. To a mixture of diamide compound (IM-1), 4.5 g of 1,3-dibromo-5,5-dimethylhydantoin and 400 mL of methanol, 5.5 g of 1,8-diazabicyclo[5.4.0]undec-7-en was added dropwise, and the resultant mixture was then stirred for 15 minutes under reflux conditions. Then, 4.5 g of 1,3-dibromo-5,5-dimethylhydantoin was further added additionally, and the resultant mixture was stirred for 1 hour. After distilling off the solvent under reduced pressure, 200 g of ethyl acetate and 100 g of water were added and the resultant mixture was stirred. After removing the aqueous layer, the organic layer was washed using water, a saturated aqueous sodium bicarbonate solution and a saturated brine. By distilling off the solvent under reduced pressure and then purifying the obtained crude product by column chromatography, 2.2 g of diamine ($X^{AM}$-1) was obtained.

Synthesis Example 6

Synthesis of Diamine ($X^{AM}$-2)

In the same formulation as Synthesis Example 5 except that dicarboxylic acid ($X^{CA}$-1) was replaced with 5 g of dicarboxylic acid ($X^{CA}$-3) synthesized in Synthesis Example 3, 2.4 g of diamine ($X^{AM}$-2) was obtained.

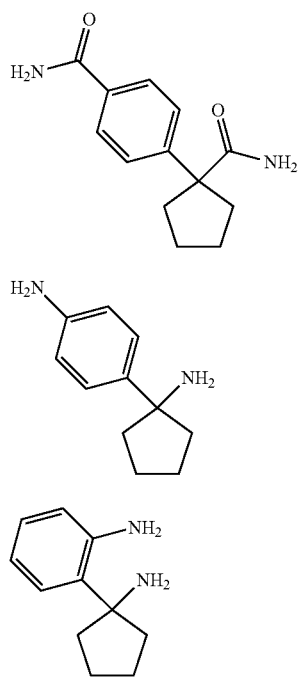

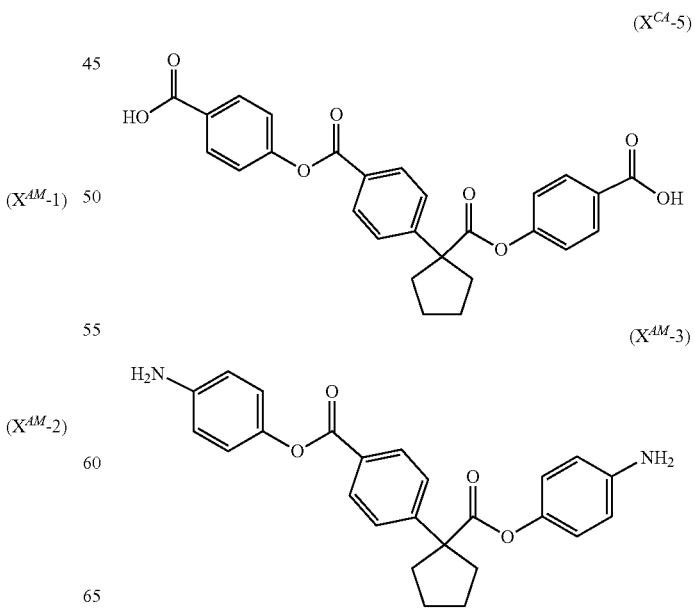

Synthesis Example 7

Synthesis of Dicarboxylic Acid ($X^{CA}$-5)

To the dicarboxylic acid chloride prepared from 5 g of dicarboxylic acid ($X^{CA}$-1) by the same approach as Synthesis Example 5, 6.5 g of 4-hydroxybenzoic acid and 50 g of methylene chloride were added, and the resultant mixture was stirred. After ice cooling the reaction solution, a mixed solution of 11 g of triethylamine, 260 mg of N,N-dimethylaminopyridine and 10 g of methylene chloride was added dropwise thereto, and the reaction was then kept at room temperature for 24 hours. The reaction was stopped by adding 50 g of a 5% hydrochloric acid. The precipitated solid was collected by filtration, washed with tert-butyl methyl ether, and then dried, thereby obtaining 6 g of dicarboxylic acid ($X^{CA}$-5).

Synthesis Example 8

Synthesis of Diamine ($X^{AM}$-3)

To the dicarboxylic acid chloride prepared from 5 g of dicarboxylic acid ($X^{CA}$-1) by the same approach as Synthesis Example 5, 6.5 g of 4-nitrophenol and 50 g of methylene chloride were added, and the resultant mixture was stirred. After ice cooling the reaction solution, a mixed solution of 11 g of triethylamine, 260 mg of N,N-dimethylaminopyridine and 10 g of methylene chloride was added dropwise thereto, and the reaction was then kept at room temperature for 24 hours. Subsequently, 100 g of diisopropyl ether was added thereto, and the resultant mixture was stirred for 1 hour under ice cooling. The precipitated solid was collected by filtration. The obtained solid was stirred along with 30 g of a saturated aqueous ammonium chloride solution and 7 g of zinc at 60° C. for 24 hours. After ice cooling the reaction solution, 50 g of a 20% hydrochloric acid was added dropwise thereto, and the resultant solution was then stirred for 8 hours to dissolve zinc. The precipitated solid was collected by filtration and then suspended in a saturated aqueous sodium bicarbonate solution. After stirring the suspension for 1 hour, the solid was collected by filtration and washed with ice-cooled acetonitrile several times. By drying the solid under reduced pressure, 4.9 g of diamine ($X^{AM}$-3) was obtained.

Synthesis Example 9

Synthesis of Polyamide-Imide Resin (A-1)

To a 300 ml flask equipped with a stirrer and a thermometer, 10 g (27.3 mmol) of 2,2-bis(3-amino-4-hydroxyphenyl)hexafluoropropane (6FAP), 0.32 g (2.94 mmol) of p-aminophenol and 40 g of N-methyl-2-pyrrolidone were added, and the resultant mixture was stirred at room temperature to make the above compounds dissolved. Separately, to a solution formed by dissolving 1.38 g (5.87 mmol) of dicarboxylic acid ($X^{CA}$-1) synthesized in Synthesis Example 1 in 50 g of N-methyl-2-pyrrolidone, 698 mg (5.87 mmol) of thionyl chloride was added dropwise under ice cooling. After the temperature rose to room temperature, the resultant mixture was stirred for 3 hours to prepare a solution of the dicarboxylic acid chloride. To this solution, 7.29 g (23.5 mmol) of 3,3',4,4'-oxydiphthalic dianhydride (ODPA) was added and dissolved, and the resultant solution was then added dropwise to the previously prepared solution of 2,2-bis(3-amino-4-hydroxyphenyl)hexafluoropropane in N-methyl-2-pyrrolidone. After stirring the resultant mixture at room temperature for 3 hours, 15 g of xylene was added to this reaction solution, and the solution was heated to reflux at 180° C. for 6 hours for removing the generated water out of the system. After cooling this reaction solution to room temperature, it was added dropwise to 650 mL of ultrapure water under stirring, and the precipitate was separated by filtration. After appropriately washing the precipitate with water, by drying it under reduced pressure at 40° C. for 48 hours, polyamide-imide resin (A-1) was obtained. When the molecular weight of this polymer was measured by GPC, it had a weight average molecular weight of 32,000 in terms of polystyrene.

Synthesis Example 10

Synthesis of Polyamide-Imide Resin (A-2)

In the same formulation as Synthesis Example 9 except that dicarboxylic acid ($X^{CA}$-1) was replaced with 1.46 g (5.87 mmol) of dicarboxylic acid ($X^{CA}$-2) obtained in Synthesis Example 2, polyamide-imide resin (A-2) was obtained. When the molecular weight of this polymer was measured by GPC, it had a weight average molecular weight of 33,000 in terms of polystyrene.

Synthesis Example 11

Synthesis of Polyamide-Imide Resin (A-3)

In the same formulation as Synthesis Example 9 except that dicarboxylic acid ($X^{CA}$-1) was replaced with 1.38 g (5.87 mmol) of dicarboxylic acid ($X^{CA}$-3) obtained in Synthesis Example 3, polyamide-imide resin (A-3) was obtained. When the molecular weight of this polymer was measured by GPC, it had a weight average molecular weight of 30,000 in terms of polystyrene.

Synthesis Example 12

Synthesis of Polyamide-Imide Resin (A-4)

In the same formulation as Synthesis Example 9 except that dicarboxylic acid ($X^{CA}$-1) was replaced with 1.46 g (5.87 mmol) of dicarboxylic acid ($X^{CA}$-4) obtained in Synthesis Example 4, polyamide-imide resin (A-4) was obtained. When the molecular weight of this polymer was measured by GPC, it had a weight average molecular weight of 31,000 in terms of polystyrene.

Synthesis Example 13

Synthesis of Polyimide Resin (A-5)

To a 300 ml flask equipped with a stirrer and a thermometer, 10 g (27.3 mmol) of 2,2-bis(3-amino-4-hydroxyphenyl)hexafluoropropane, 1.32 g (7.48 mmol) of diamine ($X^{AM}$-1) synthesized in Synthesis Example 5, 0.41 g (3.74 mmol) of p-aminophenol and 40 g of N-methyl-2-pyrrolidone were added, and the resultant mixture was stirred at room temperature to make the above compounds dissolved. To that solution, a solution formed by dissolving 11.6 g (37.4 mmol) of 3,3',4,4'-oxydiphthalic dianhydride (ODPA) in 50 g of N-methyl-2-pyrrolidone was added dropwise. After stirring the resultant mixture at room temperature for 3 hours, 15 g of xylene was added to this reaction solution, and the solution was heated to reflux at 180° C. for 6 hours for removing the generated water out of the system. After cooling this reaction solution to room temperature, it was added dropwise to 650 mL of ultrapure water under stirring, and the precipitate was separated by filtration. After appropriately washing the precipitate with water, by drying it under reduced pressure at 40° C. for 48 hours, polyimide resin (A-5) was obtained. When the molecular weight of this polymer was measured by GPC, it had a weight average molecular weight of 30,000 in terms of polystyrene.

Synthesis Example 14

Synthesis of Polyimide Resin (A-6)

In the same formulation as Synthesis Example 13 except that diamine ($X^{AM}$-1) was replaced with 1.46 g (5.87 mmol) of diamine ($X^{AM}$-2) obtained in Synthesis Example 6, polyimide resin (A-6) was obtained. When the molecular weight of this polymer was measured by GPC, it had a weight average molecular weight of 30,000 in terms of polystyrene.

Synthesis Example 15

Synthesis of Polyamide-Imide Resin (A-7)

In the same formulation as Synthesis Example 9 except that dicarboxylic acid ($X^{CA}$-1) was replaced with 2.79 g (5.87 mmol) of dicarboxylic acid ($X^{CA}$-5) obtained in Synthesis Example 6, polyamide-imide resin (A-7) was obtained. When the molecular weight of this polymer was measured by GPC, it had a weight average molecular weight of 32,000 in terms of polystyrene.

Synthesis Example 16

Synthesis of Polyimide Resin (A-8)

In the same formulation as Synthesis Example 13 except that diamine ($X^{AM}$-1) was replaced with 3.12 g (7.48 mmol) of diamine ($X^{AM}$-3) obtained in Synthesis Example 7, polyimide resin (A-8) was obtained. When the molecular weight of this polymer was measured by GPC, it had a weight average molecular weight of 31,000 in terms of polystyrene.

Comparative Synthesis Example 1

Synthesis of Polyimide Resin (A-9)

To a 300 ml flask equipped with a stirrer and a thermometer, 10 g (27.3 mmol) of 2,2-bis(3-amino-4-hydroxyphenyl)hexafluoropropane, 0.32 g (2.94 mmol) of p-aminophenol and 40 g of N-methyl-2-pyrrolidone were added, and the resultant mixture was stirred at room temperature to dissolve the above compounds. To 50 g of N-methyl-2-pyrrolidone, 9.11 g (29.4 mmol) of 3,3',4,4'-oxydiphthalic dianhydride (ODPA) was added and dissolved, and the resultant solution was then added dropwise to the previously prepared solution of 2,2-bis(3-amino-4-hydroxyphenyl)hexafluoropropane in N-methyl-2-pyrrolidone. After stirring the resultant mixture at room temperature for 3 hours, 15 g of xylene was added to this reaction solution, and the solution was heated to reflux at 180° C. for 6 hours for removing the generated water out of the system. After cooling this reaction solution to room temperature, it was added dropwise to 650 mL of ultrapure water under stirring, and the precipitate was separated by filtration. After appropriately washing the precipitate with water, by drying it under reduced pressure at 40° C. for 48 hours, polyimide resin (A-9) was obtained. When the molecular weight of this polymer was measured by GPC, it had a weight average molecular weight of 35,000 in terms of polystyrene.

Comparative Synthesis Example 2

Synthesis of Polyamide-Imide Resin (A-10)

In the same formulation as Synthesis Example 9 except that dicarboxylic acid ($X^{CA}$-1) was replaced with 1.43 g (5.87 mmol) of 4,4'-biphenyldicarboxylic acid, polyamide-imide resin (A-10) was obtained. When the molecular weight of this polymer was measured by GPC, it had a weight average molecular weight of 29,000 in terms of polystyrene.

Comparative Synthesis Example 3

Synthesis of Polyamide-Imide Resin (A-11)

In the same formulation as Synthesis Example 9 except that dicarboxylic acid ($X^{CA}$-1) was replaced with 1.19 g (5.87 mmol) of sebacic acid, polyamide-imide resin (A-11) was obtained. When the molecular weight of this polymer was measured by GPC, it had a weight average molecular weight of 34,000 in terms of polystyrene.

Comparative Synthesis Example 4

Synthesis of Polyimide Resin (A-12)

In the same formulation as Synthesis Example 13 except that diamine ($X^{AM}$-1) was replaced with 1.38 g (7.48 mmol) of 4,4'-benzidine, polyimide resin (A-12) was obtained. When the molecular weight of this polymer was measured by GPC, it had a weight average molecular weight of 31,000 in terms of polystyrene.

Comparative Synthesis Example 5

Synthesis of Polyimide Resin (A-13)

In the same formulation as Synthesis Example 13 except that diamine ($X^{AM}$-1) was replaced with 2.19 g (7.48 mmol) of 1,4-bis(4-aminophenoxy)benzene, polyamide-imide resin (A-13) was obtained. When the molecular weight of this polymer was measured by GPC, it had a weight average molecular weight of 32,000 in terms of polystyrene.

Comparative Synthesis Example 6

Synthesis of Polyimide Resin (A-14)

In the same formulation as Synthesis Example 13 except that diamine ($X^{AM}$-1) was replaced with 2.61 g (7.48 mmol) of 9,9'-bis(4-aminophenyl)fluorene, polyimide resin (A-14) was obtained. When the molecular weight of this polymer was measured by GPC, it had a weight average molecular weight of 32,000 in terms of polystyrene.

Comparative Synthesis Example 7

Synthesis of Polyimide Resin (A-15)

In the same formulation as Synthesis Example 13 except that diamine ($X^{AM}$-1) was replaced with 1.99 g (7.48 mmol) of 4,4'-cyclohexylidenedianiline, polyimide resin (A-15) was obtained. When the molecular weight of this polymer was measured by GPC, it had a weight average molecular weight of 32,000 in terms of polystyrene.

II. Preparation of Photosensitive Resin Composition

By using resins (A-1) to (A-8) synthesized in the above-described Synthesis Example 9 to Synthesis Example 16 and resins (A-9) to (A-15) synthesized in Comparative Synthesis Examples 1 to 7 as a base resin, resin compositions with 30% by mass of resin were prepared according to the compositions and containing amounts described in Table 1. Thereafter, the respective resin compositions were stirred, mixed and dissolved, and then, subjected to microfiltration using a 1.0 μm filter made of Teflon (Registered Trademark) to obtain the respective photosensitive resin compositions. For the solvents in the Table, PGMEA represents propylene glycol monomethyl ether acetate, and GBL represents γ-butyrolactone.

TABLE 1

|  | Resin Component (A) | Photosensitizer Component (B) | Crosslinking agent Component (C) | | Solvent Component (D) | |
| --- | --- | --- | --- | --- | --- | --- |
| Photosensitive resin composition 1 | A-1 100 parts by weight | Photosensitizer 1 15 parts by weight | CL-1 10 parts by weight | CL-2 15 parts by weight | PGMEA 207 parts by weight | GBL 23 parts by weight |
| Photosensitive resin composition 2 | A-2 100 parts by weight | Photosensitizer 1 15 parts by weight | CL-1 10 parts by weight | CL-2 15 parts by weight | PGMEA 207 parts by weight | GBL 23 parts by weight |
| Photosensitive resin composition 3 | A-3 100 parts by weight | Photosensitizer 1 15 parts by weight | CL-1 10 parts by weight | CL-2 15 parts by weight | PGMEA 207 parts by weight | GBL 23 parts by weight |
| Photosensitive resin composition 4 | A-4 100 parts by weight | Photosensitizer 1 15 parts by weight | CL-1 10 parts by weight | CL-2 15 parts by weight | PGMEA 207 parts by weight | GBL 23 parts by weight |
| Photosensitive resin composition 5 | A-5 100 parts by weight | Photosensitizer 1 15 parts by weight | CL-1 10 parts by weight | CL-2 15 parts by weight | PGMEA 207 parts by weight | GBL 23 parts by weight |
| Photosensitive resin composition 6 | A-6 100 parts by weight | Photosensitizer 1 15 parts by weight | CL-1 10 parts by weight | CL-2 15 parts by weight | PGMEA 207 parts by weight | GBL 23 parts by weight |
| Photosensitive resin composition 7 | A-7 100 parts by weight | Photosensitizer 1 15 parts by weight | CL-1 10 parts by weight | CL-2 15 parts by weight | PGMEA 207 parts by weight | GBL 23 parts by weight |
| Photosensitive resin composition 8 | A-8 100 parts by weight | Photosensitizer 1 15 parts by weight | CL-1 10 parts by weight | CL-2 15 parts by weight | PGMEA 207 parts by weight | GBL 23 parts by weight |
| Comparative photosensitive resin composition 1 | A-9 100 parts by weight | Photosensitizer 1 15 parts by weight | CL-1 10 parts by weight | CL-2 15 parts by weight | PGMEA 207 parts by weight | GBL 23 parts by weight |
| Comparative photosensitive resin composition 2 | A-10 100 parts by weight | Photosensitizer 1 15 parts by weight | CL-1 10 parts by weight | CL-2 15 parts by weight | PGMEA 207 parts by weight | GBL 23 parts by weight |
| Comparative photosensitive resin composition 3 | A-11 100 parts by weight | Photosensitizer 1 15 parts by weight | CL-1 10 parts by weight | CL-2 15 parts by weight | PGMEA 207 parts by weight | GBL 23 parts by weight |
| Comparative photosensitive resin composition 4 | A-12 100 parts by weight | Photosensitizer 1 15 parts by weight | CL-1 10 parts by weight | CL-2 15 parts by weight | PGMEA 207 parts by weight | GBL 23 parts by weight |
| Comparative photosensitive resin composition 5 | A-13 100 parts by weight | Photosensitizer 1 15 parts by weight | CL-1 10 parts by weight | CL-2 15 parts by weight | PGMEA 207 parts by weight | GBL 23 parts by weight |
| Comparative photosensitive resin composition 6 | A-14 100 parts by weight | Photosensitizer 1 15 parts by weight | CL-1 10 parts by weight | CL-2 15 parts by weight | PGMEA 207 parts by weight | GBL 23 parts by weight |
| Comparative photosensitive resin composition 7 | A-15 100 parts by weight | Photosensitizer 1 15 parts by weight | CL-1 10 parts by weight | CL-2 15 parts by weight | PGMEA 207 parts by weight | GBL 23 parts by weight |

Photosensitive resin compositions 1 to 8 shown in Table 1 relate to the above-mentioned positive photosensitive resin composition according to the present invention. Comparative photosensitive resin compositions 1 to 7 are formed by using the polymers synthesized in Comparative Synthesis Examples 1 to 7 as a base resin instead of the polymer according to the present invention in the above-mentioned positive photosensitive resin composition according to the present invention.

TABLE 2

|  | Resin Component (A') | Photoacid generator Component (B') | Crosslinking agent Component (C') | | Solvent Component (D) | |
| --- | --- | --- | --- | --- | --- | --- |
| Photosensitive resin composition 9 | A-1 100 parts by weight | Photoacid generator 1 15 parts by weight | CL-3 15 parts by weight | CL-2 15 parts by weight | PGMEA 207 parts by weight | GBL 23 parts by weight |
| Photosensitive resin composition 10 | A-2 100 parts by weight | Photoacid generator 1 15 parts by weight | CL-3 15 parts by weight | CL-2 15 parts by weight | PGMEA 207 parts by weight | GBL 23 parts by weight |
| Photosensitive resin composition 11 | A-3 100 parts by weight | Photoacid generator 1 15 parts by weight | CL-3 15 parts by weight | CL-2 15 parts by weight | PGMEA 207 parts by weight | GBL 23 parts by weight |
| Photosensitive resin composition 12 | A-4 100 parts by weight | Photoacid generator 1 15 parts by weight | CL-3 15 parts by weight | CL-2 15 parts by weight | PGMEA 207 parts by weight | GBL 23 parts by weight |
| Photosensitive resin composition 13 | A-5 100 parts by weight | Photoacid generator 1 15 parts by weight | CL-3 15 parts by weight | CL-2 15 parts by weight | PGMEA 207 parts by weight | GBL 23 parts by weight |
| Photosensitive resin composition 14 | A-6 100 parts by weight | Photoacid generator 1 15 parts by weight | CL-3 15 parts by weight | CL-2 15 parts by weight | PGMEA 207 parts by weight | GBL 23 parts by weight |
| Photosensitive resin composition 15 | A-7 100 parts by weight | Photoacid generator 1 15 parts by weight | CL-3 15 parts by weight | CL-2 15 parts by weight | PGMEA 207 parts by weight | GBL 23 parts by weight |
| Photosensitive resin composition 16 | A-8 100 parts by weight | Photoacid generator 1 15 parts by weight | CL-3 15 parts by weight | CL-2 15 parts by weight | PGMEA 207 parts by weight | GBL 23 parts by weight |
| Comparative photosensitive resin composition 8 | A-9 100 parts by weight | Photoacid generator 1 15 parts by weight | CL-3 15 parts by weight | CL-2 15 parts by weight | PGMEA 207 parts by weight | GBL 23 parts by weight |
| Comparative photosensitive resin composition 9 | A-10 100 parts by weight | Photoacid generator 1 15 parts by weight | CL-3 15 parts by weight | CL-2 15 parts by weight | PGMEA 207 parts by weight | GBL 23 parts by weight |
| Comparative photosensitive resin composition 10 | A-11 100 parts by weight | Photoacid generator 1 15 parts by weight | CL-3 15 parts by weight | CL-2 15 parts by weight | PGMEA 207 parts by weight | GBL 23 parts by weight |
| Comparative photosensitive resin composition 11 | A-12 100 parts by weight | Photoacid generator 1 15 parts by weight | CL-3 15 parts by weight | CL-2 15 parts by weight | PGMEA 207 parts by weight | GBL 23 parts by weight |
| Comparative photosensitive resin composition 12 | A-13 100 parts by weight | Photoacid generator 1 15 parts by weight | CL-3 15 parts by weight | CL-2 15 parts by weight | PGMEA 207 parts by weight | GBL 23 parts by weight |
| Comparative photosensitive resin composition 13 | A-14 100 parts by weight | Photoacid generator 1 15 parts by weight | CL-3 15 parts by weight | CL-2 15 parts by weight | PGMEA 207 parts by weight | GBL 23 parts by weight |
| Comparative photosensitive resin composition 14 | A-15 100 parts by weight | Photoacid generator 1 15 parts by weight | CL-3 15 parts by weight | CL-2 15 parts by weight | PGMEA 207 parts by weight | GBL 23 parts by weight |

Photosensitive resin compositions 9 to 16 shown in Table 2 relate to the above-mentioned negative photosensitive resin composition according to the present invention. Comparative photosensitive resin compositions 8 to 14 are formed by using the polymers synthesized in Comparative Synthesis Examples 1 to 7 as a base resin instead of the polymer according to the present invention in the above-mentioned negative photosensitive resin composition according to the present invention.

Note that, in Table 1 and Table 2, details of the photosensitizer (photosensitizer 1), which is a quinonediazide compound, the photoacid generator (photoacid generator 1), and the crosslinking agents (CL-1) to (CL-3) are as follows.

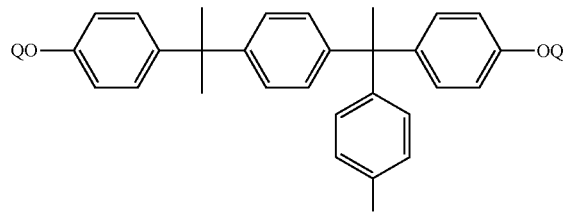

Photosensitizer (Photosensitizer 1)

wherein Q represents a 1,2-naphthoquinonediazidosulfonyl group represented by the following formula (24) or a hydrogen atom, and 90% of Q is replaced with the 1,2-naphthoquinonediazidosulfonyl group represented by the following formula (24).

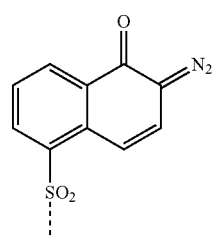

(24)

Photoacid Generator (Photoacid Generator 1)

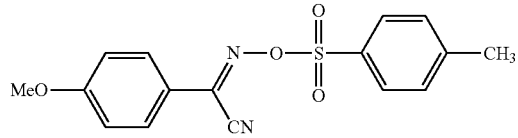

Crosslinking Agent (CL-1)

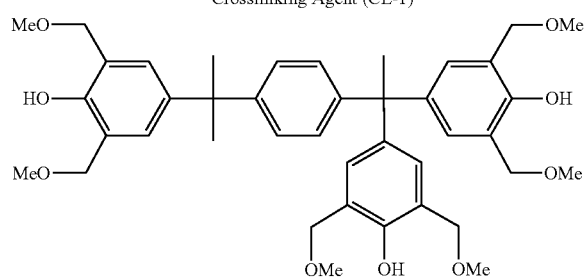

Crosslinking Agent (CL-2)

Epoxy resin: manufactured by ADEKA CORPORATION, EP-4000L

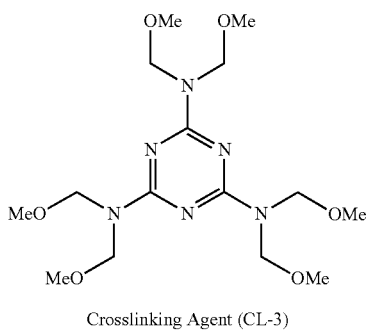 [SMILES: COCN(COC)c1nc(N(COC)COC)nc(N(COC)COC)n1]

Crosslinking Agent (CL-3)

III. Patterning

By dispensing 5 mL of the above-described photosensitive resin compositions 1 to 16 and comparative photosensitive resin compositions 1 to 14 onto a silicon substrate and then rotating the substrate, that is, by the spin coating method, each of these compositions was coated so as to have a film thickness of 10 μm after the heating of post-curing performed after the patterning. That is, it was examined in advance that the film thickness would be reduced after the post-curing step, and the rotation number upon coating was adjusted so that the finished film thickness after the post-curing becomes 10 μm.

Next, the compositions coated on the substrates were pre-baked on a hot plate at 100° C. for 2 minutes. Then, by using an i-line stepper NSR-2205i11 manufactured by Nikon Corporation, it was exposed with i-line for patterning. In the patterning, a mask for positive pattern or negative pattern was used appropriately in accordance with the photosensitive resin composition used. That mask has a pattern capable of forming 20 μm holes arranged by a fineness ratio of 1:1, and can form a hole pattern of 50 μm to 20 μm holes with 10 μm pitch, 20 μm to 10 μm holes with 5 μm pitch, or 10 μm to 1 μm holes with 1 μm pitch.

Next, for those to which the heating step (post-exposure bake) was performed, it was performed under conditions as shown in the following Table 4.

In the development step, an aqueous alkaline solution was used as the developing solution, and a 2.38% aqueous solution of tetramethylammonium hydroxide was used as the developing solution. After performing paddle development for 1 minute with the 2.38% aqueous solution of tetramethylammonium hydroxide (TMAH) three times, rinsing with ultrapure water was carried out.

Then, the obtained pattern on the substrate was post-cured using an oven at 200° C. for 2 hours while purging the oven with nitrogen.

Next, each substrate was cut out so that the shape of the obtained hole pattern can be observed, and the shape of the hole pattern was observed by using a scanning electron microscope (SEM). The aperture of the smallest opening hole at a film thickness of 10 μm after the post-curing was determined, and the shape of the pattern was evaluated. Together with these results, the sensitivities at which the minimum pattern could be formed are shown in Table 3 and Table 4.

The shape of the hole pattern was evaluated by the criteria as described below, and the evaluation results were shown in Table 3 and Table 4. However, when the above-described compositions were not a uniform solution and appeared to be muddy, they were determined not to be evaluable.

Good: holes were observed in a rectangular shape or forward taper shape (the shape in which the dimension of the upper part of the hole is larger than the dimension of the bottom part)

Poor: holes were observed in a reverse taper shape (the shape in which the dimension of the upper part of the hole is smaller than the dimension of the bottom part) or overhang shape (the shape in which the upper part of the hole protrudes), remarkable film thinning was observed, or residue at the bottom part of the hole.

IV. Elongation at Break and Breaking Strength

The above-described photosensitive resin compositions 1 to 16 and comparative photosensitive resin compositions 1 to 14 were spin coated onto aluminum substrates so that the finished film thickness after the curing becomes 10 μm. Next, the compositions coated on the substrates were prebaked on a hot plate at 110° C. for 4 minutes to obtain photosensitive resin films.

Then, the obtained films were cured using an oven at 200° C. for 2 hours while purging the oven with nitrogen to obtain photosensitive resin cured films. Next, the wafers with the cured films were cut into a strip form with a width of 10 mm and a length of 60 mm, and by immersing them in hydrochloric acid with a concentration of 20% by mass, the cured films were peeled off the substrate. For the obtained cured films, the elongation at break and the breaking strength was measured by using an autograph AGX-1KN manufactured by Shimadzu Corporation. The measurement was made 10 times for one sample, and the average value thereof is shown in Table 2. The elongation at break is preferably large, and it is more preferably 20% or more. The breaking strength is preferably large, and it is more preferably 100 MPa or more.

V. Solvent Solubility

By using the above-described resins (A-1) to (A-15) synthesized in Synthesis Example 9 to Synthesis Example 16 and Comparative Synthesis Examples 1 to 7 as a base resin, solutions with 30% by mass of resin in propylene glycol monomethyl ether acetate were prepared. After stirring the solutions overnight, the state of solutions was evaluated as Good when the solution was transparent, Fair when the solution was clouded, and Poor when the resin was not dissolved or became gelated, and the results are shown in Table 3.

Firstly, by using positive photosensitive resin compositions (photosensitive resin compositions 1 to 8 and comparative photosensitive resin compositions 1 to 7), results obtained by carrying out the patterning, and the elongation at break and breaking strength of the cured films, and results of the solvent solubility are shown in Table 3. Note that the solvent solubility in the Table is of the respective resins (A-1) to (A-15) included in photosensitive resin compositions 1 to 8 and comparative photosensitive resin compositions 1 to 7.

TABLE 3

| | Composition | Pattern | Hole shape | Minimum hole diameter (μm) | Sensitivity (mJ/cm$^2$) | Elongation at break (%) | Breaking strength (MPa) | Solvent solubility |
|---|---|---|---|---|---|---|---|---|
| Example 1 | Photosensitive resin composition 1 | Positive type | Good | 5 | 340 | 30 | 111 | Good |
| Example 2 | Photosensitive resin composition 2 | Positive type | Good | 5 | 340 | 32 | 113 | Good |
| Example 3 | Photosensitive resin composition 3 | Positive type | Good | 5 | 360 | 33 | 110 | Good |
| Example 4 | Photosensitive resin composition 4 | Positive type | Good | 5 | 340 | 30 | 111 | Good |
| Example 5 | Photosensitive resin composition 5 | Positive type | Good | 8 | 380 | 30 | 103 | Good |
| Example 6 | Photosensitive resin composition 6 | Positive type | Good | 8 | 360 | 32 | 105 | Good |
| Example 7 | Photosensitive resin composition 7 | Positive type | Good | 5 | 360 | 35 | 103 | Good |
| Example 8 | Photosensitive resin composition 8 | Positive type | Good | 8 | 380 | 33 | 105 | Good |
| Comparative Example 1 | Comparative photosensitive resin composition 1 | Positive type | Good | 6 | 340 | 25 | 85 | Good |
| Comparative Example 2 | Comparative photosensitive resin composition 2 | Positive type | Evaluation not possible | | | 20 | 105 | Poor |
| Comparative Example 3 | Comparative photosensitive resin composition 3 | Positive type | Good | 5 | 340 | 40 | 80 | Good |
| Comparative Example 4 | Comparative photosensitive resin composition 4 | Positive type | Evaluation not possible | | | 21 | 110 | Poor |
| Comparative Example 5 | Comparative photosensitive resin composition 5 | Positive type | Good | 8 | 360 | 32 | 88 | Fair |
| Comparative Example 6 | Comparative photosensitive resin composition 6 | Positive type | Good | 8 | 380 | 22 | 109 | Fair |
| Comparative Example 7 | Comparative photosensitive resin composition 7 | Positive type | Good | 8 | 360 | 24 | 95 | Good |

As shown in Table 3, the positive photosensitive resin compositions according to the present invention exhibit a good pattern shape in the development with the aqueous alkaline solution, and the minimum hole dimensions thereof exhibit smaller values than a finished film thickness of 10 μm, and therefore, it can be understood that the aspect ratio of 1 or more can be accomplished.

In addition, as shown in Table 3, it can be understood that cured films having good mechanical properties while exhibiting good solvent solubility are obtained, that is, the mechanical properties and solvent solubility of cured films are both achieved.

On the other hand, although cured films using comparative photosensitive resin compositions 2 and 4 to 6 have mechanical properties equivalent to those of the cured films obtained from compositions according to the present invention, the solvent solubility of the resins thereof is low (Comparative Examples 2 and 4 to 6). Otherwise, for those having excellent solvent solubility, mechanical properties of the cured films are poor (Comparative Examples 1, 3 and 7). As stated above, in the cured films using comparative photosensitive resin compositions in which resins not comprising a structural unit represented by general formula (2) are used as a base resin, it can be understood that it is difficult to achieve both of the above-described performances.

In particular, in the case of the cured film of Comparative Example 6 using the resin into which the 9,9-diphenylfluorene skeleton was introduced (see International Publication No. WO 2019/151336), it has mechanical properties equivalent to those of Examples, but the solvent solubility of the resin is low, and in the case of the cured film of Comparative Example 7 using the resin having the 1,1-diphenylcyclohexane structure (see Japanese Patent Laid-Open No. 2019-14828), it has solvent solubility to some extent, but the strength of the cured film does not reach that of Examples. Accordingly, it is obvious that only comprising a cardo structure as a structural unit is not sufficient to achieve both mechanical properties of the cured film and solvent solubility as achieved in the case of the present invention.

Next, by using negative photosensitive resin compositions (photosensitive resin compositions 9 to 16 and comparative photosensitive resin compositions 8 to 14), results obtained by carrying out the patterning, and the elongation at break and breaking strength of the cured films are shown in Table 4. Note that the solvent solubility of the respective resins (A-1) to (A-15) included in photosensitive resin compositions 9 to 16 and comparative photosensitive resin compositions 8 to 14 is as shown in Table 3.

TABLE 4

|  | Composition | Pattern | Post-exposure bake | Hole shape | Minimum hole diameter (μm) | Sensitivity (mJ/cm$^2$) | Elongation at break (%) | Breaking strength (MPa) |
| --- | --- | --- | --- | --- | --- | --- | --- | --- |
| Example 9 | Photosensitive resin composition 9 | Negative type | 100° C. × 120 sec | Good | 7 | 660 | 20 | 121 |
| Example 10 | Photosensitive resin composition 10 | Negative type | 100° C. × 120 sec | Good | 7 | 660 | 22 | 123 |
| Example 11 | Photosensitive resin composition 11 | Negative type | 100° C. × 120 sec | Good | 7 | 680 | 23 | 120 |
| Example 12 | Photosensitive resin composition 12 | Negative type | 100° C. × 120 sec | Good | 7 | 660 | 22 | 121 |
| Example 13 | Photosensitive resin composition 13 | Negative type | 100° C. × 120 sec | Good | 10 | 680 | 21 | 115 |
| Example 14 | Photosensitive resin composition 14 | Negative type | 100° C. × 120 sec | Good | 10 | 660 | 23 | 118 |
| Example 15 | Photosensitive resin composition 15 | Negative type | 100° C. × 120 sec | Good | 7 | 660 | 25 | 114 |
| Example 16 | Photosensitive resin composition 16 | Negative type | 100° C. × 120 sec | Good | 10 | 680 | 24 | 115 |
| Comparative Example 8 | Comparative photosensitive resin composition 8 | Negative type | 100° C. × 120 sec | Good | 8 | 660 | 15 | 98 |
| Comparative Example 9 | Comparative photosensitive resin composition 9 | Negative type | Evaluation not possible | Evaluation not possible |  |  | 13 | 118 |
| Comparative Example 10 | Comparative photosensitive resin composition 10 | Negative type | 100° C. × 120 sec | Good | 7 | 660 | 30 | 92 |
| Comparative Example 11 | Comparative photosensitive resin composition 11 | Negative type | Evaluation not possible | Evaluation not possible |  |  | 15 | 121 |
| Comparative Example 12 | Comparative photosensitive resin composition 12 | Negative type | 100° C. × 120 sec | Good | 10 | 660 | 20 | 98 |
| Comparative Example 13 | Comparative photosensitive resin composition 13 | Negative type | 100° C. × 120 sec | Good | 10 | 680 | 16 | 118 |
| Comparative Example 14 | Comparative photosensitive resin composition 14 | Negative type | 100° C. × 120 sec | Good | 10 | 680 | 15 | 115 |

As shown in Table 4, the negative photosensitive resin compositions according to the present invention exhibit a good pattern shape in the development with the aqueous alkaline solution, and the minimum hole dimensions thereof exhibit smaller values than a finished film thickness of 10 μm, and therefore, it can be understood that the aspect ratio of 1 or more can be accomplished.

In addition, as shown in Table 4, it can be understood that cured films having good mechanical properties while exhibiting good solvent solubility are obtained, that is, the mechanical properties and solvent solubility of cured films are both achieved.

On the other hand, none of the cured films using comparative photosensitive resin compositions has mechanical properties (elongation at break and breaking strength) equivalent to those of the cured films obtained from compositions according to the present invention and also has excellent solvent solubility. As stated above, in the cured films using comparative photosensitive resin compositions in which resins not comprising a structural unit represented by general formula (2) are used as a base resin, it can be understood that it is difficult to achieve both of the above-described performances.

Note that the present invention is not limited to the embodiments described above. The embodiments described above are merely illustrations, and any embodiments having substantially the same configuration as and providing similar effects to the technical concept described in the claims of the present invention are encompassed in the technical scope of the present invention.

What is claimed is:

1. A resin comprising structural units represented by the following general formulas (2) and (3):

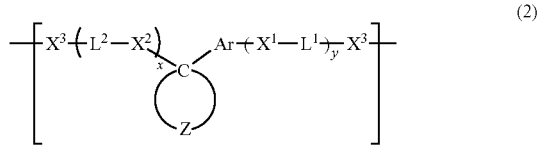

(2)

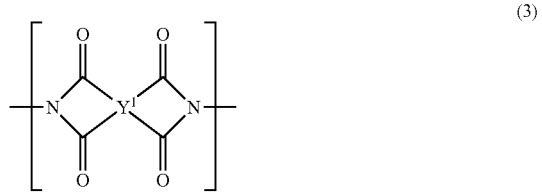

(3)

wherein Z represents a linear, branched or cyclic divalent hydrocarbon group having 2 to 30 carbon atoms that is optionally substituted with a heteroatom and optionally has an intervening heteroatom; $X^1$ to $X^3$ represent any of —$CO_2$—, —$CONR^{X1}$—, —O—, —$NR^{x1}$—, —S—, —$SO_2$—, —$SO_3$— and —$SO_2NR^{x1}$— and may be the same as or different from each other, provided that $R^{X1}$ is a hydrogen atom or a monovalent hydrocarbon group having 1 to 30 carbon atoms that is optionally substituted with a heteroatom and optionally has an intervening heteroatom; Ar represents a divalent aromatic group having 2 to 30 carbon atoms that is optionally substituted with a heteroatom and optionally has an intervening heteroatom; $L^1$ and $L^2$ independently represent a divalent hydrocarbon group having 1 to 30 carbon atoms that is optionally substituted with a heteroatom and optionally has an intervening heteroatom; x and y are each independently 0 or 1; and $Y^1$ represents a tetravalent hydrocarbon group having 1 to 100 carbon atoms that is optionally substituted with a heteroatom and optionally has an intervening heteroatom.

2. The resin according to claim 1, further comprising, in addition to the structural units (2) and (3), a structural unit represented by the following general formula (4):

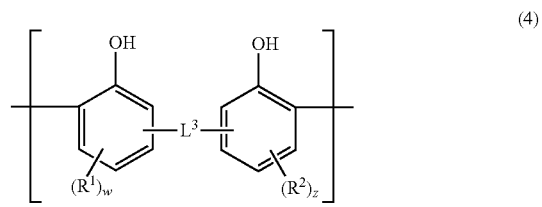

(4)

wherein $L^3$ is a single bond or a divalent linking group; $R^1$ to $R^2$ each independently represent any monovalent substituent; and w and z are 0 to 3, and when they are 2 or more, substituents represented by a plurality of $R^1$ and $R^2$ may be the same as or different from each other.

3. The resin according to claim 2, wherein $L^3$ in the general formula (4) is —$CR^{f1}R^{f2}$— or —$SO_2$—, provided that $R^{f1}$ to $R^{f2}$ are each independently a fluorine atom or a fluoroalkyl group having 1 to 10 carbon atoms.

4. A positive photosensitive resin composition comprising:
   (A) the resin according to claim 1;
   (B) a photosensitizer that generates an acid by light to increase a dissolution rate in an aqueous alkaline solution, and that is a compound having a quinonediazide structure; and
   (D) a solvent.

5. The positive photosensitive resin composition according to claim 4, further comprising: (C) at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'):

(C-1)

(C-2)

(C-2')

wherein a dotted line represents a bond; $R^c$ represents a linear, branched or cyclic alkyl group having 1 to 6 carbon atoms; and s is 1 or 2.

6. A negative photosensitive resin composition comprising:
(A') the resin according to claim 1;
(B') a photoacid generator;
(C') at least one crosslinking agent selected from an amino condensate modified with formaldehyde or formaldehyde-alcohol, a phenol compound having two or more methylol groups or alkoxymethylol groups on average in one molecule, a compound in which a hydrogen atom of a hydroxy group of a polyvalent phenol is replaced with a glycidyl group or a group having a glycidyl group, a compound in which a hydrogen atom of a hydroxy group of a polyvalent phenol is replaced with a substituent represented by the following formula (C-1), and a compound containing two or more groups represented by the following formula (C-2) or (C-2'):

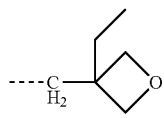
(C-1)

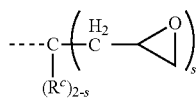
(C-2)

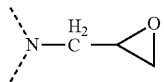
(C-2')

wherein a dotted line represents a bond; $R^c$ represents a linear, branched or cyclic alkyl group having 1 to 6 carbon atoms; and s is 1 or 2; and
(D) a solvent.

7. A patterning method comprising:
(1) applying the positive photosensitive resin composition according to claim 4 onto a substrate to form a photosensitive material film;
(2) heating the photosensitive material film;
(3) exposing the photosensitive material film with a high energy beam having a wavelength of 190 to 500 nm or an electron beam through a photomask; and
(4) developing the film with a developing solution of an aqueous alkaline solution.

8. A patterning method comprising:
(I) applying the negative photosensitive resin composition according to claim 6 onto a substrate to form a photosensitive material film;
(II) heating the photosensitive material film;
(III) exposing the photosensitive material film with a high energy beam having a wavelength of 190 to 500 nm or an electron beam through a photomask; and
(IV) developing the film with a developing solution of an aqueous alkaline solution.

9. The patterning method according to claim 8, comprising post-exposure heating between the exposure (III) and the development (IV).

10. A method of forming a cured film, comprising heating and post-curing a patterned film obtained by the patterning method according to claim 7 at a temperature of 100 to 300° C.

11. A method of forming a cured film, comprising heating and post-curing a patterned film obtained by the patterning method according to claim 8 at a temperature of 100 to 300° C.

12. An interlayer insulating film comprising a cured film formed by curing the positive photosensitive resin composition according to claim 4.

13. An interlayer insulating film comprising a cured film formed by curing the negative photosensitive resin composition according to claim 6.

14. A surface protective film comprising a cured film formed by curing the positive photosensitive resin composition according to claim 4.

15. A surface protective film comprising a cured film formed by curing the negative photosensitive resin composition according to claim 6.

16. An electronic component having the interlayer insulating film according to claim 1.

17. An electronic component having the interlayer insulating film according to claim 13.

18. An electronic component having the surface protective film according to claim 14.

19. An electronic component having the surface protective film according to claim 15.

* * * * *